United States Patent
Cumming et al.

(10) Patent No.: US 9,579,327 B2
(45) Date of Patent: Feb. 28, 2017

(54) SYNTHESIS OF CHIRAL 2-(1H-INDAZOL-6-YL)-SPIRO [CYCLOPROPANE-1,3'-INDOLIN]-2'-ONES

(71) Applicant: University Health Network, Toronto (CA)

(72) Inventors: Graham Cumming, Madrid (ES); Narendra Kumar B. Patel, Brampton (CA); Bryan T. Forrest, Burlington (CA); Yong Liu, Oakville (CA); Sze-Wan Li, Toronto (CA); Peter Brent Sampson, Oakville (CA); Louise G. Edwards, Mississauga (CA); Heinz W. Pauls, Oakville (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 14/580,658

(22) Filed: Dec. 23, 2014

(65) Prior Publication Data

US 2015/0133677 A1    May 14, 2015

Related U.S. Application Data

(63) Continuation of application No. 13/639,648, filed as application No. PCT/CA2011/000387 on Apr. 6, 2011, now Pat. No. 8,921,545.

(60) Provisional application No. 61/321,332, filed on Apr. 6, 2010, provisional application No. 61/321,329, filed on Apr. 6, 2010.

(30) Foreign Application Priority Data

Apr. 6, 2010    (WO) ................ PCT/CA2010/000518

(51) Int. Cl.
| C07D 403/04 | (2006.01) |
| --- | --- |
| C07D 231/56 | (2006.01) |
| A61K 31/5377 | (2006.01) |
| C07D 413/14 | (2006.01) |
| C07D 403/10 | (2006.01) |
| C07D 403/14 | (2006.01) |
| A61K 45/06 | (2006.01) |

(52) U.S. Cl.
CPC .......... *A61K 31/5377* (2013.01); *A61K 45/06* (2013.01); *C07D 231/56* (2013.01); *C07D 403/04* (2013.01); *C07D 403/10* (2013.01); *C07D 403/14* (2013.01); *C07D 413/14* (2013.01)

(58) Field of Classification Search
None
See application file for complete search history.

(56) References Cited

U.S. PATENT DOCUMENTS

| 4,642,309 A | 2/1987 | Michel et al. |
| --- | --- | --- |
| 5,182,397 A | 1/1993 | Condon et al. |
| 6,506,763 B2 | 1/2003 | Tang et al. |
| 7,148,249 B2 | 12/2006 | Kley et al. |
| 7,205,328 B2 | 4/2007 | He et al. |
| 7,429,609 B2 | 9/2008 | Ohi et al. |
| 8,263,596 B2 | 9/2012 | Sampson et al. |
| 8,481,525 B2 | 7/2013 | Sampson et al. |
| 8,481,533 B2 | 7/2013 | Sampson et al. |
| 8,765,748 B2 | 7/2014 | Pauls et al. |
| 8,921,545 B2 | 12/2014 | Cumming et al. |
| 2007/0135509 A1 | 6/2007 | Blackburn et al. |
| 2009/0054397 A1 | 2/2009 | Ohi et al. |
| 2011/0065702 A1 | 3/2011 | Pauls et al. |
| 2012/0149686 A1 | 6/2012 | Pauls et al. |
| 2013/0096301 A1 | 4/2013 | Cumming et al. |
| 2014/0045822 A1 | 2/2014 | Sampson et al. |
| 2014/0045838 A1 | 2/2014 | Sampson et al. |

FOREIGN PATENT DOCUMENTS

| CA | 2383623 A1 | 2/2000 |
| --- | --- | --- |
| CA | 2498781 A1 | 4/2004 |
| CA | 2690567 A1 | 12/2008 |
| CA | 2709536 A1 | 7/2009 |
| CA | 2781839 A1 | 6/2011 |
| JP | 2002522452 A | 7/2002 |
| JP | 2003535847 A | 12/2003 |
| JP | 2009173629 A | 8/2009 |

(Continued)

OTHER PUBLICATIONS

Adams et al., "Mapping the Kinase Domain of the Janus Kinase 3", Bioorganic & Medicinal Chemistry Letters, vol. 13, pp. 3105-3110 (2003).
Guan et al., "Design and synthesis of aminopropyl tetrahydroindole-based indolin-2-ones as selective and potent inhibitors of Src and Yes tyrosine kinase", Bioorganic & MedicinalChemistry Letters, vol. 14, pp. 187-190 (2004).
Hauf et al., "The small molecule Hesperadin reveals a role for Aurora B in correcting kinetochore-microtubule attachment and in maintaining the spindle assembly checkpoint", The Journal of Cell Biology, vol. 161, No. 2, pp. 281-294 (2003).
Howard et al., "Synthesis and aldose reductase inhibitory activity of substituted 2(1H)-benzimidazolone- and oxindole-1-acetic acids", Eur J Med Chem, vol. 27, pp. 779-789 (1992).
International Search Report mailed Apr. 6, 2009.
International Search Report mailed Aug. 2, 2011.

(Continued)

*Primary Examiner* — Kamal Saeed
(74) *Attorney, Agent, or Firm* — McCarter & English, LLP; Steven G. Davis; Wei Song

(57) ABSTRACT

The present invention is directed to novel synthetic methods for preparing a spiro cyclopropyl indolinone compound represented by Structural Formula (A):

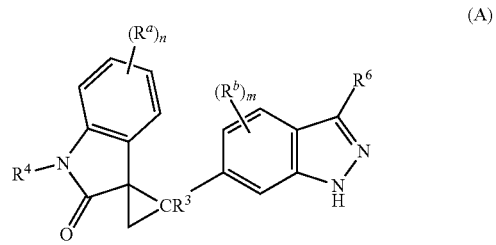

(A)

or its pharmaceutically acceptable salt thereof. Also included are synthetic intermediates described herein.

16 Claims, 1 Drawing Sheet

(56) References Cited

FOREIGN PATENT DOCUMENTS

| | | |
|---|---|---|
| WO | 9632380 A1 | 10/1996 |
| WO | 9640116 A1 | 12/1996 |
| WO | 9807695 A1 | 2/1998 |
| WO | 9910325 A1 | 3/1999 |
| WO | 0056709 A1 | 9/2000 |
| WO | 0153268 A2 | 7/2001 |
| WO | 0210137 A2 | 2/2002 |
| WO | 03101968 A1 | 12/2003 |
| WO | 2004037247 A1 | 5/2004 |
| WO | 2005058309 A1 | 6/2005 |
| WO | 2007008664 A1 | 1/2007 |
| WO | 2007058626 A1 | 5/2007 |
| WO | 2009079767 A1 | 7/2009 |
| WO | 2009111868 A1 | 9/2009 |
| WO | 2009124692 A1 | 10/2009 |
| WO | 2009132774 A1 | 11/2009 |
| WO | 2010000518 A1 | 1/2010 |
| WO | 2010115279 A1 | 10/2010 |
| WO | 2011115279 A1 | 9/2011 |
| WO | 2011123946 A1 | 10/2011 |
| WO | 2012118812 A2 | 9/2012 |

OTHER PUBLICATIONS

International Search Report mailed Jul. 8, 2010.
International Search Report mailed Jun. 23, 2011 for PCT/CA2011/000387 International Preliminary Report on Patentability mailed Oct. 18, 2012 for PCT/CA2011/000387.
Jiang et al., "Design, synthesis, and biological evaluations of novel oxindoles as HIV-1 non-nulceoside reverse transcriptase inhibitors. Part 2", Bioorganic & Medicinal Chemistry Letters, vol. 16, pp. 2109-2112 (2006).
Johnson et al., "Pharmacological and Functional Comparison of the Polo-like Kinase Family: Insight into Inhibitor and Substrate Specificity", American Chemical Society (2007).
Lin et al., "Synthesis and biological evaluation of 3-ethylidene-1,3-dihydro-indol-2-ones as novel checkpoint 1 inhibitors", Bioorganic & Medicinal Chemistry Letter, vol. 16, pp. 421-426 (2006).
Mohammadi et al., "Structures of the Tyrosine Kinase Domain of Fibroblast Growth Factor Receptor in Complex Inhibitors", Science, vol. 276, 955 (1997).
Moldvai et al., "Synthesis of Spiro[cyclopropone-1,3'[3H]indol]-2'(1'H)-ones with Antihypoxic Effects", Arch. Pharm. Pharm. Med. Chem. (1996).
Moshinsky et al., "SU9516: biochemicalanalysis of cdk inihibition and crystal structure in complex with cdk2", Biochemical and Biophysical Research Communications, vol. 310, pp. 1026-1031 (2003).
Rellos et al., "Structure and Regulation of the Human Nek2 Centrosomal Kinase", The Journal of Biological Chemistry, vol. 282, No. 9, pp. 6833-6842 (2007).
Sessa et al., Mechanism of Aurora B Activation by INCENP and Inhibitaion by Hesperadin.
Zhu et al., "Discovery and SAR of oxindole-pyridine-based protein kinase B/Akt inihibitors for treating cancers", Bioorganic & Medicinal Chemistry Letters, vol. 16, pp. 3424-3429 (2006).
Golub et al. Science (1999) vol. 286 531-537.
Lala et al. Cancer and Metastasis Reviews (1998), 17(1), 91-106.
Blackburn et al. caplus an 2002:594639 2002.
Carreira, Erick M. et al., Total Synthesis of (-)-Spirotryprostatin B: Synthesis and Related Studies; J. Am. Chem. Soc. 2005; 127, pp. 11505-11515.
Sharpless, K. Barry; Vicinal Diol Cyclic Sulfates: Like Epoxides Only More Reactive; American Chemical Society 1988; pp. 7538-7539.

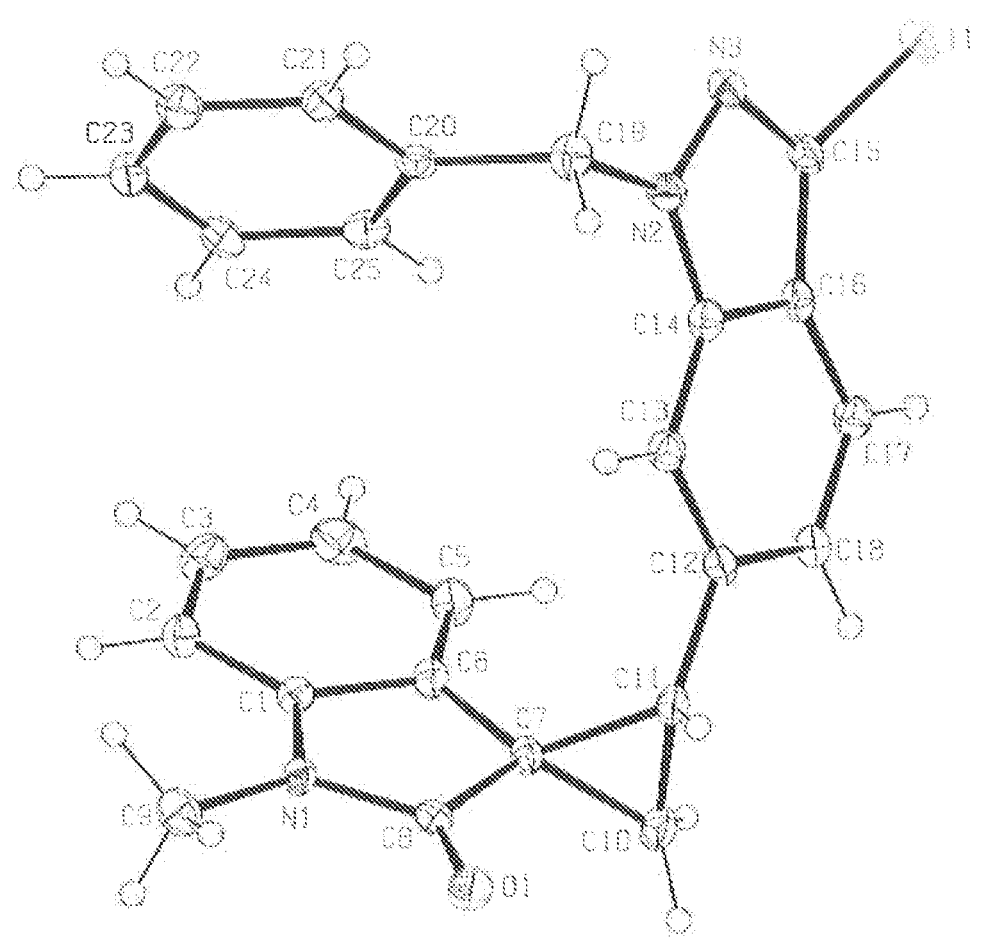

SYNTHESIS OF CHIRAL 2-(1H-INDAZOL-6-YL)-SPIRO [CYCLOPROPANE-1,3'-INDOLIN]-2'-ONES

RELATED APPLICATIONS

This application is a continuation of U.S. application Ser. No. 13/639,648, filed Oct. 5, 2012 and now U.S. Pat. No. 8,921,545, which is 35 U.S.C. §371 national stage filing of International Application No. PCT/CA2011/000387, filed Apr. 6, 2011, which, in turn, claims the benefit of U.S. Provisional Application Nos. 61/321,332, filed Apr. 6, 2010 and 61/321,329, filed Apr. 6, 2010. International Application No. PCT/CA2011/000387 also claims the benefit of International Application No. PCT/CA2010/000518, filed Apr. 6, 2010. The entire teachings of each of the aforementioned applications are incorporated herein by reference.

BACKGROUND OF THE INVENTION

Certain spiro cyclopropyl indolinone compounds, such as those described U.S. Provisional Application No. 61/211,988, published internation application WO2010/115279 and the international application entitled "Kinase Inhibitors and Method of Treating Cancer With Same", filed Apr. 6, 2011, are potent kinase inhibitors, such as polo-like kinase 4 (PLK4) and Aurora Kinases (the entire teachings of the three foregoing applications are incorporated herein by reference). A need exists for new synthestic methods of these compounds.

SUMMARY OF THE INVENTION

The present invention is directed to novel synthetic methods for preparing spiro cyclopropyl indolinone compounds represented by Structural Formula (A):

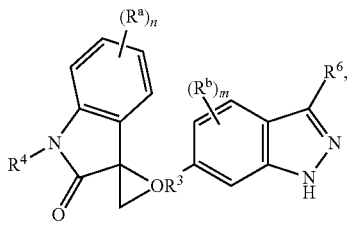

or a pharmaceutically acceptable salt thereof, wherein:
each of $R^a$ and $R^b$ independently is —H, halogen, —C(O)OR$^1$, —C(O)R$^1$, —C(S)R$^1$, —OC(O)R$^1$—, —C(O)NR$^1$R$^2$, —C(S)NR$^1$R$^2$, —OC(O)NR$^1$R$^2$, —S(O)R$^1$, —S(O)$_2$R$^1$, —SO$_3$R$^1$, —SO$_2$NR$^1$R$^2$, —OR$^1$, —SR$^1$, —NR$^1$R$^2$, —NR$^2$C(O)R$^1$, —NR$^2$S(O)R$^1$, —NR$^2$C(O)OR$^1$, —NR$^2$C(O)ONR$^1$R$^2$, —N(R$^2$)C(O)NR$^1$R$^2$, —NR$^2$SO$_2$NR$^1$R$^2$, —NR$^2$SO$_2$R$^1$; —NO$_2$, —CN, —NCS; or two ortho $R^a$ groups taken together form —O—[CH$_2$]$_p$—O—, —S—[CH$_2$]$_p$—S— or —[CH$_2$]$_q$—; or
$C_{1-10}$ aliphatic group optionally substituted with one or more substituents selected from the group consisting halogen, nitro, cyano, —N(R$^{21}$)$_2$, —C(O)N(R$^{21}$)$_2$, —C(O)N(R$^{21}$)$_2$, —NR$^{21}$C(O)R$^{21}$, —SO$_2$R$^{22}$, —SO$_2$N(R$^{21}$)$_2$, —NR$^{21}$SO$_2$R$^{22}$, —NR$^{21}$C(O)OR$^{21}$, —OC(O)N(R$^{21}$)$_2$, —NR$^{21}$C(O)N(R$^{21}$)$_2$, —NR$^{21}$C(O)ON(R$^{21}$)$_2$, —NR$^{21}$SO$_2$N(R$^{21}$)$_2$, —OR$^{21}$, —SR$^{21}$, $C_{1-10}$ haloalkoxy, —C(O)R$^{21}$, —C(O)OR$^{21}$ and —OC(O)R$^{21}$; or ($C_{0-10}$ alkylene)-Ar$^1$, wherein Ar$^1$ is a $C_{6-14}$ aryl group or a 5-14 membered heteroaryl group, each optionally and independently substituted with one or more substituents selected from the group consisting of halogen, nitro, cyano, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$-alkyl, —N(R$^{21}$)$_2$, —C(O)N(R$^{21}$)$_2$, —C(O)N(R$^{21}$)$_2$, —NR$^{21}$C(O)R$^{21}$, —SO$_2$R$^{22}$, —SO$_2$N(R$^{21}$)$_2$, —NR$^{21}$SO$_2$R$^{22}$, —NR$^{21}$C(O)N(R$^{21}$)$_2$, —NR$^{21}$C(O)ON(R$^{21}$)$_2$, —NR$^{21}$SO$_2$N(R$^{21}$)$_2$, —OR$^{21}$, —SR$^{21}$, $C_{1-10}$ haloalkoxy, —C(O)R$^{21}$, —C(O)OR$^{21}$, —OC(O)R$^{21}$, phenyl and 5-6 membered heteroaryl, wherein said phenyl and said 5-6 membered heteroaryl are each independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;
each $R^1$ independently is:
i) hydrogen;
ii) a $C_{6-14}$ aryl group or a 5-14 membered heteroaryl group, each optionally and independently substituted with one or more substituents selected from the group consisting of halogen, —NO$_2$, —CN, —NCS, $C_1$-$C_{10}$ aliphatic, ($C_{1-10}$ alkylene)-Ar$^{10}$, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —OC(O)N(R$^{11}$)$_2$, —S(O)R$^{12}$, —S(O)$_2$R$^{12}$, —SO$_3$R$^{12}$, —SO$_2$N(R$^{11}$)$_2$, —OR$^{10}$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$ and —NR$^{11}$SO$_2$R$^{12}$; or
iii) a $C_{1-10}$ aliphatic group optionally substituted with one or more substituents selected from the group consisting of halogen, —NO$_2$, —CN, —NCS, Ar$^{10}$, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —OC(O)N(R$^{11}$)$_2$, —S(O)R$^{12}$, —S(O)$_2$ R$^{12}$, —SO$_3$R$^{12}$, —SO$_2$N(R$^{11}$)$_2$, —OR$^{10}$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$ and —NR$^{11}$SO$_2$R$^{12}$,
provided that $R^1$ is other than hydrogen when $R^a$ or $R^b$ is —S(O)R$^1$, —S(O)$_2$R$^1$, —SO$_3$R$^1$, —NR$^2$S(O)R$^1$ or —NR$^2$SO$_2$R$^1$; and
each $R^2$ independently is —H or $C_1$-$C_6$ alkyl, or, taken together with NR$^1$, forms a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl;
$R^3$ is —H, halogen, $C_{1-6}$ alkyl or $C_{1-6}$ haloalkyl;
$R^4$ is —H, $C_{1-6}$ alkyl, phenyl, —C(O)($C_{1-6}$ alkyl), —C(O)(phenyl), —C(O)O($C_{1-6}$ alkyl), —C(O)O(phenyl), —S(O)$_2$ ($C_{1-6}$ alkyl) or —S(O)$_2$(phenyl), wherein each alkyl in the groups represented by $R^4$ is optionally substituted with one or more substituents selected from the group consisting of halogen, hydroxy, nitro, cyano, amino, —C(O)NH$_2$, phenyl, 5-6 membered heteroaryl, $C_{1-6}$ alkoxy, $C_{1-6}$ alkylamino, $C_{1-6}$ dialkylamino and $C_{1-6}$ haloalkoxy, and wherein each phenyl in the groups represented by $R^4$ is optionally substituted with one or more substituents selected from the group consisting of halogen, hydroxy, nitro, cyano, amino, $C_{1-6}$ alkyl, $C_{1-6}$ haloalkyl, $C_{1-6}$ alkoxy and $C_{1-6}$ haloalkoxy;

$R^6$ is hydrogen, halogen, nitro, cyano, R', —OR, —SR, —N(R)$_2$, —C(O)R, —C(O)OR, —OC(O)R, —C(O)N(R)$_2$, —OC(O)N(R)$_2$, —NRC(O)R, —NRC(O)OR, —SOR', —SO$_2$R', —SO$_3$R', —SO$_2$N(R)$_2$, —NRS(O)R', —NRSO$_2$R', —NRC(O)N(R)$_2$, —NRC(O)ON(R)$_2$, or —NRSO$_2$N(R)$_2$;

each $R^{10}$ independently is:
i) hydrogen;
ii) a $C_{6-14}$ aryl group or a 5-14 membered heteroaryl group, each optionally and independently substituted with one or more substituents selected from the group consisting of halogen, nitro, cyano, hydroxy, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ alkoxy, $C_{1-10}$ haloalkoxy, $C_{1-10}$ alkylcarbonyloxy, $C_{1-10}$ alkoxycarbonyl and $C_{1-10}$ alkylcarbonyl; or
iii) a $C_{1-10}$ alkyl group optionally substituted with one or more substituents selected from the group consisting of halogen, nitro, cyano, hydroxy, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each $R^{11}$ independently is $R^{10}$, —CO$_2$R$^{10}$, —SO$_2$R$^{10}$ or —C(O)R$^{10}$, or —N(R$^{11}$)$_2$ taken together is a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl; and each $R^{12}$ is independently is $R^{10}$ provided that $R^{12}$ is not hydrogen;

each $R^{21}$ independently is hydrogen, $C_{1-6}$ alkyl, phenyl or 5-6 membered heteroaryl, wherein each of the phenyl and heteroaryl groups represented by $R^{21}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{21}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy; or N(R$^{21}$)$_2$ forms a non-aromatic heterocyclic group optionally substituted with one or more substituents selected from the group consisting of halogen, hydroxy, nitro, cyano, =O, $C_{1-3}$ alky, $C_{1-3}$ haloalkyl, $C_{1-3}$ alkoxy, $C_{1-3}$ haloalkoxy and amino; and each $R^{22}$ independently $C_{1-6}$ alkyl, phenyl or 5-6 membered heteroaryl, wherein each of the phenyl and heteroaryl groups represented by $R^{22}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{22}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each R independently is hydrogen, $C_{1-10}$ aliphatic, phenyl or 5-6 membered heteroaryl, wherein the aliphatic group represented by R is optionally substituted with one or more substituents selected from the group consisting of halogen, hydroxy, nitro, cyano, amino, phenyl, 5-6 membered heteroaryl, $C_{1-6}$ alkoxy, $C_{1-6}$ haloalkoxy, and wherein each of the phenyl and heteroaryl groups represented by R, and the phenyl and heteroaryl substituents for the aliphatic group represented by R independently are optionally and independently substituted with one or more substituents selected from the group consisting of halogen, hydroxy, nitro, cyano, amino, $C_{1-6}$ alkyl, $C_{1-6}$ haloalkyl, $C_{1-6}$ alkoxy, $C_{1-6}$ haloalkoxy, or N(R)$_2$ forms a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl; and each R' independently is $C_{1-10}$ aliphatic, phenyl, 5-12 membered heteroaryl or 9-12 membered heterocyclyl group, wherein the aliphatic group represented by R' is optionally substituted with one or more substituents selected from the group consisting of halogen, hydroxy, nitro, cyano, amino, phenyl, 5-12 membered heteroaryl, 9-12 membered heterocyclyl group, $C_1$-$C_6$ alkoxy, $C_1$-$C_6$ haloalkoxy, $C_{1-6}$ alkylamino, $C_{1-6}$ dialkylamino, —C(O)H, —C(O)($C_1$-$C_6$ alkyl), —C(O)($C_1$-$C_6$ haloalkyl), —C(O)(phenyl), —C(O)(non-aromatic heterocyclic group), —C(O)O(C1-C6 alkyl), —C(O)O(C1-C6 haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl) and —S(O)$_2$(phenyl), and wherein each of the phenyl, heteroaryl and heterocyclyl groups represented by R', and the phenyl, heteroaryl and heterocyclyl groups in the substituents for the aliphatic group represented by R' independently are optionally substituted with one or more substituents selected from the group consisting of halogen, —OH, —SH, —C(O)H, nitro, cyano, amino, $C_{1-6}$ alkylamino, $C_{1-6}$ dialkylamino, ($C_{1-6}$ dialkylamino)$C_{1-6}$ dialkylamino, $C_1$-$C_6$ alkyl, $C_1$-$C_6$ haloalkyl, —O($C_{1-6}$ alkyl), —O-(non-aromatic heterocyclic group), —S($C_{1-6}$ alkyl), —O($C_{1-6}$ haloalkyl), ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, ($C_{1-6}$ dialkylamino)$C_{1-6}$ alkoxy, (phenyl)$C_{1-6}$ alkyl, (5-6 membered heteroaryl)$C_{1-6}$ alkyl, (non-aromatic heterocyclic group)$C_{1-6}$ alkyl (optionally substituted with halogen, —OH, $C_{1-6}$ hydroxyalkyl, $C_{5-7}$ cycloalkyl $C_{1-6}$ alkyl, ($C_{1-6}$ alkoxy)$C_{1-6}$ alkyl, $C_{1-6}$ acyl, $C_{1-6}$ alkylamino, di($C_{1-6}$ alkyl)amino or non-aromatic heterocyclic group), (5-6 membered heteroaryl)$C_{1-6}$ alkoxy, (non-aromatic heterocyclic group)$C_{1-6}$ alkoxy, —C(O)($C_1$-$C_6$ alkyl), —C(O)($C_1$-$C_6$ haloalkyl), —C(O)(phenyl), —C(O)(non-aromatic heterocyclic group), —C(O)O(C$_1$-C6 alkyl), —C(O)O($C_1$-$C_6$ haloalkyl), —C(O)O(phenyl), —OC(O)($C_1$-$C_6$ alkyl), —OC(O)($C_1$-$C_6$ haloalkyl), —OC(O)(phenyl), —S(O)$_2$NH$_2$, —S(O)$_2$($C_1$-$C_6$ alkyl), —S(O)$_2$($C_{1-6}$ haloalkyl), and —S(O)$_2$(phenyl);

each $Ar^{10}$ independently is a $C_{6-14}$ aryl group or a 5-14 membered heteroaryl group, each optionally and independently substituted with one or more substituents selected from the group consisting of halogen, nitro, cyano, —OH, —SH, —O($C_{1-10}$ alkyl), —S($C_{1-10}$ alkyl), $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$-hydroxyalkyl, ($C_{1-10}$ aminoalkyl, ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ haloalkoxy, $C_{1-10}$ alkylcarbonyloxy, $C_{1-10}$ alkoxycarbonyl and $C_{1-10}$ alkylcarbonyl;

each p is 1, 2 or 3;
each q is 2, 3, 4 or 5;
n is 1, 2 or 3; and
m is 1 or 2.

Also included are synthetic intermediates described herein for preparing the spiro cyclopropyl indolinone compound of Structural Formula (A).

BRIEF DESCRIPTION OF DRAWINGS

The FIGURE is an ORTEP diagram for compound of Example 17.

DETAILED DESCRIPTION OF THE INVENTION

The present invention is directed to novel synthetic methods for preparing spiro cyclopropyl indolinone compounds represented by Structural Formula (A) or a pharmaceutically acceptable salt thereof. The method comprises the step of reaction 1, reaction 2, reaction 3, reaction 4, reaction 5, reaction 6, reaction 7, reaction 7a, reaction 8, reaction 8a, reaction 9, reaction 9a, reaction 10, reaction 10a, reaction 11 or reaction 12 described below or a combination thereof. For example, in one embodiment, the method comprises the steps of reaction 7a, reaction 8a, reaction 9, reaction 9a, reaction 10 (or reaction 10a). Alternatively, the method comprises the steps of reaction 7a, reaction 8a, reaction 9a, and reaction 11. In another alternative, the method comprises the steps of reaction 7a, reaction 8a, reaction 9a and reaction 12. In another alternative, the method comprises the steps of reaction 1, reaction 2, reaction 3, and reaction 4. In another alternative, the method comprises the steps of reaction 5 or reaction 6. In another alternative, the method comprises the steps of reaction 1, reaction 2, reaction 3, reaction 4, reaction 5, reaction 7a, reaction 8a, reaction 9a and reaction 10 (or reaction 10a). In another alternative, the method comprises the steps of reaction 1, reaction 2, reaction 3, reaction 4, reaction 6, reaction 7a, reaction 8a, reaction 9a and reaction 10 (or reaction 10a).

In one embodiment, the present invention is directed to a method (reaction 1) for preparing a N1-substituted indazole compound represented by Structural Formula (II) comprising reacting an indazole compound represented by the Structural Formula (I) with a nitrogen protecting reagent.

reaction 1

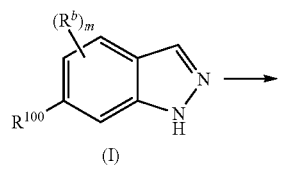

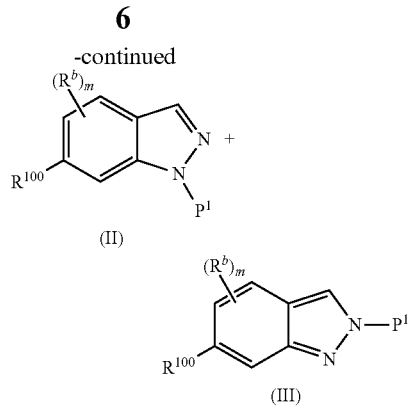

wherein:
$R^{100}$ is —Br or —C(=O)$R^3$;
$P^1$ is a nitrogen protecting group; and
$R^b$ and m are are as described above for Structural Formula (A).

As used herein, an "nitrogen protecting reagent" is a compound that would react with a nitrogen atom that carries an acidic proton and install a protecting group on that nitrogen atom. An "nitrogen protecting group" is a functional group that protects a nitrogen atom with an acidic proton from participating in reactions that are occurring in other parts of the molecule. Suitable nitrogen protecting groups are well known to those of ordinary skill in the art and include those found in T. W. Greene, Protecting Groups in Organic Synthesis, John Wiley & Sons, Inc. 1981, the entire teachings of which are incorporated herein by reference. Exemplary nitrogen protecting groups include, but are not limited to, include carbamates (e.g., methyl, ethyl, 9-fluorenylmethyl, 9-(2-sulfo)fluorenylmethyl, 9-(2,7-dibromo)fluorenylmethyl, 17-tetrabenzo[a, c, g, i]fluorenylmethyl, 2-chloro-3-indenylmethyl, benz[f]inden-3-ylmethyl-2,7-di-t-butyl-[9-(10,10-dioxo-10,10,10,10-tetrahydrothioxanthyl)]methyl, 1,1-dioxobenzo[b]thiophene-2-ylmethyl, 2,2,2-tricholoroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2-bromomethyl, 1,1-dimethyl-2,2,2-trichloroethyl, 1-methyl-1-(4-biphenylyl)ethyl, 1-(3,5-di-t-butylphenyl)-1-methylethyl, t-butyl, 1-adamantyl, 2-adamantyl, vinyl, allyl, 1-isopropylallyl, cinnamyl, 4-nitrocinnamyl, benzyl, p-methoxybenzyl, p-nitrobenzyl, p-bromobenzyl, p-chlorobenzyl, 2,4-dichlorobenzyl, m-nitrophenyl, 3,5-dimethoxybenzyl, 1-methyl-1-(3,5-dimethoxyphenyl)ethyl, α-methylnitropiperonyl, o-nitrobenzyl, 3,4-dimethoxy-6-nitrobenzyl, and phenyl(o-nitrophenyl)methyl), amides (e.g., n-formyl, n-acetyl, n-chloroacetyl, n-trichloroacetyl, n-trifluoroacetyl, n-phenylacetyl, and n-3-phenylpropionyl), sulfonamide (e.g., p-toluenesulfonyl, p-bromobenzenesulfonyl, 4-nitrobenzenesulfonyl and 2-nitrobenzesulfonyl) N-alkyl and N-aryl amines (e.g., N-methyl, N-t-butyl, N-allyl, N-benzyl, N-4-methoxybenzyl, N-2,4-dimethoxybenzyl, N-2-hydroxybenzyl) and tetrahydro-2H-pyran-2-yl.

In one embodiment, for reaction 1 described above, $R^3$ is —H.

In another embodiment, for reaction 1 described in any one of the foregoing embodiments, $P^1$ is —C(=O)O—$R^P$, —$SO_2$—$R^P$, tetrahydro-2H-pyran-2-yl or benzyl optionally substituted one or more (e.g., 2, 3 or 4) substituents independently selected from the group consisting of halogen, nitro, $C_{1-6}$ alkyl, $C_{1-6}$ haloalkyl, $C_{1-6}$ alkoxy, $C_{1-6}$ haloalkoxy and $(C_{1-6}$ alkoxy$)C_{1-6}$ alkyl; and $R^P$ is $C_{1-6}$ alkyl, $C_{1-6}$ haloalkyl, —$C_{1-6}$ alkylene-Si$(C_{1-6}$ alkyl$)_3$, phenyl optionally substituted with one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy and $(C_{1-6}$ alkoxy$)C_{1-6}$ alkyl.

In another embodiment, for reaction 1 described in any one of the foregoing embodiments, $P^1$ is a benzyl group optionally substituted with one or more (e.g., 2, 3 or 4) substituents independently selected from the group consisting of halogen, nitro, $C_{1-6}$ alkyl, $C_{1-6}$ haloalkyl, $C_{1-6}$ alkoxy, $C_{1-6}$ haloalkoxy and $(C_{1-6}$ alkoxy$)C_{1-6}$ alkyl. The N1-substituted indazole compound of Structural Formula (II) can be prepared by reacting the indazole compound represented by Structural Formula (I) with the appropriate optionally substituted benzyl halide in the presence of a base. Any suitable base can be used for such reaction. Examples of suitable bases include, but are not limited to, alkali metal hydride (e.g., NaH, KH or LiAlH$_4$), alkali metal $C_{1-6}$ alkoxide (e.g., NaOMe, KO$^t$Bu), alkali metal hydroxide (e.g., NaOH, KOH), alkali metal carbonate (e.g., Na$_2$CO$_3$, K$_2$CO$_3$ or Cs$_2$CO$_3$), amine (e.g., ethylamine, propylamine, dimethylamine, trimethylamine, triethylamine, isopropylethylamine or diisopropyethylamine), or ammonia.

Alternatively, for reaction 1 described in any one of the foregoing embodiments, $P^1$ is benzyl or p-methoxybenzyl and N1-substituted indazole of Structural Formula can be obtained by reacting the indazole compound of Structural Formula (I) with a base and the appropriate benzyl bromide or chloride. Such reaction can also generate the undesired N2-substituted indazole represented by Structural Formula (III). Various conditions may be employed to provide the N1-substituted indazole product. Exemplary conditions and the ratio of N1:N2 benzylation are listed in Table 1 below:

TABLE 1

| Entry | Solvent | Base | BnX | Temp | N1:N2 |
|---|---|---|---|---|---|
| 1 | THF | NaH | BnBr | RT | 1:1.7 |
| 2 | DMF | KO$^t$Bu | BnBr | RT | 1.5:1 |
| 3 | MeCN | KO$^t$Bu | BnBr | RT | 1.4:1 |
| 4 | MeCN | KO$^t$Bu | BnCl | RT | 1.5:1 |
| 5 | DMF | KO$^t$Bu | BnBr | RT | 1.4:1 |
| 6 | DMF | KO$^t$Bu | BnCl | RT | 1.5:1 |
| 7 | DMSO | KO$^t$Bu | BnBr | RT | 2.2:1 |
| 8 | DMSO | KO$^t$Bu | BnCl | RT | 3.0:1 |
| 9 | DMSO | KO$^t$Bu | BnBr | RT | 2.1:1 |
| 10 | DMSO | KO$^t$Bu | BnCl | RT | 2.5:1 |
| 11 | DMSO | LiO$^t$Bu | BnBr | RT | 1.3:1 |
| 12 | DMSO | NaO$^t$Bu | BnBr | RT | 1.8:1 |
| 13 | DMSO | KO$^t$Bu | BnBr | RT | 2.2:1 |
| 14 | DMSO | KOH | BnBr | RT | 1.7:1 |
| 15 | DMSO | KOH/18-cr-6 | BnBr | RT | 2.1:1 |
| 16 | DMSO | K$_2$CO$_3$/18-cr-6 | BnBr | RT | 1.7:1 |
| 17 | DMSO | Cs$_2$CO$_3$ | BnBr | RT | 2.0:1 |
| 18 | DMSO | KO$^t$Bu | BnCl | 70° C. | 2.1:1 |

The N1-substituted indazole can be obtained by purification, such as column chromatography.

Alternatively, thermal equilibration of the N2-substituted indazole to N1-substituted indazole can be carried out in the presence of catalytic amount (e.g., 10-20 mol %) of alkylating agent, such as benzyl bromide or p-methoxybenzyl chloride at temperatures ranging from 120-200° C., preferably 150-170° C. In this manner, a mixture of N2 and N1 substituted indazoles, obtained by any one of the conditions described in table 1, may be converted into substantially pure N1 isomer suitable for use as the starting material for reaction 2.

Reaction 1 described in any one of the foregoing embodiments can be carried out in any suitable solvent or solvents. In one embodiment, the reaction is carried out in an organic solvent or solvents, such as tetrahydrofuran (THF), dichloromethane (DCM), dimethylformamide (DMF), acetonitrile, or dimethyl sulfoxide (DMSO). Alternatively, when the base is compatible with aqueous condition, reaction 1 can be carried out in the presence of water. In one embodiment, the reaction is carried out in a mixture of water and an organic solve, such as those described above. When the organic solvent is not miscible with water, a phase transfer catalyst, such as a quaternary ammonium salt (e.g., tetrabutylammonium chloride, bromide or iodide) can be used.

In another embodiment, the present invention is directed to a method (reaction 2) of converting the N1-substituted indazole compound of Structural Formula (II) to a vinyl indazole compound represented by Structural Formula (IV):

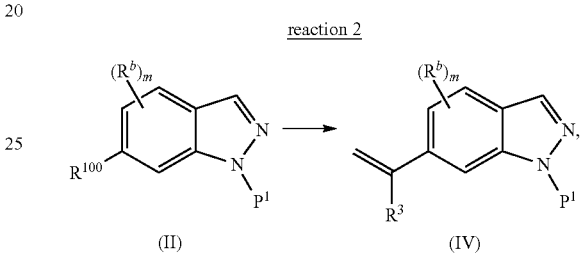

reaction 2

(II)          (IV)

wherein values and particular values for the variables are as described above for reaction 1 or Structural Formula (A).

In one embodiment, for reaction 2, $R^{100}$ is —Br and the vinyl indazole compound of Structural Formula (IV) is prepared by a Suzuki coupling reaction, whereby the N1-substituted indazole of Structural Formula (II) is reacted with a vinyl boronate ester (e.g., vinylboronic acid pinacol ester or 4,4,6-trimethyl-2-vinyl-1,3,2-dioxaborinane) or vinyl borate salt (e.g., potassium vinyltrifluoroborate) in the presence of a palladium catalyst. Exemplary palladium catalyst includes, but is not limited to, a pre-formed ligand metal complex such as Pd(PPh$_3$)$_4$, PdCl$_2$(dppf)$_2$, PdCl$_2$(PPh$_3$)$_2$, or a mixture of metal salts such as Pd(OAc)$_2$, PdCl$_2$, or Pd$_2$(dba)$_3$ with added phosphine ligands, for example PPh$_3$, PCy$_3$, or dppf. The reaction is carried out in a suitable solvent, such as ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane), alcohol solvents (e.g., methanol, ethanol, isopropanol), dimethylformamide, dimethyl sulfoxide, acetonitrile, or mixtures of such solvents, with water as an optional co-solvent. A suitable base, such as alkali metal $C_{1-6}$ alkoxide (e.g., NaOMe, KO$^t$Bu), alkali metal hydroxide (e.g., NaOH, KOH), alkali metal carbonate (e.g., Na$_2$CO$_3$, K$_2$CO$_3$ or Cs$_2$CO$_3$), amine (e.g., ethylamine, propylamine, dimethylamine, trimethylamine, triethylamine, isopropyethylamine or diisopropyethylamine), alkali metal fluoride (e.g., NaF or KF), or alkali metal phosphate (e.g., Na$_3$PO$_4$, Na$_2$HPO$_4$, NaH$_2$PO$_4$, K$_2$HPO$_4$, KH$_2$PO$_4$ or K$_3$PO$_4$) can be used for reaction 2 described in any one of the foregoing embodiments. Alternatively, a base selected from the group consisting of NaOH, KOH, K$_2$CO$_3$, Na$_2$CO$_3$, Cs$_2$CO$_3$, KO$^t$Bu, KF, K$_3$PO$_4$ and Et$_3$N, can be used for reaction 2 described in any one of the foregoing embodiments. In one embodiment, $R^3$ is —H.

Alternatively, for reaction 2, when $R^{100}$ is —C(=O)$R^3$, the vinyl indazole compound of Structural Formula (IV) is prepared by reacting the N1-substituted indazole compound of Structural Formula (II) with a Wittig reagent, such as MePPh$_3$Br, in the presence of a strong base, such as NaH, KO$^t$Bu or BuLi, in a solvent, such as THF, DMF or DMSO. In one embodiment, $R^3$ is —H.

The present invention is directed to a method of preparing a diol compound represented by Structural Formula (V) comprising the step of reacting the vinyl indazole compound of Structural Formula (IV) with a dihydroxylation reagent (reaction 3) in the presence of a solvent:

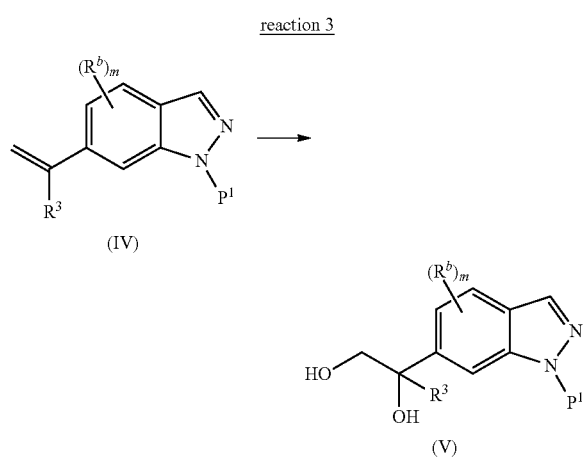

wherein values and alternative values are as described above for reaction 2.

As used herein, a "dihydroxylation reagent" is a compound that converts an alkene to a vicinal diol compound. Exemplary dihydroxylation reagent includes KMnO$_4$ and OsO$_4$ with an oxidant such as N-methylmorpholine-N-oxide (NMO).

In one embodiment, for reaction 3, the diol compound is represented by Structural Formula (Va):

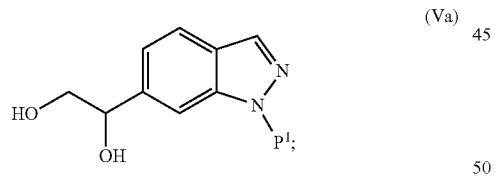

and the vinyl indazole compound is represented by Structural Formula (IVa):

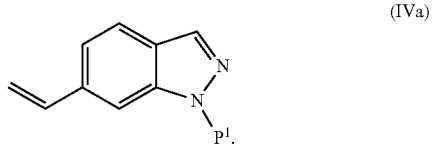

In another embodiment, for reaction 3, the diol compound is represented by Structural Formula (Vb) and the dihydroxylation of the vinyl indazole compound of Structural Formula (IVa) is carried out in the presence of a chiral inducing agent (reaction 3a).

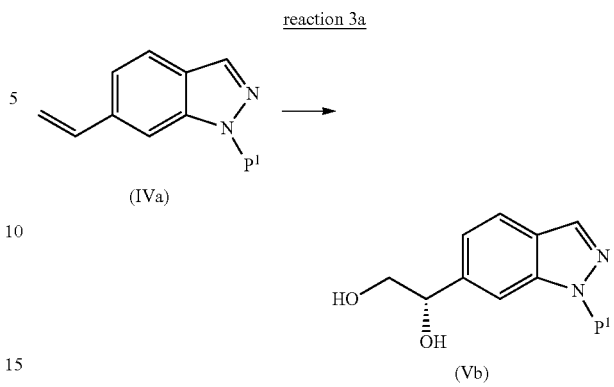

As used herein, a "chiral inducing agent" is a compound that is used to create stereoselectivity at a chiral center.

Any suitable chiral inducing agent can be used in reactions 3a and 3b. Exemplary chiral inducing agent includes (DHQ)$_2$PHAL, Q$_2$(PHAL) or AD-mix-α. In one embodiment, at least 70%, 80%, 90%, 95%, 96%, 97%, 98%, 99%, 99.5%, 99.8%, 99.9% or 100% by weight of the diol compound obtained by reaction 3a is represented by Structural Formula (Vb).

In another embodiment, for reaction 3, the diol compound is represented by Structural Formula (Vc) and the dihydroxylation of the vinyl indazole compound of Structural Formula (IVa) is carried out in the presence of a chiral inducing agent (reaction 3b).

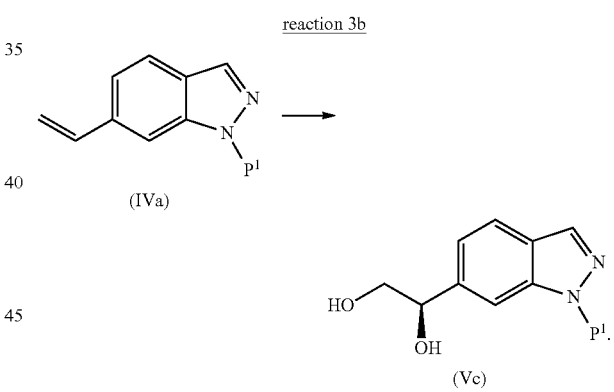

Any suitable chiral inducing agent can be used. Exemplary inducing agent includes (DHQD)$_2$PHAL or AD-mix-β. In one embodiment, at least 70%, 80%, 90%, 95%, 96%, 97%, 98%, 99%, 99.5%, 99.8%, 99.9% or 100% by weight of the diol compound obtained by reaction 3b is represented by Structural Formula (Vc).

In one embodiment, for reactions 3, 3a and 3b described above, the dihydroxylation reagent comprises an osmium reagent and an oxidant. Exemplary osminum reagent includes OsO$_4$ or potassium osmate (e.g., K$_2$OsO$_4$.2H$_2$O). Exemplary oxidant includes t-BuOOH, N-methylmorpholine-N-oxide (NMO) and K$_3$Fe(CN)$_6$. The dihydroxylation can be carried out in the presence of a base. Suitable base can be used includes, for example, an alkali carbonate, an alkali hydroxide, an amine and an ammonium hydroxide. Particularly, the base is selected from the group consisting of K$_2$CO$_3$, Na$_2$CO$_3$, NaOH and KOH. More particularly, the base is K$_2$CO$_3$. Alternatively, the dihydroxylation can be carried out in the presence of an acid. Suitable acid includes, for example, citric acid or acetic acid.

In one embodiment, the dihydroxylation reaction described in any one of the foregoing embodiments is carried out in a mixture of water and an organic solvent. Suitable organic solvent includes, for example, methanol, ethanol, 1-propanol, 2-propanol, 1-butanol, tBuOH, acetone, acetonitrile or toluene.

In one embodiment, the dihydroxylation reaction described in any one of the foregoing embodiments is carried out at a temperature ranging from 0° C. to 50° C. Alternatively, the dihydroxylation reaction described above is carried out at a temperature ranging from 0° C. to room temperature.

The present invention is also directed to a method of preparing an indazole compound represented by Structural Formula (VI) comprising reacting the diol compound represented by Structural Formula (V) with a sulfonation reagent or a halogenation reagent (reaction 4):

reaction 4

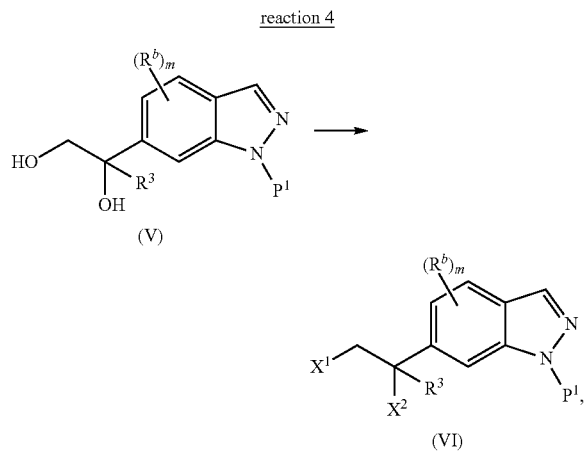

wherein $X_1$ and $X_2$ are independently a sulfonate leaving group or a halide; and values and alternative values for the remainder of the variables are as described above for reaction 3.

A "sulfonate leaving group" is a sulfonate moiety that can easily be displaced by a nucleophile. Sulfonate leaving groups are well known in the art and are described, for example, in March, "Advanced Organic Chemistry—Reactions, Mechanisms and Structure", $5^{th}$ Edition, John Wiley & Sons, 2001. In one embodiment, the sulfonate leaving group is represented by —OSO$_2$R", wherein R" is $C_{1-6}$ alkyl, $C_{1-6}$ haloalkyl, or phenyl optionally substituted one or more substituents independently selected from the group consisting of halogen, nitro, $C_{1-6}$ alkyl, $C_{1-6}$ haloalkyl, $C_{1-6}$ alkoxy and $C_{1-6}$ haloalkoxy. Exemplary sulfonate leaving groups include, but are not limited to, methanesulfonate, benzylsulfonate and tosylate.

As used herein, a "sulfonation reagent" is a compound that can convert an alcohol functional group into a sulfonate group. Typical sulfonation reagent includes the appropriate sulfonic acid chloride.

As used herein, a "halogenation reagent" is a compound that can convert an alcohol functional group into a halide group. Exemplary halogenation reagents include, but are not limited to, HCl, HBr, HI, SOCl$_2$ and PBr$_3$. Alternatively, the alcohol containing compound is converted to an intermediate compound with —OH group being replaced with a leaving group, such as a sulfonate leaving group. The intermediate compound then reacts with a halogenation reagent to form a halogenated compound.

In one embodiment, for reaction 4 described above, the indazole compound of Structural Formula (VI) is represented by Structural Formula (VIa):

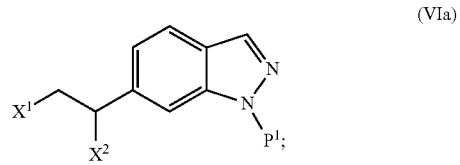

And the diol compound is represented by Structural Formula (Va) described above.

In another embodiment, for reaction 4 described above, the indazole compound is represented by Structural Formula (VIb):

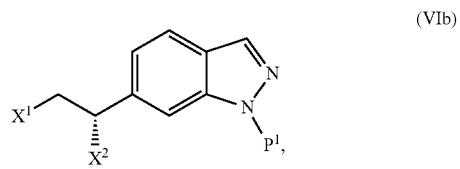

and the diol compound is represented by Structural Formula (Vb) described above. In one embodiment, at least 70%, 80%, 90%, 95%, 96%, 97%, 98%, 99%, 99.5%, 99.8%, 99.9% or 100% by weight of the indazole compound obtained by reaction 4 is represented by Structural Formula (VIb).

Alternatively, for reaction 4, the indazole compound is represented by Structural Formula (VIc):

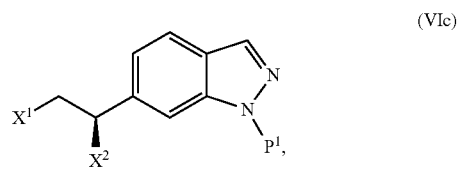

and the diol compound is represented by Structural Formula (Vc) described above. In one embodiment, at least 70%, 80%, 90%, 95%, 96%, 97%, 98%, 99%, 99.5%, 99.8%, 99.9% or 100% by weight of the indazole compound obtained by reaction 4 is represented by Structural Formula (VIc).

In one embodiment, for reaction 4 described in any one of the foregoing embodiments, $X^1$ and $X^2$ are —OSO$_2$R", wherein R" is $C_{1-6}$ alkyl, $C_{1-6}$ haloalkyl, or phenyl optionally substituted one or more substituents independently selected from the group consisting of halogen, nitro, $C_{1-6}$ alkyl, $C_{1-6}$ haloalkyl, $C_{1-6}$ alkoxy and $C_{1-6}$ haloalkoxy. In one embodiment, R" is methyl, benzyl or tosyl. The indazole compound of Structural Formula (VI) can be prepared by reacting the diol compound of Structural Formula (V) with R"SO$_2$Cl in the presence of a base. Suitable base includes, but is not limited to, a tertiary amine (e.g., Et$_3$N, $^i$Pr$_2$NEt or pyridine) and alkali metal hydroxide (e.g., NaOH or KOH).

In another embodiment, reaction 4 described in any one of the foregoing embodiments is carried out in an organic solvent, such as ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane), alcohol solvents (e.g., methanol, ethanol, isopropanol), dimethylformamide, dimethyl sulfoxide and acetonitrile.

The present invention is also directed to a method of preparing a N-substituted indolinone compound represented by Structural Formula (X) comprising: a) converting an isatin compound represented by Structural Formula (VII) to an intermediate compound represented by Structural Formula (VIII); and b) reacting the intermediate compound with an excess of hydrazine $N_2H_4$ (reaction 5):

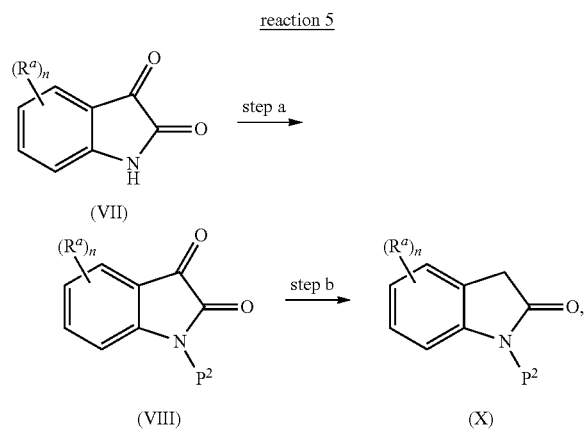

wherein $P^2$ is $R^4$ or a nitrogen protecting group and $R^4$, $R^a$ and n are as described above for Structural Formula (A) and the nitrogen protecting reagent is as described above for reaction 1.

In one embodiment, for reaction 5, the isatin compound is represented by Structural Formula (VIIa):

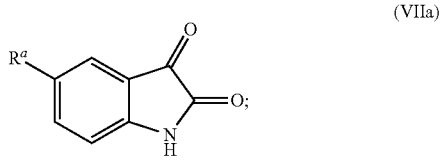

the intermediate compound is represented by Structural Formula (VIIIa):

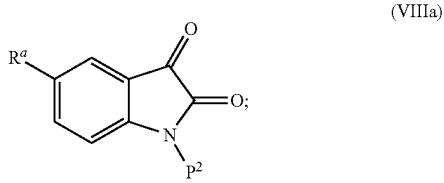

and the N-substituted indolinone compound is represented by Structural Formula (Xa):

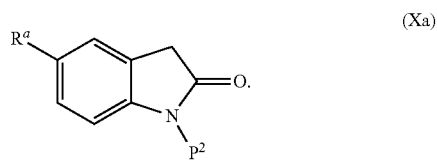

In one embodiment, for reaction 5 described in any one of foregoing embodiments, $P^2$ is a nitrogen protecting group described above for reaction 1 and the $P^2$ group can be installed on isatin nitrogen atom using known procedures in the art including those described in T. W. Greene, Protecting Groups in Organic Synthesis, John Wiley & Sons, Inc. 1981, the entire teachings of which are incorporated herein by reference.

In another embodiment, for reaction 5 described in any one of foregoing embodiments, the nitrogen protecting group represented by $P^2$ is —C(=O)O—$R^P$, —$SO_2$—$R^P$ or benzyl optionally substituted one or more (e.g., 2, 3 or 4) substituents independently selected from the group consisting of halogen, nitro, $C_{1-6}$ alkyl, $C_{1-6}$ haloalkyl, $C_{1-6}$ alkoxy, $C_{1-6}$ haloalkoxy and ($C_{1-6}$ alkoxy)$C_{1-6}$ alkyl; and $R^P$ is $C_{1-6}$ alkyl, $C_{1-6}$ haloalkyl, —$C_{1-6}$ alkylene-Si($C_{1-6}$ alkyl)$_3$, phenyl optionally substituted with one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy and ($C_{1-6}$ alkoxy)$C_{1-6}$ alkyl.

In another embodiment, for reaction 5 described in any one of foregoing embodiments, $P^2$ is a $C_{1-6}$ alkyl or a benzyl group, and the intermediate compound of Structural Formula (VIII) is prepared by reacting the isatin compound of Structural Formula (VII) with an alkylating reagent, wherein the benzyl group represented by $P^2$ is optionally substituted with one or more (e.g., 2, 3 or 4) substituents independently selected from the group consisting of halogen, nitro, $C_{1-6}$ alkyl, $C_{1-6}$ haloalkyl, $C_{1-6}$ alkoxy, $C_{1-6}$ haloalkoxy and ($C_{1-6}$ alkoxy)$C_{1-6}$ alkyl; and the $C_{1-6}$ alkyl group represented by $P^2$ is optionally substituted with one or more substituents selected from the group consisting of halogen, hydroxy, nitro, cyano, amino, —C(O)$NH_2$, phenyl, 5-6 membered heteroaryl, $C_{1-6}$ alkoxy, $C_{1-6}$ alkylamino, $C_{1-6}$ dialkylamino and $C_{1-6}$ haloalkoxy.

An "alkylating reagent" is a compound represented by structural formula $P^2X$, wherein X is halogen (e.g., —Br, —I or —Cl). In one embodiment, the alkylating agent is selected from benzyl bromide, iodomethane or 1-bromo-2-methoxyethane.

In one embodiment, for reaction 5 described in any one of the foregoing embodiments, the base can be used in the alkylation reaction includes an alkali metal hydride (e.g., sodium hydride, potassium hydride or lithium hydride), an alkali metal hydroxide (e.g., NaOH or KOH), an alkali metal $C_{1-6}$ alkoxide (e.g., NaOMe, KOMe, NaO$^t$Bu or KO$^t$Bu), and an alkali metal carbonate (e.g., $Na_2CO_3$ or $K_2CO_3$). The alkylation reaction can be carried out in an organic solvent. Exemplary organic solvent includes, but is not limited to, ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane).

In one embodiment, for reaction 5 step b) described in any one of the foregoing embodiments, the intermediate compound is reacted with excess hydrazine (e.g., 10-20 equiv., 5-10 equiv., or 2-2.5 equiv.) at an elevated temperature, for example, from 120-140° C. Alternatively, the intermediate compound is reacted with 2-2.5 equiv. of hydrazine hydrate at a temperature from 120-140° C. The reaction of the intermediate compound and hydrazine can be carried out without any solvent or in an organic solvent, such as DMSO.

Alternatively, the N-substituted indolinone compound of Structural Formula (X) can be prepared by alkylating an oxindole compound represented by Structural Formula (IX) with an alkylating reagent in the presence of a base (reaction 6):

reaction 6

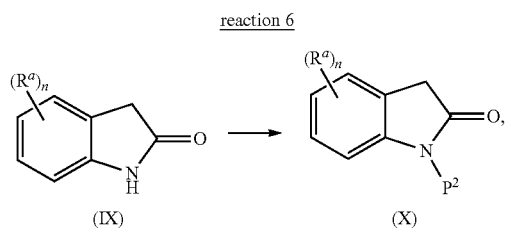

(IX)            (X)

wherein $R^a$, n and $P^2$ are as described above for reaction 5.

In one embodiment, the oxindole compound in reaction 6 is represented by Structural Formula (IXa)

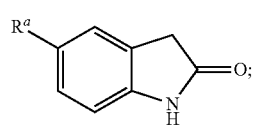

(IXa)

and the N-substituted indolinone compound is represented by Structural Formula (Xa) described above for reaction 5.

The alkylating reagent that can be used in reaction 6 described in any one of the foregoing embodiments is as described above for reaction 5. Alternatively, the alkylating reagent is dimethyl sulfate and the alkylation reaction is carried out in a non-polar solvent, such as toluene, at an elevated temperature, for example, 60-100° C.

The present invention is also directed to a method (reaction 7) of preparing a spiro indolinone compound represented by Structural Formula (XI'), or salt thereof, comprising the step of reacting an indolinone compound represented by Structural Formula (X) with a base and an indazole compound represented by Structural Formula (VI'):

reaction 7

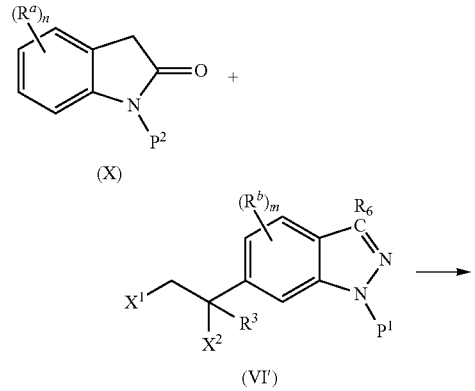

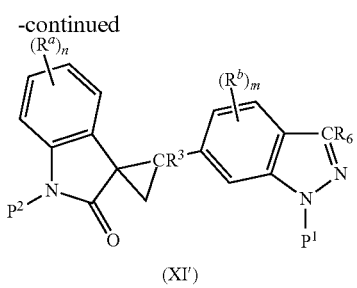

(XI')

In another embodiment, the present invention is also directed to a method (reaction 7a) of preparing a spiro indolinone compound represented by Structural Formula (XI), or salt thereof, comprising the step of reacting an indolinone compound represented by Structural Formula (X) with a base and an indazole compound represented by Structural Formula (VI):

reaction 7a

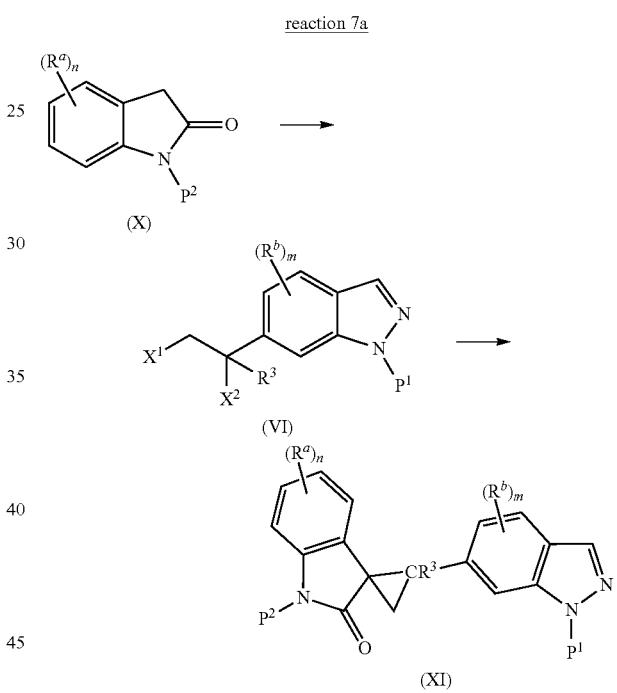

(X)

(VI)

(XI)

In another embodiment, for reaction 7a, the spiro indolinone compound is represented by Structural Formula (XIa):

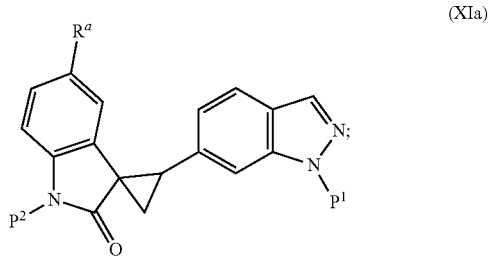

(XIa)

the indolinone compound is represented by Structural Formula (Xa); and the and the indazole compound is represented by Structural Formula (VIa):

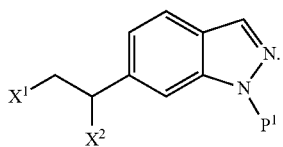
(VIa)

In yet another embodiment, for reaction 7a, the spiro indolinone compound is represented by Structural Formula (XIb):

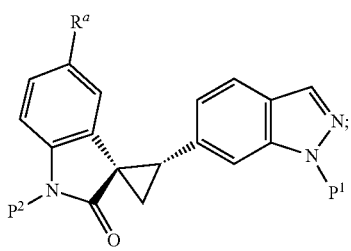
(XIb)

the indolinone compound is represented by Structural Formula (Xa); and the and the indazole compound is represented by Structural Formula (VIb):

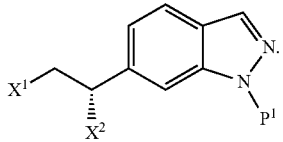
(VIb)

In yet another embodiment, for reaction 7a, the spiro indolinone compound is represented by Structural Formula (XIc):

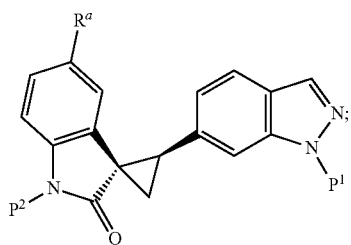
(XIc)

the indolinone compound is represented by Structural Formula (Xa); and the and the indazole compound is represented by Structural Formula (VIc):

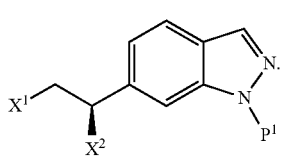
(VIc)

In another embodiment, for reaction 7 or 7a described in any one of the foregoing embodiments, $X^1$ and $X^2$ are —$OSO_2R''$, wherein R" is $C_{1-6}$ alkyl, $C_{1-6}$ haloalkyl, or phenyl optionally substituted one or more substituents independently selected from the group consisting of halogen, nitro, $C_{1-6}$ alkyl, $C_{1-6}$ haloalkyl, $C_{1-6}$ alkoxy and $C_{1-6}$ haloalkoxy. Alternatively, $X^1$ and $X^2$ are —$OSO_2Me$.

In another embodiment, for reaction 7 or 7a described in any one of the foregoing embodiments, the base is an alkali metal hydride, an alkali metal amide, an alkali metal hydroxide, an alkyl alkali metal, an aryl alkali metal or an alkali metal $C_{1-6}$ alkoxide. Alternatively, the base is an alkali metal hydride. In another alternative, the base is sodium hydride, potassium hydride, calcium hydride or lithium hydride. In another alternative, the base is sodium hydride.

In another embodiment, for reaction 7 or 7a described in any one of the foregoing embodiments, the reaction is carried out in a solvent. In one embodiment, the solvent is an anhydrous aprotic organic solvent. Exemplary aprotic organic solvent includes, but is not limited to, tetrahydrofuran, diethylether, dimethoxyethane, toluene, methylene chloride, dimethyl formamide, dimethyl sulfoxide, acetonitrile, dioxane, methyl tert-butyl ether, 1,2-dichloroethane, or a combination thereof.

In another embodiment, for reaction 7 or 7a described in any one of the foregoing embodiments, $P^1$ is —C(=O)O—$R^P$, —$SO_2$—$R^P$ or benzyl optionally substituted one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy and ($C_{1-6}$ alkoxy)$C_{1-6}$ alkyl;

$P^2$ is $C_{1-6}$ alkyl, $C_{1-6}$ haloalkyl, ($C_{1-6}$ alkoxy)$C_{1-6}$ alkyl, —C(=O)O—$R^P$, —$SO_2$—$R^P$, tetrahydro-2H-pyran-2-yl or benzyl optionally substituted one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl; and $R^P$ is $C_{1-6}$ alkyl, $C_{1-6}$ haloalkyl, —$C_{1-6}$ alkylene-Si($C_{1-6}$ alkyl)$_3$, phenyl optionally substituted with one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy and ($C_{1-6}$ alkoxy)$C_{1-6}$ alkyl. Alternatively, R" is methyl; $P^1$ is benzyl or p-methoxybenzyl; and $P^2$ is methyl, —$CH_2CH_2OMe$, benzyl or p-methoxybenzyl.

In another embodiment, for reaction 7 or 7a described in any one of the foregoing embodiments:

each $R^a$ is independently —H, halogen, cyano, —$NR^1R^2$, —$NR^2C(O)R^1$, —$C(O)OR^1$, —$OC(O)R^1$, —$C(O)NR^1R^2$, —$NR^2C(O)OR^1$, —$N(R^2)C(O)NR^1R^2$, —$OR^1$, —$SO_2NR^1R^2$, —$NR^2SO_2R^1$, $C_{1-6}$ alkyl, phenyl or 5-12 membered heteroaryl, wherein 5-12 membered heteroaryl represented by $R^a$ is selected from the group consisting of pyridyl, thiazolyl, pyrazinyl, thiophenyl, indolyl, quinolinyl, pyrrolyl, pyrazolyl, and pyrimidinyl; the $C_{1-6}$ alkyl represented by $R^a$ is optionally substituted with one or more substituents selected from the group consisting of halogen, nitro, cyano, —OH, —SH, —O($C_{1-6}$ alkyl), —S($C_{1-6}$ alkyl), $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl; and the phenyl or the 5-12 membered heteroaryl represented by $R^a$ is optionally substituted with one or more substituents selected from the group consisting of halogen, nitro, cyano, —OH, —SH, —O($C_{1-6}$ alkyl), —S($C_{1-6}$ alkyl), $C_{11}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl and $C_{1-6}$ alkylcarbonyl;

each $R^1$ is independently —H or $C_{1-6}$ alkyl, wherein the $C_{1-6}$ alkyl is optionally substituted with one or more substituents independently selected from the group consisting of halogen, —OH, —SH, —O($C_{1-3}$ alkyl), —S($C_{1-3}$ alkyl) and $C_{1-6}$ haloalkoxy; and each $R^2$ is independently —H or $C_{1-6}$ alkyl.

Alternatively, $R^a$ is —H, halogen, $C_{1-3}$ alkyl or $C_{1-3}$ alkoxy. In another alternative, $R^a$ is —H, —F, methyl, ethyl or methoxy.

The present invention is also directed to a method (reaction 8) of preparing an halogenated indolinone compound represented by Structural Formula (XIIIA), or a salt thereof, comprising the step of halogenating an indazole compound represented by Structural Formula (XII) with a halogenating reagent:

reaction 8

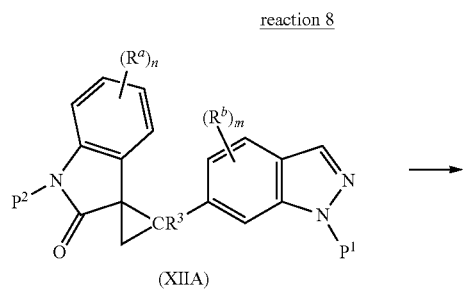

(XIIA)

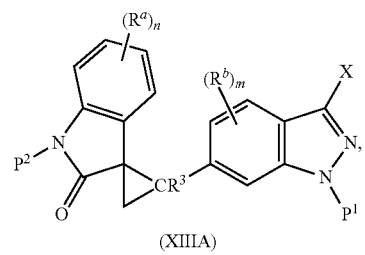

(XIIIA)

Wherein X is halogen, $R^{102}$ is —H or $P^1$; $P^1$ is a nitrogen protecting group; $P^2$ is $R^4$ or a nitrogen protecting group and values and alternative values for the remainder of the variables are as described above for reaction 7.

As used herein, a "halogenating reagent" is a compound that can react with a molecule having an electron-rich functional group such as alkene, aromatic ring or heteroaromatic ring to incorporate a halogen atom into the molecule. Exemplary halogenating reagent includes, but is not limited to HBr, HF, HI, $I_2$, N-iodosuccinimide, bromine and N-bromosuccinimide.

In one embodiment, for reaction 8, the halogenated indolinone compound is represented by the following Structural Formula:

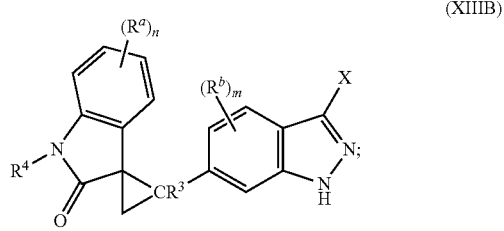

(XIIIB)

or a salt thereof, and the indazole compound is represented by the following Structural Formula:

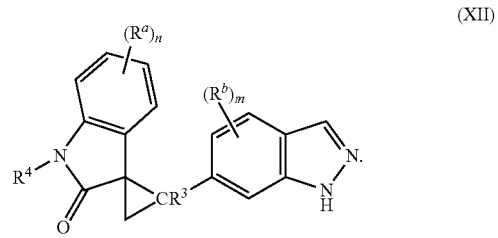

(XII)

In one embodiment, for reaction 8 described in any one of the foregoing embodiments, X is —I or —Br. The halogenating reagent is selected from iodine, N-iodosuccinimide, bromine and N-bromosuccinimide.

In another embodiment, for reaction 8, X is —I, the halogenated indolinone compound is an iodinated indolinone compound represented by Structural Formula (XIII), or a salt thereof, the indazole compound is represented by Structural Formula (XII) (reaction 8a); and the halogenating reagent is an iodinating reagent:

reaction 8a

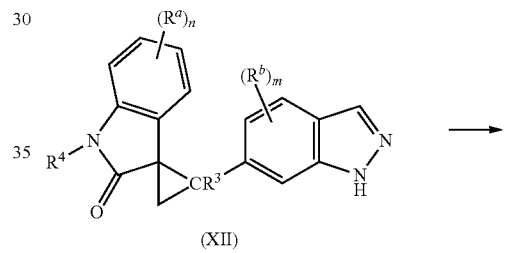

(XII)

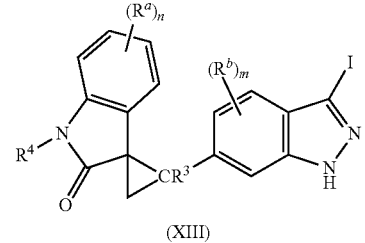

(XIII)

In one embodiment, for reaction 8a, the iodinated indolinone compound is represented by the following Structural Formula:

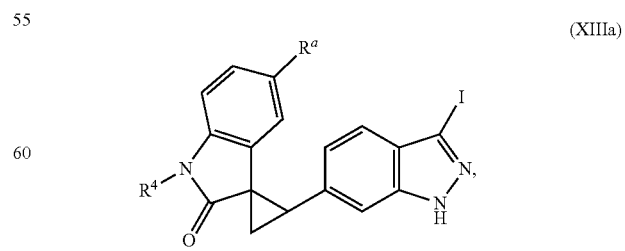

(XIIIa)

or a salt thereof, and the deprotected indazole compound is represented by the following Structural Formula:

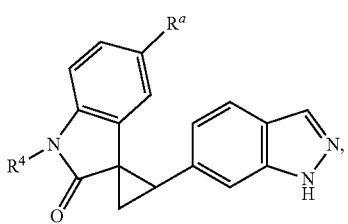

(XIIa)

In another embodiment, for reaction 8a, the iodinated indolinone compound is represented by the following Structural Formula:

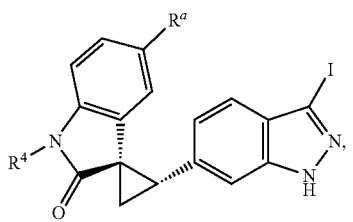

(XIIIb)

or a salt thereof, and the deprotected indazole compound is represented by the following Structural Formula:

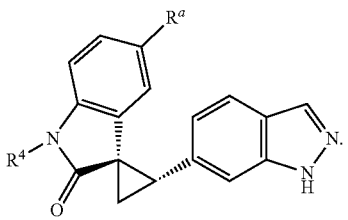

(XIIb)

In yet another embodiment, for reaction 8a, the iodinated indolinone compound is represented by the following Structural Formula:

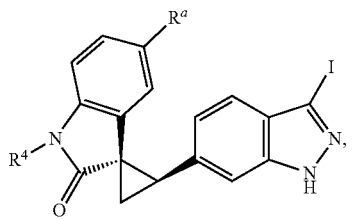

(XIIIc)

or a salt thereof, and the deprotected indazole compound is represented by the following Structural Formula:

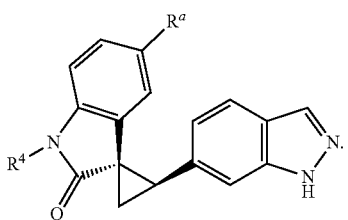

(XIIc)

An "iodinating reagent" is a compound that can react with a molecule having an electron-rich functional group such as alkene, aromatic ring or heteroaromatic ring to incorporate an iodine atom into the molecule.

In one embodiment, for reaction 8a described in any one of the foregoing embodiments, the iodinating agent is iodine or N-iodosuccinimide.

In another embodiment, for reaction 8 or 8a described in any one of the foregoing embodiments, the halogenation (or iodination) is carried out in the presence of a base. Suitable base can be used in the halogenation (or iodination) reaction includes alkali metal carbonate, alkali metal hydroxide and alkali metal $C_{1-6}$ alkoxide. Alternatively, the base is selected from the group consisting of $Na_2CO_3$, $K_2CO_3$, NaOH, KOH, NaOMe, and KO$^t$Bu.

In another embodiment, for reaction 8 or 8a described in any one of the foregoing embodiments, the halogenation (or iodination) reaction is carried out in a solvent. In one embodiment, the solvent is an organic solvent or a mixture of an organic solvent and water. Exemplary organic solvent includes, but is not limited to acetonitrile, DMF, DMSO, dioxane, NMP, THF.

In another embodiment, for reaction 8 or 8a described in any one of the foregoing embodiments, the indazole compound represented by Structural Formula (XII) is prepared by deprotecting a protected indazole compound represented by Structural Formula or (XI) (reaction 9a) described below:

reaction 9a

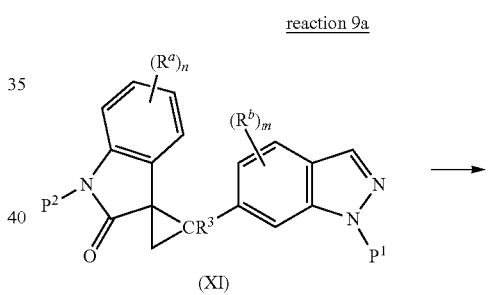

(XI)

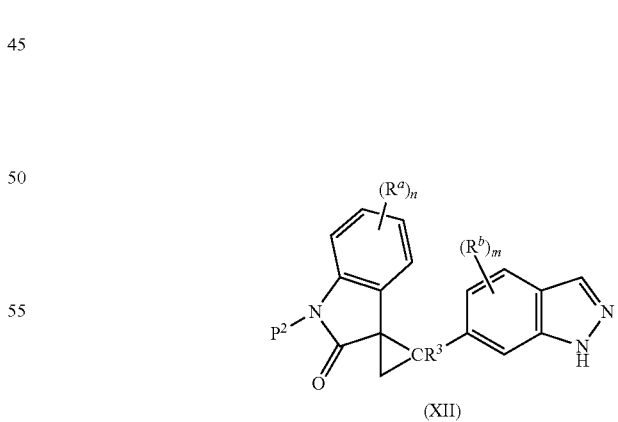

(XII)

wherein $P^1$ is a nitrogen protecting group; $P^2$ is $R^4$ or a nitrogen protecting group; and the remainder of the variables are as described above for Structural Formula (A).

In one embodiment, for reaction 9a, the protected indazole compound is represented by Structural Formula (XIa):

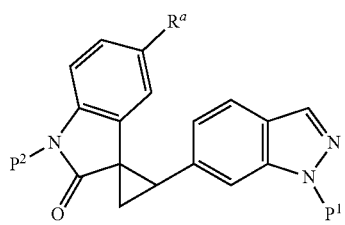

(XIa)

and the indazole compound is represented by Structural Formula (XIIa) described above for reaction 8.

Alternatively, for reaction 9a, the protected indazole compound is represented by Structural Formula (XIb):

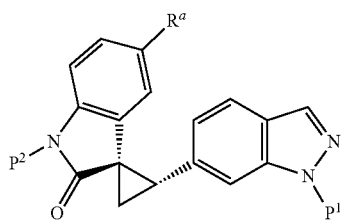

(XIb)

and the indazole compound is represented by Structural Formula (XIIb) described above for reaction 8.

In another alternative, for reaction 9a, the protected indazole compound is represented by Structural Formula (XIc):

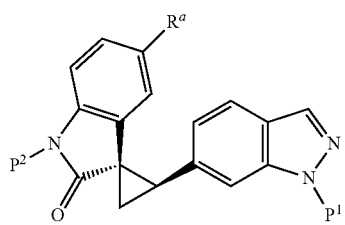

(XIc)

and the indazole compound is represented by Structural Formula (XIIc) described above for reaction 8.

In another embodiment, the present invention is directed to a method (reaction 9) of preparing a deprotected indazole compound represented by Structural Formula (XII') comprising deprotecting an indazole compound represented by Structural Formula (XI'):

reaction 9

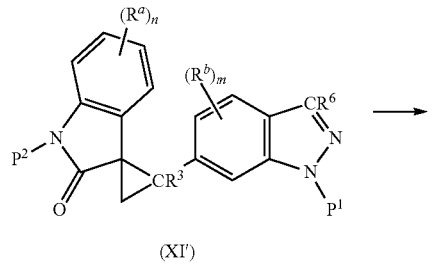

(XI')

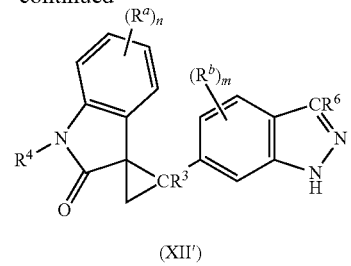

(XII')

wherein $R^6$ is as described for Structural Formula (A) and values and alternative values for the remainder of the variables are as described above for reaction 9a. In one embodiment, $R^6$ is —H or —I.

In one embodiment, for reaction 8, reaction 9 or reaction 9a described in any one of foregoing embodiments:

$P^1$, when present, is —C(=O)O—$R^P$, —SO$_2$—$R^P$ or benzyl optionally substituted one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy and ($C_{1-6}$ alkoxy)$C_{1-6}$ alkyl;

$P^2$ is $C_{1-6}$ alkyl, $C_{1-6}$ haloalkyl, ($C_{1-6}$ alkoxy)$C_{1-6}$ alkyl, —C(=O)O—$R^P$, —SO$_2$—$R^P$ or benzyl optionally substituted one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl; and $R^P$ is $C_{1-6}$ alkyl, $C_{1-6}$ haloalkyl, —$C_{1-6}$ alkylene-Si($C_{1-6}$ alkyl)$_3$, phenyl optionally substituted with one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy and ($C_{1-6}$ alkoxy)$C_{1-6}$ alkyl.

In another embodiment, for reaction 8, reaction 9 or reaction 9a described in any one of the foregoing embodiments, $P^1$, when present, is benzyl or p-methoxybenzyl; and $P^2$ is methyl, —CH$_2$CH$_2$OMe, benzyl or p-methoxybenzyl.

In another embodiment, for reaction 9 or reaction 9a described in any one of the foregoing embodiments, the deprotection reaction is carried out in the presence of a base (e.g., KO$^t$Bu or $^t$BuLi) and an oxygen donor (e.g., O$_2$, MoOPH or MoOPD). Alternatively, the deprotection reaction is carried out in the presence of an acid. Exemplary acid includes, but is not limited, TFA, TfOH or a mixture thereof.

The present invention is also directed to a method (reaction 10) for preparing an spiro cyclopropyl indolinone compound represented Structural Formula (A) comprising reacting the halogenated indolinone compound represented by Structural Formula (XIIIB) with $R^6B(OH)_2$ or a boronic ester derivative thereof in the presence of a palladium catalyst (Suzuki coupling reaction), reaction 10

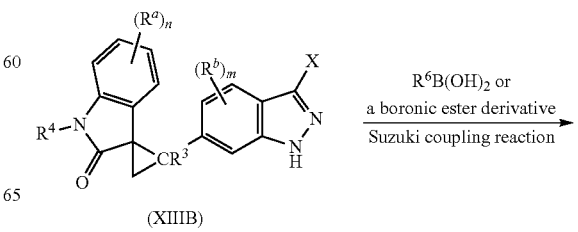

(XIIIB)

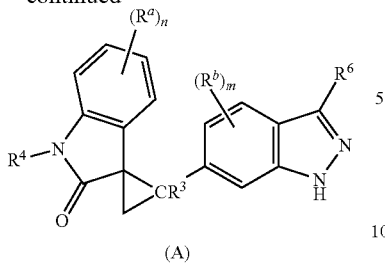

(A)

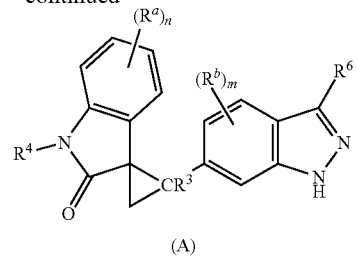

(A)

wherein $R_6$ is $C_{2-10}$ alkenyl, phenyl, 5-12 membered heteroaryl or 9-12 membered heterocyclyl group, wherein the $C_{2-10}$ alkenyl group represented by $R^6$ is optionally substituted with one or more substituents selected from the group consisting of halogen, hydroxy, nitro, cyano, amino, phenyl, 5-12 membered heteroaryl, 9-12 membered heterocyclyl group, $C_1$-$C_6$ alkoxy, $C_1$-$C_6$ haloalkoxy, $C_{1-6}$ alkylamino, $C_{1-6}$ dialkylamino, —C(O)H, —C(O)($C_1$-$C_6$ alkyl), —C(O)($C_1$-$C_6$ haloalkyl), —C(O)(phenyl), —C(O)(non-aromatic heterocyclic group), —C(O)O(C1-C6 alkyl), —C(O)O(C1-C6 haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl) and —S(O)$_2$(phenyl), and wherein each of the phenyl, heteroaryl and heterocyclyl groups represented by $R^6$, and the phenyl, heteroaryl and heterocyclyl groups in the substituents for the aliphatic group represented by $R^6$ independently are optionally substituted with one or more substituents selected from the group consisting of halogen, —OH, —SH, nitro, cyano, amino, $C_{1-6}$ alkylamino, $C_{1-6}$ dialkylamino, ($C_{1-6}$ dialkylamino)$C_{1-6}$ dialkylamino, $C_1$-$C_6$ alkyl, $C_1$-$C_6$ haloalkyl, —O($C_{1-6}$ alkyl), —O-(non-aromatic heterocyclic group), —S($C_{1-6}$ alkyl), —O($C_{1-6}$ haloalkyl), ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, ($C_{1-6}$ dialkylamino)$C_{1-6}$ alkoxy, (phenyl)$C_{0-6}$ alkyl, (5-6 membered heteroaryl)$C_{1-6}$ alkyl, (non-aromatic heterocyclic group)$C_{1-6}$ alkyl (optionally substituted with halogen, —OH, $C_{1-6}$ alkyl, ($C_{1-6}$ alkoxy)$C_{1-6}$ alkyl, $C_{1-6}$ acyl, alkylamino, dialkylamino or non-aromatic heterocyclic group), (5-6 membered heteroaryl)$C_{1-6}$ alkoxy, (non-aromatic heterocyclic group)$C_{1-6}$ alkoxy, —C(O)($C_1$-$C_6$ alkyl), —C(O)($C_1$-$C_6$ haloalkyl), —C(O)(phenyl), —C(O)(non-aromatic heterocyclic group), —C(O)O($C_1$-$C_6$ alkyl), —C(O)O($C_1$-$C_6$ haloalkyl), —C(O)O(phenyl), —OC(O)($C_1$-$C_6$ alkyl), —OC(O)($C_1$-$C_6$ haloalkyl), —OC(O)(phenyl), —S(O)$_2$NH$_2$, —S(O)$_2$($C_1$-$C_6$ alkyl), —S(O)$_2$($C_{1-6}$ haloalkyl), and —S(O)$_2$(phenyl).

In one embodiment, for reaction 10, the halogenated indolinone compound is represented by Structural Formula (XIII) (reaction 10a):

reaction 10a

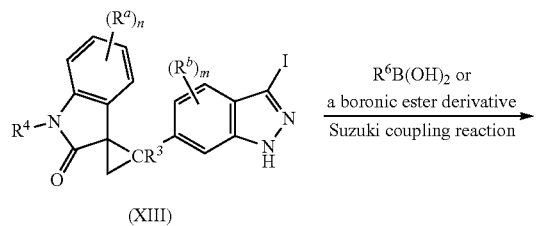

(XIII)

$R^6B(OH)_2$ or a boronic ester derivative Suzuki coupling reaction

A boronic ester derivative of $R^6B(OH)_2$ is represented by $R^6B(Y^1)(Y^2)$, wherein $Y^1$ and $Y^2$ are each independently a $C_{1-6}$ alkoxy or aryloxy (e.g., phenoxy group optionally substituted with one or more (e.g., 2, 3 or 4) substituents selected from the group consisting of halogen, —NO$_2$, —CN, $C_{1-3}$ alkyl, $C_{1-3}$ haloalkyl, $C_{1-3}$ alkoxy and ($C_{1-3}$ alkoxy)$C_{1-3}$ alkyl) or $Y^1$ and $Y^2$ together form a moiety derived from dihydroxy compound separated by $C_{2-6}$ alkylene group, which is optionally substituted with 1 to 4 substituents independently selected from $C_{1-3}$ alkyl, $C_{1-3}$ haloalkyl, $C_{1-3}$ alkoxy and ($C_{1-3}$ alkoxy)$C_{1-3}$ alkyl. In one embodiment, $R^6B(Y^1)(Y^2)$ is represented by the following structural formula:

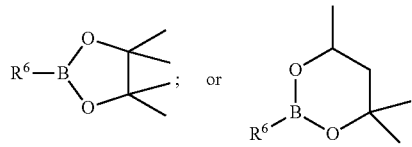

Suitable Suzuki coupling reaction conditions and Suzuki catalysts are known in the art and can be used to carry out reaction 10 or reaction 10a. The reaction is preferably effected under microwave irradiation conditions, advantageously in the range, for example of 100 to 150° C., or generally at about 120° C. Exemplary palladium catalyst includes, but is not limited to, a pre-formed ligand metal complex such as Pd(PPh$_3$)$_4$, PdCl$_2$(dppf)$_2$, PdCl$_2$(PPh$_3$)$_2$, or a mixture of metal salts such as Pd(OAc)$_2$, PdCl$_2$, or Pd$_2$(dba)$_3$ with added phosphine ligands, for example PPh$_3$, PCy$_3$, or dppf. The reaction is carried out in a suitable solvent, such as ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane), alcohol solvents (e.g., methanol, ethanol, isopropanol), dimethylformamide (DMF), dimethyl sulfoxide, acetonitrile, or mixtures of such solvents, with water as an optional co-solvent. A suitable base, such as alkali metal $C_{1-6}$ alkoxide (e.g., NaOMe, KO$^t$Bu), alkali metal hydroxide (e.g., NaOH, KOH), alkali metal carbonate (e.g., Na$_2$CO$_3$, K$_2$CO$_3$ or Cs$_2$CO$_3$), amine (e.g., ethylamine, propylamine, dimethylamine, trimethylammine or isopropyethylamine), alkali metal fluoride (e.g., NaF or KF), or alkali metal phosphate (e.g., Na$_3$PO$_4$, Na$_2$HPO$_4$, NaH$_2$PO$_4$, K$_2$HPO$_4$, KH$_2$PO$_4$ or K$_3$PO$_4$) can be used for reaction 10 described in any one of the foregoing embodiments. In one embodiment, the base is selected from the group consisting of NaOH, KOH, K$_2$CO$_3$, Na$_2$CO$_3$, Cs$_2$CO$_3$, KO$^t$Bu, KF, K$_3$PO$_4$ and Et$_3$N. In one embodiment, reaction 10 is carried out in the presence of Pd(PPh$_3$)$_4$ and a base (e.g., Na$_2$CO$_3$ or KF) in a solvent selected from the group consisting of DMF, dioxane and toluene/EtOH.

In one embodiment, for reaction 10 described in any of the foregoing embodiments, $R_6$ is an optionally substituted phenyl, optionally substituted heteroaryl, —CH═CH-(optionally substituted phenyl), or —CH═CH-(optionally substituted heteroaryl).

Alternatively, the spiro cyclopropyl indolinone compound represented Structural Formula (A) can be prepared by Heck reaction (reaction 11) of the halogenated indolinone compound of Structural Formula (XIIIB) with $R^6$H in the presence of a palladium catalyst and a base, wherein $R^6$ is a $C_{2-10}$ alkenyl optionally substituted with one or more substituents selected from the group consisting of halogen, hydroxy, nitro, cyano, amino, phenyl, 5-12 membered heteroaryl, $C_1$-$C_6$ alkoxy, $C_1$-$C_6$ haloalkoxy, $C_{1-6}$ alkylamino, $C_{1-6}$ dialkylamino, —C(O)H, —C(O)($C_1$-$C_6$ alkyl), —C(O)($C_1$-$C_6$ haloalkyl), —C(O)(phenyl), —C(O)(non-aromatic heterocyclic group), —C(O)O(C1-C6 alkyl), —C(O)O(C1-C6 haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl) and —S(O)$_2$(phenyl), and the phenyl and heteroaryl groups in the substituents for the $C_{2-10}$ alkenyl group represented by $R^6$ independently are optionally substituted with one or more substituents selected from the group consisting of halogen, —OH, —SH, nitro, cyano, amino, $C_{1-6}$ alkylamino, $C_{1-6}$ dialkylamino, ($C_{1-6}$ dialkylamino)$C_{1-6}$ dialkylamino, $C_1$-$C_6$ alkyl, $C_1$-$C_6$ haloalkyl, —O($C_{1-6}$ alkyl), —O-(non-aromatic heterocyclic group), —S($C_{1-6}$ alkyl), —O($C_{1-6}$ haloalkyl), ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, ($C_{1-6}$ dialkylamino)$C_{1-6}$ alkoxy, (phenyl)$C_{0-6}$ alkyl, (5-6 membered heteroaryl)$C_{0-6}$ alkyl, (non-aromatic heterocyclic group)$C_{0-6}$ alkyl (optionally substituted with halogen, —OH, $C_{1-6}$ alkyl, ($C_{1-6}$ alkoxy)$C_{1-6}$ alkyl, $C_{1-6}$ acyl, alkylamino, dialkylamino or non-aromatic heterocyclic group), (5-6 membered heteroaryl)$C_{1-6}$ alkoxy, (non-aromatic heterocyclic group)$C_{1-6}$ alkoxy, —C(O)($C_1$-$C_6$ alkyl), —C(O)($C_1$-$C_6$ haloalkyl), —C(O)(phenyl), —C(O)(non-aromatic heterocyclic group), —C(O)O($C_1$-$C_6$ alkyl), —C(O)O($C_1$-$C_6$ haloalkyl), —C(O) O(phenyl), —OC(O)($C_1$-$C_6$ alkyl), —OC(O)($C_1$-$C_6$ haloalkyl), —OC(O)(phenyl), —S(O)$_2$NH$_2$, —S(O)$_2$($C_1$-$C_6$ alkyl), —S(O)$_2$($C_{1-6}$ haloalkyl), and —S(O)$_2$(phenyl). In one embodiment, the halogenated indolinone compound is the iodinated indolinone compound represented by Structural Formula (XIII). The reaction is carried out in typical Heck reaction conditions. The reaction is preferably effected under microwave irradiation conditions, advantageously in the range, for example of 100 to 150° C., or generally at about 120° C.

In one embodiment, for reaction 11 described in any of the foregoing embodiments, $R_6$ is —CH═CH-(optionally substituted phenyl), or —CH═CH-(optionally substituted heteroaryl).

In another alternative, the spiro cyclopropyl indolinone compound represented Structural Formula (A) can be prepared by Sonagashira reaction (reaction 12) of the halogenated indolinone compound of Structural Formula (XIIIB) with $R_6$H in the presence of a palladium catalyst and Cu(I)X, wherein X is halide and $R_6$ is $C_{2-10}$ alkynyl optionally substituted with one or more substituents selected from the group consisting of halogen, hydroxy, nitro, cyano, amino, phenyl, 5-12 membered heteroaryl, $C_1$-$C_6$ alkoxy, $C_1$-$C_6$ haloalkoxy, $C_{1-6}$ alkylamino, $C_{1-6}$ dialkylamino, —C(O)H, —C(O)($C_1$-$C_6$ alkyl), —C(O)($C_1$-$C_6$ haloalkyl), —C(O) (phenyl), —C(O)(non-aromatic heterocyclic group), —C(O)O(C1-C6 alkyl), —C(O)O(C1-C6 haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl) and —S(O)$_2$(phenyl), and the phenyl and heteroaryl groups in the substituents for the $C_{2-10}$ alkynyl group represented by $R^6$ independently are optionally substituted with one or more substituents selected from the group consisting of halogen, —OH, —SH, nitro, cyano, amino, $C_{1-6}$ alkylamino, $C_{1-6}$ dialkylamino, ($C_{1-6}$ dialkylamino)$C_{1-6}$ dialkylamino, $C_1$-$C_6$ alkyl, $C_1$-$C_6$ haloalkyl, —O($C_{1-6}$ alkyl), —O-(non-aromatic heterocyclic group), —S($C_{1-6}$ alkyl), —O($C_{1-6}$ haloalkyl), ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, ($C_{1-6}$ dialkylamino)$C_{1-6}$ alkoxy, (phenyl)$C_{0-6}$ alkyl, (5-6 membered heteroaryl)$C_{1-6}$ alkyl, (non-aromatic heterocyclic group)$C_{0-6}$ alkyl (optionally substituted with halogen, —OH, $C_{1-6}$ alkyl, ($C_{1-6}$ alkoxy)$C_{1-6}$ alkyl, $C_{1-6}$ acyl, alkylamino, dialkylamino or non-aromatic heterocyclic group), (5-6 membered heteroaryl)$C_{1-6}$ alkoxy, (non-aromatic heterocyclic group)$C_{1-6}$ alkoxy, —C(O)($C_1$-$C_6$ alkyl), —C(O)($C_1$-$C_6$ haloalkyl), —C(O)(phenyl), —C(O) (non-aromatic heterocyclic group), —C(O)O($C_1$-$C_6$ alkyl), —C(O)O($C_1$-$C_6$ haloalkyl), —C(O)O(phenyl), —OC(O) ($C_1$-$C_6$ alkyl), —OC(O)($C_1$-$C_6$ haloalkyl), —OC(O)(phenyl), —S(O)$_2$NH$_2$, —S(O)$_2$($C_1$-$C_6$ alkyl), —S(O)$_2$($C_{1-6}$ haloalkyl), and —S(O)$_2$(phenyl). In one embodiment, the halogenated indolinone compound is the iodinated indolinone compound represented by Structural Formula (XIII). The reaction is carried out under typical Sonagashira reaction conditions. The reaction is preferably effected under microwave irradiation conditions, advantageously in the range, for example of 100 to 150° C., or generally at 120° C.

In one embodiment, for reaction 12, $R^6$ is —C≡C-(optionally substituted phenyl) or —C≡C-(optionally substituted heteroaryl).

In one embodiment, for reaction 10, reaction 10a, reaction 11 and reaction 12 described in any of the foregoing embodiments, the heteroaryl in the group represented by $R^6$ is a 5-12 membered heteroaryl. Exemplary 5-12 membered heteroaryls include pyridyl, thiazolyl, pyrazinyl, thiophenyl, indolyl, quinolinyl, pyrrolyl, pyrazolyl, and pyrimidinyl, each of which is optionally substituted. The phenyl and the 5-12 membered heteroaryl in the group represented by $R^6$ are optionally substituted with one or more substituents selected from the group consisting of halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl and $C_{1-6}$ alkylcarbonyl.

In one embodiment, for reaction 10, reaction 10a, reaction 11 and reaction 12 described in any of the foregoing embodiments, the spiro cyclopropyl indolinone compound is represented by Structural Formula (Aa):

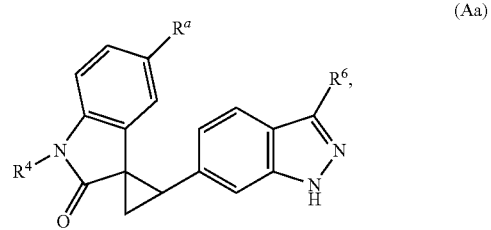

(Aa)

and the iodinated indolinone compound is represented by Structural Formula (XIIIa) described above.

In another embodiment, for reaction 10, reaction 10a, reaction 11 and reaction 12 described in any of the foregoing embodiments, the spiro cyclopropyl indolinone compound is represented by Structural Formula (Ab):

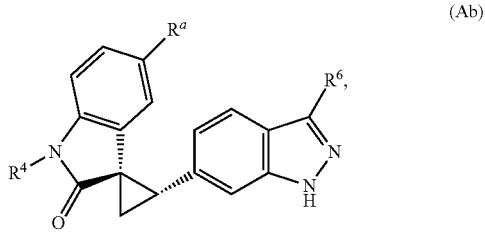

(Ab)

and the iodinated indolinone compound is represented by Structural Formula (XIIIb) described above.

In yet another embodiment, for reaction 10, reaction 10a, reaction 11 and reaction 12 described in any one of the foregoing embodiments, the spiro cyclopropyl indolinone compound is represented by Structural Formula (Ac):

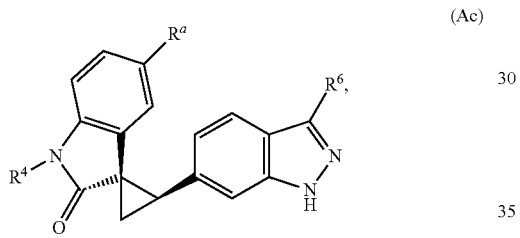

(Ac)

and the iodinated indolinone compound is represented by Structural Formula (XIIIc) described above.

In yet another embodiment, for compounds of Structural Formula (XIII) in reaction 10, reaction 10a, reaction 11 and reaction 12 described in any one of the foregoing embodiments, the indazole N1 nitrogen atom can be optionally substituted with a nitrogen protecting group $P^1$ described above. Accordingly, the spiro cyclopropyl indolinone compound of Structural Formula (A) can be prepared by reaction 10, reaction 10a, reaction 11 and reaction 12 followed by a deprotection reaction to replace the $P^1$ group with —H. The protecting group $P^1$ can be removed according to known procedures described in *Protective Groups in Organic Synthesis*, Greene and Wuts, 3$^{rd}$ edition, 1999, including those described for reaction 9.

In yet another embodiment, for compounds of Structural Formula (XIIA) in reaction 8 and reaction 8a and compounds of Structural Formula (XIII) in reaction 10, reaction 10a, reaction 11 and reaction 12 described in any one of the foregoing embodiments, the indolinone compound represented by Structural Formula (XIIb) and (XIIc) and the halogenated indolinone compound represented by Structural Formula (XIIIb) and (XIIIc) can be obtained by chiral preparative HPLC or Supercritical Fluid Chromatography (SFC) purification by dissolving a racemic or partially enantiomerically enriched mixture in a suitable solvent, and injecting into a column containing a chiral stationary phase, for example, Lux Cellulose-1, Lux Cellulose-2, Lux Amylose-2, Chiralpak 1A, Chiralpak 1B, Chiralpak AS-H or Chiralcel OJ-H, and eluting with a mobile phase. For chiral HPLC, the mode is typically normal phase where the mobile phase can be selected from a solvent mixture comprising a non-polar solvent, for example hexane or hepane, and a polar solvent, for example ethanol or IPA. For chiral SFC, the mobile phase is selected from a mixture comprised of a polar solvent such as methanol, ethanol, isopropanol or isobutanol, with supercritical $CO_2$ at a suitable pressure.

The present invention is also directed to a compound represented by any one of Structural Formulas (I)-(XIII), (IVa)-(XIIIa), (Vb)-(XIIIb), (Vc)-(XIIIc), (VI'), (XI'), (XII'), (XIIIA) and (XIIIB) described above. In one embodiment, the compound represented by Structural Formula (XIIb) is not a compound represented by the following structural formula:

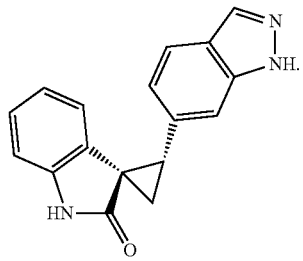 [SMILES: O=C1Nc2ccccc2[C@]12C[C@H]2c1ccc2cn[nH]c2c1]

In another embodiment, the compound represented by Structural Formula (XIIc) is not a compound represented by the following structural formula:

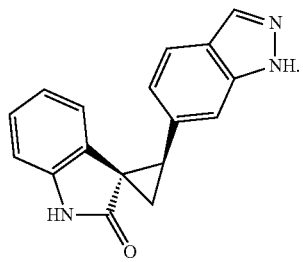 [SMILES: O=C1Nc2ccccc2[C@@]12C[C@@H]2c1ccc2cn[nH]c2c1]

The present invention is also directed to a compound represented by Structural Formula (XVa), (XVb), (XVc) or (XVd):

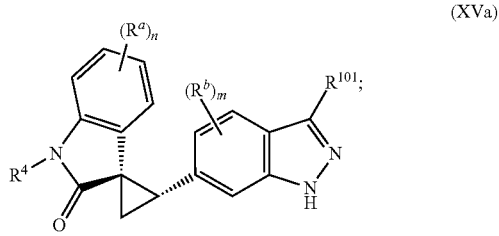

(XVa)

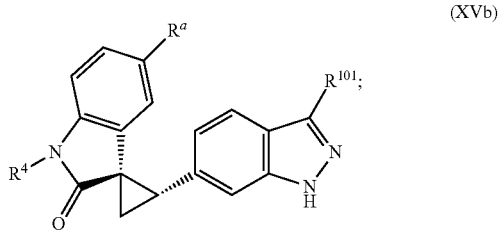

(XVb)

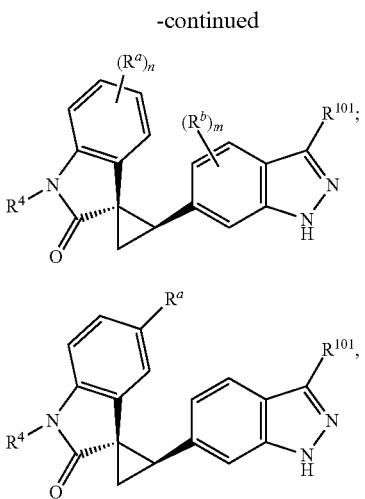

wherein R¹⁰¹ is —H or halogen and values of the remainder of the variables are as described above for Structural Formula, provided that the compound represented by Structural Formula (XVa) or (XVb) is not a compound represented by the following structural formula:

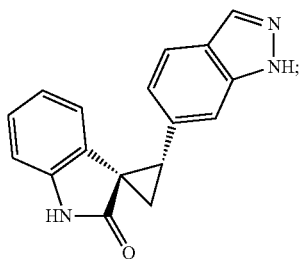 [SMILES: O=C1Nc2ccccc2[C@]12C[C@H]2c1ccc2cn[nH]c2c1]

and the compound represented by Structural Formula (XVc) or (XVd) is not a compound represented by the following structural formula:

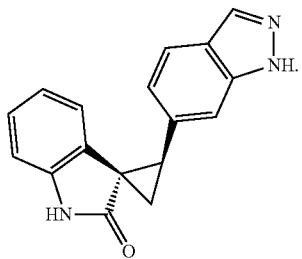 [SMILES: O=C1Nc2ccccc2[C@@]12C[C@@H]2c1ccc2cn[nH]c2c1]

In one embodiment, for Structural Formulas (XVa), (XVb), (XVc) or (XVd), R¹⁰¹ is —H or —I.

In a first embodiment, for Structural Formulas (I), (II), (IV), (IVa), (V), (Va), (Vb), (Vc), (VI), (VIa), (VIb), (VIc), (VI'), (XI), (XIa), (XIb), (XIc), (XI'), and (XIIIA), P¹ is —C(=O)O—R$^P$, —SO₂—R$^P$ or benzyl optionally substituted one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy and ($C_{1-6}$ alkoxy)$C_{1-6}$ alkyl; and R$^P$ is $C_{1-6}$ alkyl, $C_{1-6}$ haloalkyl, —$C_{1-6}$ alkylene-Si($C_{1-6}$ alkyl)₃, phenyl optionally substituted with one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy and ($C_{1-6}$ alkoxy)$C_{1-6}$ alkyl; the remainder of the variables are as described above for Structural Formula (A). Alternatively, P¹ is benzyl, p-methoxybenzyl, 2,4-dimethoxybenzyl, and 2-hydroxybenzyl. In another alternative, P¹ is benzyl or p-methoxybenzyl.

In a second embodiments, for Structural Formulas (VII), (VIIa), (VIII), (VIIIa), (X), (Xa), (XI), (XIa), (XIb), (XIc), (XI') and (XIIIA), P² is $C_{1-6}$ alkyl, $C_{1-6}$ haloalkyl, ($C_{1-6}$ alkoxy)$C_{1-6}$ alkyl, —C(=O)O—R$^P$, —SO₂—R$^P$ or benzyl optionally substituted one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy, ($C_{1-6}$ alkoxy)$C_{1-6}$ alkyl; and R$^P$ is $C_{1-6}$ alkyl, $C_{1-6}$ haloalkyl, —$C_{1-6}$ alkylene-Si($C_{1-6}$ alkyl)₃, phenyl optionally substituted with one or more substituents independently selected from the group consisting of halogen, nitro, $C_{1-6}$ alkyl, $C_{1-6}$ haloalkyl, $C_{1-6}$ alkoxy, $C_{1-6}$ haloalkoxy and ($C_{1-6}$ alkoxy) $C_{1-6}$ alkyl. Values and alternative values for the remainder of the variables are as described above for Structural Formula (A) or in the first embodiment. Alternatively, P² is methyl, —CH₂CH₂OMe, benzyl or p-methoxybenzyl.

In a third embodiment, for Structural Formulas (I), (II), (IV), (V), (VI), (VI'), (VII), (VIIa), (VIII), (VIIIa), (IX), (IXa), (X), (Xa), (XI)-(XIII), (XIa)-(XIIIa), (XIb)-(XIIIb), (XIc)-(XIIIc), (XI'), (XII'), (XIIIA), (XIIIB), (XVa), (XVb), (XVc), (XVd), (A), (Aa), (Ab) and (Ac), each R$^a$ and R$^b$, when present (in Structural Formula (I), (II), (IV), (V), (VI), (VI'), (XI), (XI'), (XII), (XIII), (XVa), (XVc) and (A), are each independently —H, halogen, cyano, —NR¹R², —NR²C(O)R¹, —C(O)OR¹, —OC(O)R¹, —C(O)NR¹R², —NR²C(O)OR¹, —N(R²)C(O)NR¹R², —OR¹, —SO₂NR¹R², —NR²SO₂R¹, $C_{1-6}$ alkyl, phenyl or 5-12 membered heteroaryl, wherein 5-12 membered heteroaryl represented by R$^a$ and R$^b$ is selected from the group consisting of pyridyl, thiazolyl, pyrazinyl, thiophenyl, indolyl, quinolinyl, pyrrolyl, pyrazolyl, and pyrimidinyl; the $C_{1-6}$ alkyl represented by R$^a$ and R$^b$ is optionally substituted with one or more substituents selected from the group consisting of halogen, nitro, cyano, —OH, —SH, —O($C_{1-6}$ alkyl), —S($C_{1-6}$ alkyl), $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl; and the phenyl or the 5-12 membered heteroaryl represented by R$^a$ and R$^b$ is optionally substituted with one or more substituents selected from the group consisting of halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl and $C_{1-6}$ alkylcarbonyl;

each R¹ is independently —H or $C_{1-6}$ alkyl, wherein the $C_{1-6}$ alkyl is optionally substituted with one or more substituents independently selected from the group consisting of halogen, —OH, —SH, —O($C_{1-3}$ alkyl), —S($C_{1-3}$ alkyl) and $C_{1-6}$ haloalkoxy; and each R² is independently —H or $C_{1-6}$ alkyl. Values and alternative values for the remainder of the variables are as described for Structural Formula (A), or in the first or second embodiment.

In a fourth embodiment, for Structural Formulas (I), (II), (IV), (V), (VI), (VI)', (VII), (VIIa), (VIII), (VIIIa), (IX), (IXa), (X), (Xa), (XI)-(XIII), (XIa)-(XIIIa), (XIb)-(XIIIb), (XIc)-(XIIIc), (XI'), (XII'), (XIIIA), (XIIIB), (XVa), (XVb), (XVc), (XVd), (A), (Aa), (Ab) and (Ac), each R$^a$ and R$^b$, when present (in Structural Formula (I), (II), (IV), (V), (VI), (VI)', (XI), (XI'), (XII), (XIII), (XVa), (XVd) and (A)) are each independently —H, halogen, $C_{1-3}$ alkyl or $C_{1-3}$ alkoxy. Values and alternative values for the remainder of the variables are as described above for Structural Formula (A), or in the first or second embodiment.

In fifth alternative, for Structural Formulas (I), (II), (IV), (V), (VI), (VI'), (VII), (VIIa), (VIII), (VIIIa), (IX), (IXa), (X), (Xa), (XI)-(XIII), (XIa)-(XIIIa), (XIb)-(XIIIb), (XIc)-(XIIIc), (XI'), (XII'), (XIIIA), (XIIIB), (XVa), (XVb), (XVc), (XVd), (A), (Aa), (Ab) and (Ac), each $R^a$ and $R^b$, when present (in Structural Formula (I), (II), (IV), (V), (VI), (VI)', (XI), (XI'), (XII), (XIII), (XVa), (XVc) and (A)) are each independently —H, —F, methyl, ethyl or methoxy. Values and alternative values for the remainder of the variables are as described above for Structural Formula (A), or in the first or second embodiment.

In a sixth embodiment, for Structural Formulas (XII)-(XIII), (XIIa)-(XIIIa), (XIIb)-(XIIIb), (XIIc)-(XIIIc), (XII'), (XIIIA), (XIIIB), (XVa), (XVb), (XVc), (XVd), (A), (Aa), (Ab) and (Ac), $R^4$ is H, C1-C6 alkyl, phenyl, —C(O)(C1-C6 alkyl), —C(O)(phenyl), —C(O)O(C1-C6 alkyl), —C(O)O(phenyl), —S(O)$_2$(C1-C6 alkyl) or —S(O)$_2$(phenyl), wherein each alkyl in the groups represented by $R^4$ is optionally substituted with one or more substituents selected from the group consisting of halogen, hydroxy, nitro, cyano, amino, —C(O)NH$_2$, phenyl, 5-6 membered heteroaryl, $C_{1-6}$ alkoxy, $C_{1-6}$ alkylamino, $C_{1-6}$ dialkylamino and $C_{1-6}$ haloalkoxy and wherein each phenyl in the groups represented by $R^4$ is optionally substituted with one or more substituents selected from the group consisting of halogen, hydroxyl, nitro, cyano, amino, $C_{1-6}$ alkyl, $C_{1-6}$ haloalkyl, $C_{1-6}$ alkoxy and $C_{1-6}$ haloalkoxy. Values and alternative values for the remainder of the variables are as described above for Structural Formula (A), or in the first, second, third, fourth or fifth embodiment.

In a seventh embodiment, for Structural Formulas (XII)-(XIII), (XIIa)-(XIIIa), (XIIb)-(XIIIb), (XIIc)-(XIIIc), (XII'), (XIIIA), (XIIIB), (XVa), (XVb), (XVc), (XVd), (A), (Aa), (Ab) and (Ac), $R^4$ is —H, methyl, ethyl or —CH$_2$CH$_2$OMe. Values and alternative values for the remainder of the variables are as described above above for Structural Formula (A), or in the first, second, third, fourth or fifth embodiment.

In a eighth embodiment, for Structural Formulas (VI'), (XI'), (XII'), (A), (Aa), (Ab) and (Ac), $R^6$ is optionally substituted phenyl, optionally substituted 5-12 membered heteroaryl, —CH$_2$-(optionally substituted phenyl), —CH$_2$-(optionally substituted 5-12 membered heteroaryl), —CH$_2$—CH$_2$-(optionally substituted phenyl), —CH$_2$—CH$_2$-(optionally substituted 5-12 membered heteroaryl), —CH=CH-(optionally substituted phenyl), —CH=CH-(optionally substituted 5-12 membered heteroaryl), —C≡C-(optionally substituted phenyl) or —C≡C-(5-12 optionally substituted membered heteroaryl). Values and alternative values for the remainder of the variables are as described for Structural Formula, or in the first, second, third, fourth, fifth, sixth or seventh embodiment. Exemplary 5-12 membered heteroaryls in the group represented by $R^6$ include pyridyl, thiazolyl, pyrazinyl, thiophenyl, indolyl, quinolinyl, pyrrolyl, pyrazolyl, and pyrimidinyl, each of which is optionally substituted. An alternative group of exemplary 5-12 membered heteroaryls in the group represented by $R^6$ include optionally substituted pyridinyl, pyrimidinyl or pyrazinyl.

In a ninth embodiment, for Structural Formulas (VI'), (XI'), (XII'), (A), (Aa), (Ab) and (Ac), $R^6$ is optionally substituted phenyl, —CH=CH-(optionally substituted phenyl) or —C≡C-(optionally substituted phenyl); values and alternative values for the remainder of the variables are as described above for Structural Formula (A), or in the first, second, third, fourth, fifth, sixth or seventh embodiment.

In one embodiment, the phenyl and the 5-12 membered heteroaryl in the group represented by $R^6$ described in the eighth or ninth embodiment are optionally substituted with one or more substituents selected from the group consisting of halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl, $C_{1-6}$ alkylcarbonyl, —(CH$_2$)$_{0-3}$—N-piperidinyl, —(CH$_2$)$_{0-3}$—N-morpholinyl, —(CH$_2$)$_{0-3}$—N-pyrrolidinyl, —(CH$_2$)$_{0-3}$—N-piperazinyl and —(CH$_2$)$_{0-3}$—N-oxazepanyl, wherein the N-pyrrolidinyl, N-morpholinyl and N-piperazinyl is optionally substituted with halogen, $C_{1-6}$ alkyl, ($C_{1-6}$ alkoxy)$C_{1-6}$ alkyl, di($C_{1-6}$ alkyl)amino or $C_{1-6}$ acyl (alternatively, the N-piperazinyl is N'-substituted with $C_{1-6}$ alkyl or ($C_{1-6}$ alkoxy)$C_{1-6}$ alkyl).

In a tenth embodiment, for Structural Formulas (VI'), (XI'), (XII'), (A), (Aa), (Ab) and (Ac), $R^6$ is —CH=CH-(phenyl); and the phenyl in —CH=CH-(phenyl) is optionally substituted with one or more substituents independently selected from the group consisting of halogen, $C_{1-6}$ alkyl, $C_{1-6}$ haloalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, amino, $C_{1-6}$ alkylamino, $C_{1-6}$ dialkylamino, —(CH$_2$)$_{0-3}$—N-piperidinyl, —(CH$_2$)$_{0-3}$-N-morpholinyl, —(CH$_2$)$_{0-3}$—N-pyrrolidinyl, —(CH$_2$)$_{0-3}$—N-piperazinyl and —(CH$_2$)$_{0-3}$—N-oxazepanyl, wherein the N-pyrrolidinyl, N-morpholinyl and N-piperazinyl is optionally substituted with halogen, $C_{1-6}$ alkyl, ($C_{1-6}$ alkoxy)$C_{1-6}$ alkyl, di($C_{1-6}$ alkyl)amino or $C_{1-6}$ acyl (alternatively, the N-piperazinyl is N'-substituted with $C_{1-6}$ alkyl or ($C_{1-6}$ alkoxy)$C_{1-6}$ alkyl). Values and alternative values for the remainder of the variables are as described above for Structural Formula (A), or in the first, second, third, fourth, fifth, sixth or seventh embodiment.

In a eleventh embodiment, for Structural Formulas (VI'), (XI'), (XII'), (A), (Aa), (Ab) and (Ac), $R^6$ is phenyl optionally substituted with —(CH$_2$)$_{0-3}$—N-piperazinyl, wherein the N-piperazinyl is optionally N'-substituted with $C_{1-6}$ alkyl or ($C_{1-6}$ alkoxy)$C_{1-6}$ alkyl. Values and alternative values for the remainder of the variables are as described above for Structural Formula (A), or in the first, second, third, fourth, fifth, sixth or seventh embodiment.

In one embodiment, for Structural Formulas (VI'), (XI'), (XII'), (A), (Aa), (Ab) and (Ac), $R^a$, is —F, methyl, ethyl or methoxy; and $R^4$, when present, is —H, methyl, ethyl or methoxyethyl. Values and alternative values for the remainder of the variables are as described in the tenth or eleventh embodiment.

When a compound is designated by a name or structure that indicates a single enantiomer, unless indicated otherwise, the compound is at least 60%, 70%, 80%, 90%, 95%, 96%, 97%, 97.5%, 98%, 98.5%, 99%, 99.5%, 99.8%, 99.9% or 100% optically pure (also referred to as "enantiomerically pure"). Optical purity is the weight in the mixture of the named or depicted enantiomer divided by the total weight in the mixture of both enantiomers. Alternatively, when a compound is designated by a name or structure that indicates a single enantiomer, unless indicated otherwise, the compound has a percent enantiomeric excess of at least 20%, 40%, 60%, 80%, 90%, 92%, 94%, 95%, 96%, 97%, 97.5%, 98%, 98.5%, 99%, 99.5%, 99.8%, 99.9% or 100%. Percent enantiomeric excess, or percent e.e., is the difference between the percent of the named or depicted enantiomer and the opposite enantiomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 95%, 96%, 97%, 98%, 99%, 99.5%, 99.8%, 99.9% or 100% by weight. The stereoisomeric purity in this case is determined by dividing the total weight in the mixture of the stereoisomers encompassed by the name or structure by the total weight in the mixture of all of the stereoisomers.

The term "halo" as used herein means halogen and includes chloro, fluoro, bromo and iodo.

An "aliphatic group" is acyclic, non-aromatic, consists solely of carbon and hydrogen and may optionally contain one or more units of unsaturation, e.g., double and/or triple bonds. An aliphatic group may be straight chained or branched. An aliphatic group typically contains between about one and about twenty carbon atoms, typically between about one and about ten carbon atoms, more typically between about one and about six carbon atoms. A "substituted aliphatic group" is substituted at any one or more "substitutable carbon atoms". A "substitutable carbon atom" in an aliphatic group is a carbon in the aliphatic group that is bonded to one or more hydrogen atoms. One or more hydrogen atoms can be optionally replaced with a suitable substituent group. A "haloaliphatic group" is an aliphatic group, as defined above, substituted with one or more halogen atoms.

The term "alkyl" used alone or as part of a larger moiety, such as "alkoxy", "haloalkyl", "arylalkyl", "alkylamine", "dialkyamine", "alkylamino", "dialkyamino" "alkylcarbonyl", "alkoxycarbonyl" and the like, means saturated straight-chain or branched aliphatic group. As used herein, a C1-C6 alkyl group is referred to "lower alkyl." Similarly, the terms "lower alkoxy", "lower haloalkyl", "lower arylalkyl", "lower alkylamine", "lower dialkyamine", "lower alkylamino", "lower dialkyamino" "lower alkylcarbonyl", "lower alkoxycarbonyl" include straight and branched, saturated chains containing one to six carbon atoms.

The term "alkenyl" means straight-chain or branched aliphatic group having at least one double bond.

The term "alkynyl" means straight-chain or branched aliphatic group having at least one triple bond.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkyamine" means amine substituted with two alkyl groups; "alkylcarbonyl" means —C(O)—R, wherein R is alkyl; "alkoxycarbonyl" means —C(O)—OR, wherein R is alkyl; and where alkyl is as defined above.

The terms "haloalkyl" and "haloalkoxy" means alkyl or alkoxy, as the case may be, substituted with one or more halogen atoms. The term "halogen" means F, Cl, Br or I. Preferably the halogen in a haloalkyl or haloalkoxy is F.

The term "acyl group" means —C(O)R, wherein R is an optionally substituted alkyl group or aryl group (e.g., optionally substituted phenyl). R is preferably an unsubstituted alkyl group or phenyl.

An "alkylene group" is represented by —[CH$_2$]$_z$—, wherein z is a positive integer, preferably from one to eight, more preferably from one to four.

An "alkenylene" is an alkylene group in which one methylene has been replaced with a double bond.

The term "aryl group" used alone or as part of a larger moiety as in "aralkyl", "aralkoxy", or "aryloxyalkyl", means a carbocyclic aromatic ring. The term "aryl" may be used interchangeably with the terms "aryl ring" "carbocyclic aromatic ring", "aryl group" and "carbocyclic aromatic group". An aryl group typically has six to fourteen ring atoms. Examples includes phenyl, naphthyl, anthracenyl, 1,2-dihydronaphthyl, 1,2,3,4-tetrahydronaphthyl, fluorenyl, indanyl, indenyl and the like. A "substituted aryl group" is substituted at any one or more substitutable ring atom, which is a ring carbon atom bonded to a hydrogen.

The term "cycloalkyl" refers to a monocyclic or polycyclic saturated hydrocarbon ring system. For example, a $C_{5-7}$ cycloalkyl includes, but is not limited to cyclopentyl, cyclohexyl or cyclopentyl, each of which is optionally substituted.

The term "heteroaryl", "heteroaromatic", "heteroaryl ring", "heteroaryl group", "heteroaromatic ring", and "heteroaromatic group", used alone or as part of a larger moiety as in "heteroaralkyl" or "heteroarylalkoxy", refers to aromatic ring groups having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other carbocyclic aromatic or heteroaromatic rings. As such, "5-14 membered heteroaryl" includes monocyclic, bicyclic or tricyclic ring systems.

Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl), thienyl (e.g., 2-thienyl, 3-thienyl), pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl. A "substituted heteroaryl group" is substituted at any one or more substitutable ring atom, which is a ring carbon or ring nitrogen atom bonded to a hydrogen.

The term "heterocyclyl group" or "heterocyclic group" means a monocyclic, non-aromatic ring with 3 to 10-members containing from 1-3 ring heteroatoms or a polycyclic ring with ring with 7 to 20-members and from 1 to 4 ring heteroatoms, wherein the polycyclic ring having one or more monocyclic non-aromatic heterocyclic ring fused with one or more aromatic or heteroaromatic ring. In one embodiment, the heterocyclyl group is a bicyclic ring having a monocyclic non-aromatic heterocyclic ring fused with a phenyl group. Exemplary polycyclic heterocyclic group includes tetrahydroisoquinolinyl (such as 1,2,3,4-tetrahydroisoquinolin-7-yl, 2-methyl-1,2,3,4-tetrahydroisoquinolin-7-yl, 1,2,3,4-tetrahydroisoquinolin-6-yl and 2-methyl-1,2,3,4-tetrahydroisoquinolin-6-yl), isoindolinyl (such as 2-ethylisoindolin-5-yl, 2-methylisoindolin-5-yl), indolinyl, tetrahydrobenzo[f]oxazepinyl (such as 2,3,4,5-tetrahydrobenzo[f][1,4]oxazepin-7-yl).

The term "non-aromatic heterocyclic group" means a monocyclic, non-aromatic ring with 3 to 10-members containing from 1-3 ring heteroatoms or a polycyclic non-aromatic ring with 7 to 20-members and from 1 to 4 ring heteroatoms. Each heteroatom is independently selected from nitrogen, quaternary nitrogen, oxidized nitrogen (e.g., NO); oxygen; and sulfur, including sulfoxide and sulfone. The substituted non-aromatic heterocylic group may be attached via a suitable heteroatom or carbon atom. Representative non-aromatic heterocyclic groups include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A "substituted non-aromatic heterocylic group" is substituted at any one or more substitutable ring atom, which is a ring carbon or ring nitrogen atom bonded to a hydrogen.

Unless otherwise indicated, suitable substituents for a substituted aliphatic group (such as alkyl, alkenyl, alkynyl, cycloalkyl), aryl group, heteroaryl group, heterocyclic group and non-aromatic heterocyclic groups include the groups represented by $R^a$. Other examples include halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy)$C_{1-20}$ alkyl, $C_{1-20}$ haloalkoxy, $(C_{1-10}$ haloalkoxy)$C_{1-20}$ alkyl and $C_{1-20}$ haloalkyl.

A "salt" of a compound disclosed herein refers to a salt formed a compound disclosed herein having basic amine groups with an organic or inorganic acid or a salt formed from a compound disclosed herein having having acidic groups such as carboxylic acids with an organic or inorganic base. Salts formed with a pharmaceutically acceptable acid or base are referred to as "pharmaceutically acceptable salts". Suitable pharmaceutically acceptable acid addition salts of the compounds of the invention include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid. Non-pharmaceutically acceptable acid or base can also be used to form a salt of the compound disclosed herein to facilitate compound separation and/or purification. For example, trifluoroacetic acid can be used to form a salt with a compound having an amine functional group.

Unless stated otherwise, exemplary organic solvents include, but are not limited to, ethereal solvents (e.g., diethyl ether, methyl tert-butyl ether, tetrahydrofuran, 1,4-dioxane and dimethoxyethane), aromatic solvents (e.g., benzene and toluene), chlorinated solvents (e.g., methylene chloride and 1,2-dichloroethane), alcohol solvents (e.g., methanol, ethanol, isopropanol), dimethylformamide, dimethyl sulfoxide and acetonitrile.

Unless stated otherwise, exemplary base includes, but are not limited to alkali metal $C_{1-6}$ alkoxide (e.g., NaOMe, KO$^t$Bu), alkali metal hydroxide (e.g., NaOH, KOH), alkali metal carbonate (e.g., $Na_2CO_3$, $K_2CO_3$ or $Cs_2CO_3$), amine (e.g., ethylamine, propylamine, dimethylamine, trimethylammine, isopropyethylamine, pyridine), ammonia, alkali metal fluoride (e.g., NaF or KF), and alkali metal phosphate (e.g., $Na_3PO_4$, $Na_2HPO_4$, $NaH_2PO_4$, $K_2HPO_4$, $KH_2PO_4$ or $K_3PO_4$)

EXEMPLIFICATION

General Synthetic Scheme:

Compounds of the present invention can be prepared according to synthetic methods depicted in Scheme 1:

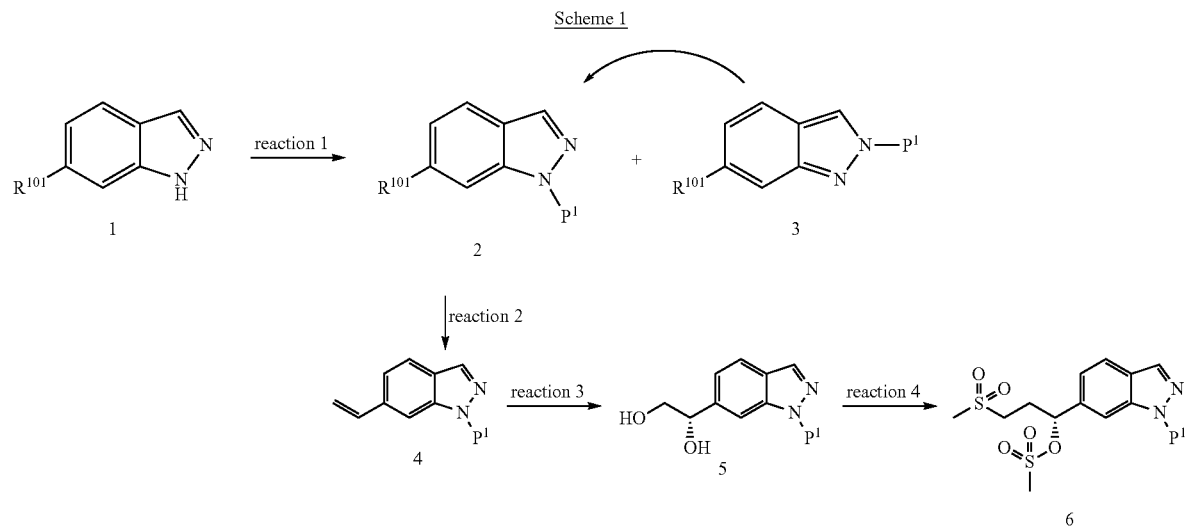

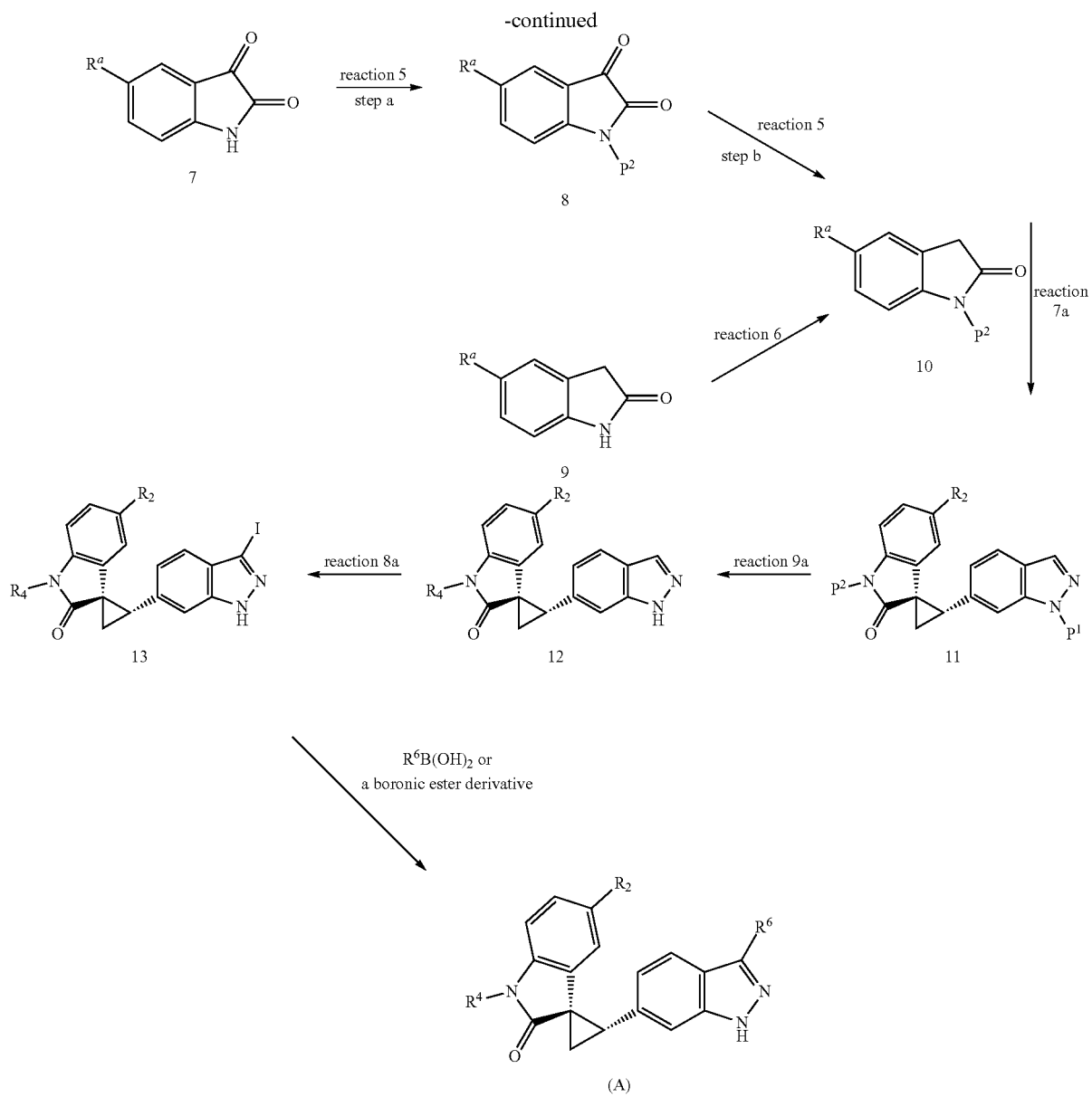

General Experimental Methods:

Commercially available starting materials and reagents were used as received.

In general, anhydrous reactions were performed under an inert atmosphere such as nitrogen or argon except where noted. Where dry solvents were used, these were obtained as follows: toluene, THF and ether were dried and purified on alumina using an Innovative Technologies PureSolv MD apparatus (Grubbs'-style). $CH_2Cl_2$ was obtained by drying over 4 Å molecular sieves, or anhydrous grade was also purchased in sure-seal bottles from Sigma-Aldrich. THF and 1,4-dioxane were collected following distillation over sodium-benzophenone ketyl. Anhydrous grade ACN, DMF and DMSO were purchased from Sigma-Aldrich. Reaction progress was generally monitored by TLC using Merck silica gel plates with visualization by UV at 254 nm, by analytical HPLC or by LCMS (Bruker Esquire 4000). Flash column chromatographic purification was performed using 230-400 mesh silica gel 60 from EMD chemicals, or using the Biotage Isolera flash purification system with SNAP cartridges (KP-HP-SIL, 10 g-100 g) with the samplet of the same material in the appropriate size. $^1$H NMR spectra were recorded on a Bruker 400 MHz or Varian Inova 300 or 400 MHz spectrometer, with chemical shifts given in ppm relative to tetramethylsilane. Mass spectra were obtained using a Bruker Esquire 4000 spectrometer or a Micromass Quattro Micro. Chiral normal-phase HPLC columns (250×4.6 mm) were purchased from Chiral Technologies Europe (Chiralpak IA, IB, AS-H, all fitted with guard cartridge of same material) or Phenomenex (Lux Cellulose-1, Lux Cellulose-2, Lux Amylose-2).

Optical Rotations were measured at the sodium D-line (589.44 nM) using an AA-55 Polarimeter from Optical Activity Ltd with a 2.5×100 mm unjacketed stainless steel tube at given sample concentrations (c, units of g/100 mL).

Compound names were generated using the software built into ChemBioDraw Ultra version 11.0 with the following exception. Racemic compounds with known relative stereochemistry were named using the R*/S* system as described by North (Principles and Applications of Stereochemistry, CRC Press, 1998), wherein the lower numbered atom is arbitrarily defined as R*, and the higher numbered atoms are defined relative to that center. Thus a racemic mixture of enantiomers of a compound with two chiral centers is designated as (1R*,2S*) or (1R*,2R*) depending on the known relative stereochemistry. The standard R and S nomenclature is used to describe single enantiomers or enantiomerically enriched compounds of greater than 95% e.e.

ABBREVIATIONS

ACN acetonitrile
aq. aqueous
br. broad
Bn benzyl
BnCl benzyl chloride
BnBr benzyl bromide
BuLi butyllithium
calcd calculated
$CH_3PPh_3Br$ methyl triphenylphosphonium bromide
$PCy_3$ tricyclohexylphosphine
dba dibenzylideneacetone
DCM dichloromethane
$(DHQ)_2PHAL$ hydroquinine 1,4-phthalazinediyl diether
$(DHQD)_2PHAL$ hydroquinidine 1,4-phthalazinediyl diether
DME 1,2-dimethoxyethane
DMF N,N-dimethylformamide
DMPU 1,3-dimethyl-3,4,5,6-tetrahydro-2(1H)-pyrimidinone
DMS dimethylsulfide
DMSO dimethylsulfoxide
dppf 1,1'-bis(diphenylphosphino)ferrocene
% e.e. percent enantiomeric excess
$Et_2O$ diethyl ether
$Et_3N$ triethylamine
EtOAc ethyl acetate
EtOH ethanol
h hours
HMPA hexamethylphosphoric triamide
HPLC high performance liquid chromatography
$^iPr_2NEt$ diisopropyl ethyl amine
$^iPrOH$ iso-propanol
$KO^tBu$ potassium tert-butoxide
LC-MS liquid chromatography coupled to mass spectroscopy
MeOH methanol
min minutes
MoOPH oxodiperoxymolybdenum(pyridine)(HMPA); MoO5.Py.HMPA
MoOPD oxodiperoxymolybdenum(pyridine)(DMPU); MoO5.Py.DMPU
MsCl methanesulfonyl chloride
MS ESI mass spectra, electrospray ionization
$NaO^tBu$ sodium tert-butoxide
NMO N-methyl morpholine N-oxide
NMP 1-methyl-2-pyrrolidinone
NMR nuclear magnetic resonance
O/N overnight
$Pd(OAc)_2$ palladium acetate
Ph phenyl
$PPh_3$ triphenylphosphine
PMB para-methoxybenzyl
PMBCl para-methoxybenzyl chloride
$Q_2(PHAL)$ quinine 1,4-phthalazinediyl diether
RBF round bottomed flask
rt room temperature
sat. saturated
SFC Supercritical Fluid Chromatography
$^tBuLi$ tert-butyllithium
$^tBuOH$ tert-butanol
tBuOOH tert-butyl hydroperoxide
temp. temperature
TFA trifluoroacetic acid
TfOH trifluoromethanesulfonic acid
THF tetrahydrofuran
TLC thin layer chromatography
wt % percent by weight Preparation of N-substituted Oxindole Intermediates N-Benzyl-oxindole

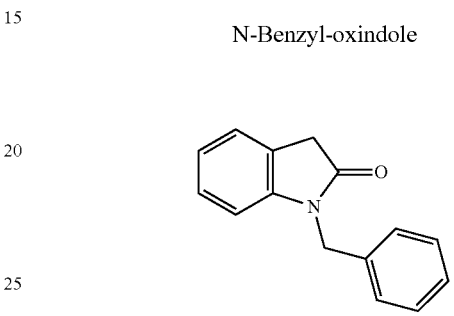

Prepared according to literature procedure (C. Martin and E. M. Carreira, *J. Am. Chem. Soc.*, 2005, 127, 11505-11515). A stirred solution of isatin (10.0 g, 68 mmol) in dry DMF (125 mL) was cooled in an ice bath before addition of sodium hydride (60 wt % in mineral oil, 2.86 g, 71.5 mmol) in 10 portions, the orange solution turning quickly purple. When no further evolution of gas was observed, benzyl bromide (13.4 g, 78.0 mmol) was added by syringe. A colour change back to orange was observed within 20 min. Water (300 mL) was added with stirring, and the resulting orange-red precipitate collected by filtration and washed with water and a little cold ethanol. The solid was then recrystallized from boiling ethanol (300 mL) to afford N-benzylisatin (13.7 g, 85%) as long, red needles.

N-benzylisatin (13.0 g, 55 mmol) was mixed with hydrazine hydrate (60 mL) and placed in an oil bath. The mixture was heated in stages to 125° C., becoming first a green sludge, then yellow with clumps of a sticky solid. After a total of 5 h at 125° C., the mixture was cooled and extracted with EtOAc (2×100 mL). The combined organic portions were washed twice with 1.0 M aq. $H_2SO_4$, and once each with half-saturated brine then brine, dried over $MgSO_4$, filtered and concentrated to afford a pale yellow solid. Re-precipitation from ether/pentane gave the title compound as an off-white solid (9.6 g, 75%). Spectral data matches literature values (C. Martin and E. M. Carreira, *J. Am. Chem. Soc.*, 2005, 127, 11505-11515).

1-Benzyl-5-fluoroindolin-2-one

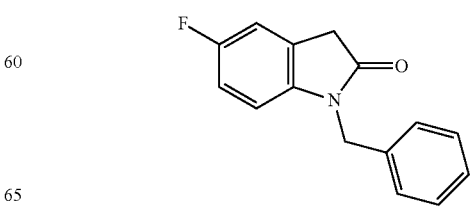

In a manner similar to the method of N-benzylisatin, 5-fluoroisatin (10.0 g, 60.5 mmol) yielded 5-fluoro-N-benzylisatin as an orange red powder (14.5 g, 93%). The crude product was used for the next step without purification. $^1$H NMR (400 MHz, CDCl$_3$) δ 7.33-7.21 (m, 5H), 6.95 (d, J=7.6 Hz, 1H), 6.84 (t, 1H), 6.60 (m, 1H), 4.89 (s, 2H); MS ESI 255.9 [M+H]$^+$, calcd for [C$_{15}$H$_{10}$FNO$_2$+H]$^+$255.07.

The title compound was prepared in a manner similar to the method of N-Benzyl-oxindole using 5-fluoro-N-benzylisatin (14.5 g, 56.8 mmol). Trituration using Et$_2$O:hexane yielded the title compound as a pale yellow solid (10.3 g, 75%). $^1$H NMR (400 MHz, CDCl$_3$) δ 7.30-7.26 (m, 5H), 7.00 (d, J=7.6 Hz, 1H), 6.87 (t, 1H), 6.63 (m, 1H), 4.91 (s, 2H), 3.63 (s, 2H); MS ESI 241.9 [M+H]$^+$, calcd for [C$_{15}$H$_{10}$FNO$_2$+H]$^+$241.09.

1-Benzyl-5-methylindolin-2-one

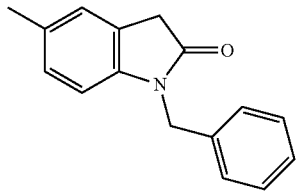 [SMILES: Cc1ccc2c(c1)CC(=O)N2Cc1ccccc1]

To a mixture of 5-methylisatin (8.05 g, 50 mmol) and K$_2$CO$_3$ (8.16 g, 60 mmol) in DMF (100 mL) was added BnBr (6.5 mL, 55 mmol) dropwise over 2 min. After addition, the resulting mixture was heated in an oil bath at 75° C. for 1.5 h. After cooling to rt, the reaction mixture was poured onto ice/cold water (250 mL), rinsed with H$_2$O (50 mL) and stirred for 5 min. The resulting precipitates were collected by suction filtration and air dried to give 1-benzyl-5-methylisatin as dark red solid. MS ESI 252.0 [M+H]$^+$, calcd for [C$_{16}$H$_{13}$NO$_2$+H]$^+$252.1.

1-Benzyl-5-methylisatin was suspended in DMSO (100 mL) and cooled to 0° C. Hydrazine hydrate (5 mL) was added dropwise over 5 min. After addition, the resulting clear red solution was heated at 120° C. for 2 h then 140° C. for 5 h. After cooling to rt, it was poured into a 1 L Erlenmeyer flask, rinsed with H$_2$O (50 mL) and ice was added until a total volume about 300 mL. 2 M HCl (50 mL) was added and the mixture was extracted with EtOAc (200 mL×2, then 100 mL), and the organic layer was dried (Na$_2$SO$_4$). Removal of solvents followed by drying under high vacuum for 2 days gave the title compound as a dark red solid (12.53 g, quantitative yield over 2 steps, contained some DMSO residue). $^1$H NMR (400 MHz, CDCl$_3$) δ 7.35-7.29 (m, 5H), 7.09 (s, 1H), 6.97 (d, J=7.6 Hz, 1H), 6.61 (d, J=8.0 Hz, 1H), 4.91 (s, 2H), 3.60 (s, 2H), 2.31 (s, 3H); MS ESI 238.0 [M+H]$^+$, calcd for [C$_{16}$H$_{15}$NO+H]$^+$238.1.

1-Benzyl-5-methoxyindolin-2-one

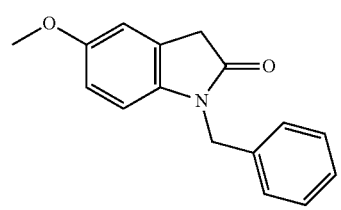 [SMILES: COc1ccc2c(c1)CC(=O)N2Cc1ccccc1]

Method 1: A stirred solution of 5-methoxyisatin (5.0 g, 28 mmol) in dry DMF (40 mL) was cooled in an ice bath before addition of sodium hydride (60 wt % in mineral oil, 1.7 g, 42 mmol) slowly, the dark red solution turning quickly black. After stirring for 20 min, BnBr (3.7 mL, 31 mmol) was added to the reaction mixture by syringe and the resulting mixture was stirred for 1 h. Water (150 mL) was added with stirring, and the resulting dark red precipitate collected by filtration and washed with water to give 1-benzyl-5-methoxyindoline-2,3-dione as a dark red solid (6.1 g, 81%). $^1$H NMR (400 MHz, CDCl$_3$) δ 7.39-7.31 (m, 5H), 7.17 (s, 1H), 7.03 (d, J=8.1 Hz, 1H), 6.68 (d, J=8.6 Hz, 1H), 4.92 (s, 2H), 3.79 (s, 3H). MS ESI 268.1 [M+H]$^+$, calcd for [C$_{16}$H$_{13}$NO$_3$+H]$^+$268.09.

A solution of 1-benzyl-5-methoxyindoline-2,3-dione (6.1 g, 23 mmol) and hydrazine hydrate (50-60% grade, 2.9 mL, ca. 2 eq) in DMSO (15 mL) is heated to 140° C. in an oil bath. After 3 h, the mixture was cooled, diluted with water and EtOAc, the layers separated and the aqueous extracted with EtOAc three times (30 mL). The combined organic portions were washed with 2M H$_2$SO$_4$, brine, and dried over MgSO$_4$, filtered and concentrated to afford the crude product as a viscous brown oil. The crude product was purified by silica gel chromatography (20-50% EtOAc in hexane) to yield the title compound as a brown oil (5.0 g, 85%). $^1$H NMR (400 MHz, CDCl$_3$) δ 7.34-7.23 (m, 5H), 6.89 (s, 1H), 6.69 (d, J=8.3 Hz, 1H), 6.61 (d, J=8.5 Hz, 1H), 4.91 (s, 2H), 3.76 (s, 3H), 3.62 (s, 2H). MS ESI 254.0 [M+H]$^+$, calcd for [C$_{16}$H$_{15}$NO$_2$+H]$^+$254.1.

Method 2: In a similar manner, the title compound was obtained in two steps from 5-methoxyisatin (10.0 g, 56 mmol), K$_2$CO$_3$ (8.58 g, 62 mmol) and BnBr (7.71 mL, 64 mmol) in DMF (50 mL) at 75° C. for 4 h. The reaction mixture was poured into water (1 L) and the resulting suspension was stirred for 30 min at RT. The precipitate was collected by filtration, washed with water (10 mL×3) and dried under vacuum to give 1-benzyl-5-methoxyindoline-2,3-dione (14.51 g, 96%). Hydrazine hydrate (80%, 6.96 mL, 108 mmol) was added to a solution of the solid in DMSO (40 mL) at RT over 10 min. The reaction mixture was heated to 140° C. in an oil bath for 2 h, then cooled and partitioned between water (500 mL) and EtOAc (500 mL). The aqueous layer was extracted with EtOAc (300 mL), and the combined organic layer was washed with brine (75 mL), dried (Na$_2$SO$_4$), filtered and evaporated to give the title compound as a brown oil (13.2 g 96%).

5-Methoxy-1-methylindolin-2-one

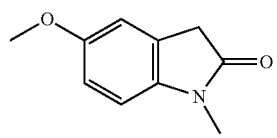

Method 1: A dry round-bottom flask was charged with toluene (50 mL) and sodium hydride (60% wt, 0.512 g, 12.8 mmol) under N$_2$. The resultant suspension was heated to 60° C. and then 5-methoxyindolin-2-one (2.0 g, 12.2 mmol) was added portion wise over 15 min. After 30 min stirring at 60° C. Me$_2$SO$_4$ (1.28 mL, 13.4 mmol) was added over 15 min, and the temperature maintained at 60° C. for 3 h. The reaction was cooled to room temperature and quenched with 25% ammonium chloride solution (40 mL) and the layers were separated. The aqueous layer was extracted using toluene (15 mL×2) and the combined organic layers was washed with water (20 mL×2) and dried (Na$_2$SO$_4$). The solvent was removed under vacuum at 50° C./60 mbar resulted brown semi solid, which was purified on Biotage Isolera (10-50% EtOAc in hexane, SNAP 25 g column) to give the title compound (brown solid, 1.45 g, 67%). $^1$H NMR (400 MHz, CDCl$_3$) δ 6.89 (s, 1H), 6.82 (d, J=8.3 Hz, 1H), 6.71 (d, J=8.4 Hz, 1H), 3.80 (s, 3H), 3.51 (s, 2H), 3.20 (s, 3H); MS ESI 178 [M+H]$^+$, calcd for [C$_{10}$H$_{11}$NO$_2$+H]$^+$ 178.1.

Method 2: In a separate experiment carried out with 5-methoxyindolin-2-one (250 mg, 1.53 mmol) at 100° C. for 2.5 h, evaporation and flash chromatography yielded the title compound (beige solid, 144 mg, 53%).

Method 3: A stirred solution of 5-methoxyisatin (33 g, 186 mmol) in dry DMF (240 mL) was cooled in an ice bath before addition of sodium hydride (60 wt % in mineral oil, 11.2 g, 279 mmol) slowly. After stirring for 20 min, iodomethane (12.8 mL, 205 mmol) was added to the reaction mixture slowly and the resulting mixture was stirred for 1 h. The reaction was quenched with water and diluted with EtOAc, the layers separated and the aqueous extracted with EtOAc three times. The combined organic portions were dried over MgSO$_4$, filtered and concentrated to afford the crude product as a viscous brown oil which was sonicated with water and then filtered to give 1-methyl-5-methoxyindoline-2,3-dione as a dark red solid (22.2 g, 63% after drying). $^1$H NMR (400 MHz, DMSO-d6) δ 7.25 (dd, J=8.6, 2.6 Hz, 1H), 7.12 (d, J=2.4 Hz, 1H), 7.07 (d, J=8.5 Hz, 1H), 3.76 (s, 3H), 3.10 (s, 3H).

A solution of 1-methyl-5-methoxyindoline-2,3-dione (22.2 g, 116 mmol) and hydrazine hydrate (50-60% grade, 7.3 mL, ca. 2 eq) in DMSO (42 mL) is heated to 140° C. in an oil bath. After 3 h, the mixture was cooled, diluted with water and EtOAc, the layers separated and the aqueous extracted with EtOAc four times (30 mL). The combined organic portions were washed with 1M H$_2$SO$_4$ twice, brine, and dried over MgSO$_4$, filtered and concentrated to yield the title compound as an orange solid (19.2 g, 93%). $^1$H NMR (400 MHz, MeOD) δ 6.96-6.95 (m, 1H), 6.89-6.84 (m, 2H), 3.78 (s, 3H), 3.53 (s, 2H), 3.19 (s, 3H). MS ESI 178.0 [M+H]$^+$, calcd for [C$_{10}$H$_{11}$NO$_2$+H]$^+$178.08.

1-(2-Methoxyethyl)indolin-2-one

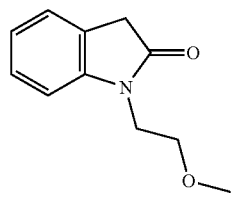

To a solution of isatin (2.94 g, 20 mmol) in DMF (40 mL) at 0° C. was added 60% NaH (1.00 g, 25 mmol) portionwise. After addition, the resulting mixture was stirred for 15 min at 0° C., then 1-bromo-2-methoxyethane (2.35 mL, 25 mmol) was added dropwise over 2 min. The resulting mixture was stirred for 10 min at 0° C., then O/N at rt, then cooled to 0° C., and quenched with saturated NH$_4$Cl, ice, and H$_2$O. The product was extracted with EtOAc (150 mL×2) and dried (Na$_2$SO$_4$). Removal of solvents gave a dark orange red liquid which was redissolved in DMSO (10 mL). Hydrazine hydrate (2 mL) was added dropwise over 7 min. After addition, the reaction mixture was stirred for 5 min at rt, then 2 h at 140° C. (oil temp.) before cooling to rt. Ice/H$_2$O (20 mL) was added, followed by 6 M HCl (7 mL, 42 mmol), and the resulting mixture was stirred for 30 min at rt. Additional ice/H$_2$O (40 mL) was added, and the mixture was extracted with EtOAc (50 mL×3). Purification by flash chromatogaphy (gradient: 0 to 40% EtOAc in hexane) afforded the title compound (orange liquid, 2.32 g, 61% over 2 steps). $^1$H NMR (400 MHz, DMSO-d6) δ 7.26-7.20 (m, 2H), 7.03 (d, J=8.0 Hz, 1H), 6.98 (t, J=7.4 Hz, 1H), 3.82 (t, J=5.6 Hz, 2H), 3.55 (s, 2H), 3.52 (t, J=5.8 Hz, 2H), 3.22 (s, 3H); MS ESI 191.8 [M+H]$^+$, calcd for [C$_{11}$H$_{13}$NO$_2$+H]$^+$192.1.

Preparation of Indazole Intermediates

6-Bromo-1H-indazole

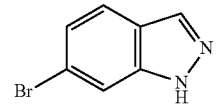

Method 1: Hydrazine hydrate (40 mL) was added dropwise to a solution of 4-bromo-2-fluorobenzaldehyde (40.6 g, 200 mmol) in DMSO (80 mL). The resulting mixture was heated in an oil bath set to 120° C. for 20 h, then allowed to cool and poured into an ice/water mixture (400 mL). After stirring for 30 min, the yellow precipitate was filtered, and washed successively with 2×100 mL portions each of water, 2.0 M aq. HCl, water, 0.5 M Na$_2$CO$_3$ and water. The solid was dried under low and then high vacuum (ca. 1 mbar) at room temperature (5 h) and at 70° C. (6 h) to afford the title compound (31.4 g, 80%) as a yellow powder. Spectral data matches literature values (K. Lukin, M. C. Hsu, D. Fernando, and M. R. Leanna, *J. Org. Chem.*, 2006, 71, 8166-8172).

Method 2: Modified workup procedure for the preparation of 6-bromo-1H-indazole: Hydrazine hydrate (10 mL) was added dropwise to a solution of 4-bromo-2-fluorobenzaldehyde (10 g, 49.3 mmol) in DMSO (20 mL). The resulting mixture was heated in an oil bath set to 120° C. Samples were taken periodically to monitor reaction progress by $^1$H and $^{19}$F NMR which indicated that upwards of 10 h (and probably upwards of 15 h) is required for complete reaction. After 20 h, the mixture was allowed to cool to around 40-50° C. Water (80 mL) was added slowly, resulting in formation of fine crystals. The solids were filtered, washed thoroughly with water, and dried under suction overnight. The crude product (6.9 g) was taken up in hot EtOAc (5 mL/g) and filtered to remove insoluble material. The solids were washed with further EtOAc (2 mL/g). The filtrate was concentrated to an EtOAc content of approx 4.5 mL/g, heated until all solids dissolved, then allowed to cool slowly to room temperature and then overnight in a standard fridge (ca. 4° C.). The resulting colourless crystals were filtered, washed with cold EtOAc and then dried under suction. Yield 4.75 g (49%). A second crop of crystals (0.64 g, 6.6%) was obtained. Spectral data matches literature values as above in Method 1.

Method 3: 4-Bromo-2-fluorobenzaldehyde (1.0 kg, 4.9 mol) and DMSO (2.0 L) were added to a 10 L jacketed vessel fitted with overhead stirrer, thermometer and water condenser. Hydrazine hydrate (1.0 L) was added in a thin stream to the resulting solution, a small exotherm being observed. The jacket temperature was raised to 120° C. and stirring continued for a period of 20 h. The mixture was cooled to around 45° C. Water (5.0 L) was added slowly, resulting in formation of fine crystals. Stirring was continued for a further 1 h at room temperature. The reaction mixture was drained from the vessel, and the solids filtered, washed thoroughly with water until filtrate pH was neutral, and dried under suction overnight. The crude product was taken up in hot EtOAc (5 mL/g) and filtered to remove insoluble material. The solids were washed with further EtOAc (2 mL/g based on crude product). The filtrate was concentrated to an EtOAc content of approx. 4.5 mL/g, heated until all solids dissolved, then allowed to cool slowly to room temperature and then overnight in a standard fridge (ca. 4° C.). The resulting colourless crystals were filtered, washed with cold EtOAc and then dried under suction. Yield 435 g (45%). No attempt was made to isolate further crops of material. Spectral data matches literature values as above in Method 1.

N1-Benzyl-6-bromo-1H-indazole and N2-benzyl-6-bromo-2H-indazole

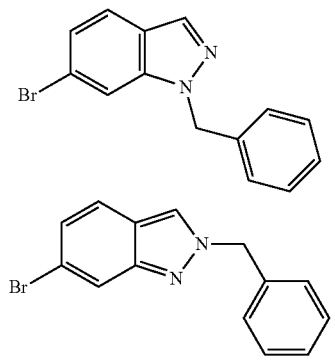

Method 1: A suspension of NaH (60 wt % in mineral oil, 5.6 g, 140.0 mmol) in dry THF (150 mL) was cooled in an ice bath, and a suspension of 6-bromo-1H-indazole (27.6 g, 140 mmol) in dry THF (150 mL) was added slowly. The liquid portion became red, but some solids remained. After 30 min, BnBr (17.1 mL, 147.4 mmol) was added, the cooling bath removed, and the mixture left to stir for 3 h at RT. $^1$H NMR of a sample showed a product ration of 1:1.7 (N1:N2) and incomplete conversion; additional NaH (1.0 g, 25.0 mmol) was added. After a further 1 h at RT and 1 h at 50° C., the mixture was concentrated and chromatographed directly on silica using a 4 cm diameter column with 1:3 EtOAc/cyclohexane as eluent. Only partial separation was achieved, and so the mixed fractions were re-purified on an 8 cm diameter column using approx. 0.5 kg of silica. Samples of both N1-Benzyl-6-bromo-1H-indazole (Rf 0.5, 7.9 g, 20%) and N2-benzyl-6-bromo-2H-indazole (Rf 0.45, 14.2 g, 35%) were isolated, along with some mixed fractions that were retained against future requirements. N1-Benzyl-6-bromo-1H-indazole: $^1$H NMR (400 MHz, CDCl$_3$) δ 8.00 (d, J=0.6 Hz, 1H), 7.58 (d, J=8.6 Hz, 1H), 7.52 (s, 1H), 7.36-7.20 (m, 4H), 7.20-7.15 (m, 2H), 5.53 (s, 2H). MS (ES+): 287 ($^{79}$Br, [M+H]$^+$), 289 ($^{81}$Br, [M+H]$^+$)]$^+$); calcd for [C$_{14}$H$_{11}$BrN$_2$+H]$^+$287.0 ($^{79}$Br). N2-benzyl-6-bromo-2H-indazole: $^1$H NMR (300 MHz, CDCl$_3$) δ 7.92-7.88 (m, 1H), 7.85 (s, 1H), 7.52-7.46 (m, 1H), 7.41-7.32 (m, 3H), 7.31-7.24 (m, 2H), 7.14 (dd, J=8.9, 1.6 Hz, 1H), 5.56 (s, 2H). MS (ES+): 287 ($^{79}$Br, [M+H]$^+$), 289 ($^{81}$Br, [M+H]$^+$); calcd for [C$_{14}$H$_{11}$BrN$_2$+H]$^+$287.0 ($^{79}$Br).

Method 2: A solution of 6-bromo-1H-indazole (0.1 g, 0.5 mmol) in dry DMSO (0.5 mL) was treated with KO$^t$Bu (67 mg, 0.6 mmol). After 10 min, BnCl (69 μL, 0.6 mmol) was added, and the resulting mixture left to stir at rt. After 4 h, a standard workup was carried out using sat. aq. NH$_4$Cl and EtOAc. $^1$H NMR of the crude product indicated complete conversion of starting material and a 2.5:1 ratio of the N1- and N2-benzylated products (entry 10 below).

Method 3: The crude 6-Bromo-1H-indazole (Method 3, 433 g) in DMSO (1.3 L) was treated with KOH (1.22 eq) and BnBr (1.22 eq). This did not go to completion by TLC, and so two further additions of reagents were made, BnBr (0.2 eq) and KOH (0.2 eq). This still did not go to completion, and so a standard aqueous workup was conducted, followed by treatment with 0.4 eq each BnBr (0.4 eq) and KOtBu (0.4 eq) in THF (1.5 L). When the reaction was complete as indicated by TLC, a standard aqueous workup was conducted yielding the crude product, which contained a number of non-polar impurities incorporating a benzyl fragment, but was used in the equilibration step without further purification (Method 3 below).

N1-Benzyl-6-bromo-1H-indazole via Equilibrium conversion of N2-benzyl-6-bromo-2H-indazole to N1-Benzyl-6-bromo-1H-indazole

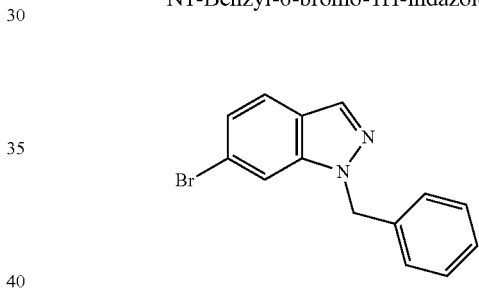

Method 1: N2-Benzyl-6-bromo-2H-indazole (1.0 g, 3.5 mmol, containing approx. 10% N1-isomer) and BnBr (0.42 mL) were placed in a tube and heated to 200° C. The mixture darkened rapidly. $^1$H NMR of a sample taken after 5 min indicated an N1:N2 ratio of 3.5:1, increasing to >10:1 in a further sample taken at 30 min. A further portion of starting material (9 g, 31.5 mmol) was then added, and heating continued. After 3 h, a similar ratio of isomers was obtained, which did not change significantly on heating overnight. Aqueous workup (acidic and basic washes) and passage through a short pad of silica failed to remove the blackened material, although NMR indicated moderate to good purity. Distillation at 175° C., ca. 1 mbar removed colored impurities.

Method 2: N2-Benzyl-6-bromo-2H-indazole (containing varying amounts of N1-isomer) and BnBr (20 mol %) were placed in a tube and heated to 150-160° C. for 6 h. Material prepared in this manner was used in a subsequent Suzuki reaction either with or without distillation at (175° C., ca. 1 mbar).

Method 3: BnBr (approx. 20 mol %) was added to the crude N1- and N2-benzyl-6-bromo-2H-indazoles from the reaction above (433 g) and the resulting mixture was heated for 5 h in an aluminium block set to 160° C. The crude mixture was already dark, so whether the mixture darkened further could not be determined. BnBr was removed by applying moderate vacuum (ca. 50 mbar) to the heated mixture. The residues were left to cool to around 40° C., then taken up in a mixture of cyclohexane and Et$_2$O (4:1) and washed with 10% aq. NaOH, half-sat. brine and brine. The organic portion was dried over MgSO$_4$, filtered through a short (approx. 2 cm) silica pad, eluting with further cyclohexane/ether, and concentrated to yield the crude material (734 g). $^1$H NMR indicated that the N2-isomer comprised <5% of the mixture, although the material contained a number of impurities carried over from the starting mixture. Half of this material was used directly in the subsequent Suzuki reaction described below (two portions, 153 g described). The remaining half of the material was distilled at 200° C., ~1 mbar to yield a semi-crude product (225.5 g, ~65% purity by weight as determined by $^1$H NMR, contaminant dibenzyl ether; calculated yield of desired product ~145 g, 45%).

N1-Benzyl-6-vinyl-1H-indazole

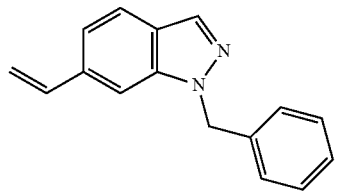 [SMILES: C=Cc1ccc2cnn(Cc3ccccc3)c2c1]

Method 1: A mixture of N1-Benzyl-6-bromo-1H-indazole (10.2 g, 35.5 mmol) and NaOH (4.3 g, 107 mmol) in THF/water (9:1, 350 mL) was purged with nitrogen. In a separate flask, Pd(OAc)$_2$ (0.16 g, 0.7 mmol, 2 mol %) and PPh$_3$ (0.37 g, 1.4 mmol, 4 mol %) were stirred together in nitrogen-purged dry THF (35 mL) for 10 min, forming a red solution with some suspended solids. Vinylboronic acid pinacol ester (7.5 mL, 44.4 mmol) and the catalyst solution were added to the reaction mixture, and the resulting solution purged once more with nitrogen. The mixture was warmed in an oil bath set to 65° C.; TLC indicated consumption of starting material within 7 h. The mixture was concentrated under reduced pressure to remove most of the THF, then diluted with water (50 mL), brine (50 mL) and EtOAc (250 mL). The layers were separated and the aqueous phase extracted with further EtOAc (4×50 mL). The combined organic portions were washed with brine, dried over Na$_2$SO$_4$, filtered and concentrated (at 70° C./20 mbar) to afford the crude product. This was chromatographed on silica using 10-20% EtOAc in cyclohexane to afford the title compound (7.5 g, 90%) as a yellow oil that solidified on standing. $^1$H NMR (400 MHz, CDCl$_3$) δ 7.98 (s, 1H), 7.63 (d, J=8.4 Hz, 1H), 7.29-7.19 (m, 5H), 7.18-7.13 (m, J=7.0 Hz, 2H), 6.75 (dd, J=17.6, 10.9 Hz, 1H), 5.76 (d, J=17.5 Hz, 1H), 5.53 (s, 2H), 5.26 (d, J=10.9 Hz, 1H). MS (ES+): 235 ([M+H]+); calcd for [C$_{16}$H$_{14}$N$_2$+H]$^+$235.1.

Method 2: using 4,4,6-Trimethyl-2-vinyl-1,3,2-dioxaborinane: A mixture of N1-Benzyl-6-bromo-1H-indazole (1.44 g, 5.0 mmol) and NaOH (0.4 g, 10.0 mmol) in THF/water (5:1, 15 mL) was purged with nitrogen. In a separate flask, Pd(OAc)$_2$ (11 mg, 0.05 mmol, 1 mol %) and PPh$_3$ (26 mg, 0.1 mmol, 2 mol %) were stirred together in nitrogen-purged THF (2.5 mL) for 10 min, forming a red solution with some suspended solids. The THF used was of HPLC grade and inhibitor free; the effect of lower grade or stabilized THF is not known. 4,4,6-Trimethyl-2-vinyl-1,3,2-dioxaborinane (1.12 mL, 6.5 mmol) and the catalyst solution were added to the reaction mixture, and the resulting solution purged once more with nitrogen. The mixture was warmed in an oil bath set to 65° C.; heating was continued for 24 h but the reaction is probably complete in fewer than 8 h. The crude mixture was then combined with a second, parallel reaction of the same scale where higher dilution had been used. The mixture was concentrated under reduced pressure to remove most of the THF, then diluted with water, brine and cyclohexane. The layers were separated and the aqueous phase extracted with further cyclohexane until TLC indicated all the desired product had been extracted (3-4 extracts). The combined organic portions were washed with brine, dried over MgSO$_4$, and then passed through a 1 cm pad of silica to remove baseline material. Any product remaining on the silica was eluted using 10% EtOAc in cyclohexane (Rf. 0.15 in this eluent). The combined eluate was concentrated to afford the title compound (2.05 g, 88%) as a yellow oil that solidified on standing and was of sufficient purity to use in subsequent reactions.

Method 3: N1-Benzyl-6-bromo-1H-indazole (half of the crude material obtained in method 3 above) was processed in two batches as follows: a mixture of crude N1-Benzyl-6-bromo-1H-indazole (153 g, containing a maximum of 0.5 mol assuming 100% yield in benzylation/equilibration) and NaOH (40 g, 1.0 mol) in THF/water (5:1, 1.5 L; HPLC grade inhibitor-free THF) was purged with nitrogen. In a separate flask, Pd(OAc)$_2$ (1.13 g, 5.0 mmol, 1 mol %) and PPh$_3$ (2.6 g, 10.0 mmol, 2 mol %) were stirred together in nitrogen-purged THF (250 mL) for 10 min, forming a red solution with some suspended solids. 4,4,6-Trimethyl-2-vinyl-1,3,2-dioxaborinane (112 mL, 0.65 mol) and the catalyst solution were added to the reaction mixture, and the resulting solution purged once more with nitrogen. The mixture was heated overnight in an oil bath set to 60° C. $^1$H NMR of a sample indicated that some starting material remained, and so additional vinyl donor (30 mL) was added to push to completion. Both batches of mixture were combined and the mixture was concentrated under reduced pressure to remove most of the THF, then diluted with water, brine and cyclohexane. The layers were separated and the aqueous phase extracted with further cyclohexane until TLC indicated all of the desired product had been extracted (total 3.5 L cyclohexane). The combined organic portions were washed with brine, dried over MgSO$_4$, and then passed through a 2 cm pad of silica to remove baseline material. Any product remaining on the silica was eluted using 10% EtOAc in cyclohexane (Rf. 0.15 in this eluent). The combined eluate was concentrated to afford 309 g of a crude oil comprising the title compound, a little of the diol derived from the vinyl donor, and a number of benzyl-containing impurities.

Method 4: A further reaction carried out using distilled N1-Benzyl-6-bromo-1H-indazole (64.3 g, 0.144 moles) afforded full conversion without the need for additional portion of vinyl donor, and gave semi-crude N1-Benzyl-6-vinyl-1H-indazole (55.5 g, quantitative) which was used without further purification below.

1-(4-Methoxybenzyl)-1H-indazole-6-carbaldehyde

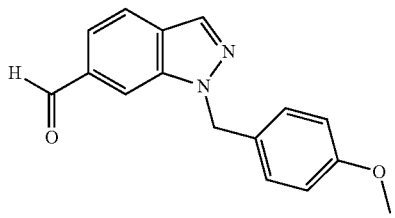 [SMILES: COc1ccc(Cn2ncc3ccc(C=O)cc32)cc1]

To a solution of 1H-indazole-6-carbaldehyde (1.5 g, 10.3 mmol) in DMF (10 mL) at 0° C. was added KO'Bu (1.4 g, 12.4 mmol) and let stir for 10 min. PMBCl (1.7 mL, 12.4 mmol) was then added and let slowly warm to room temperature. After 1.5 h the reaction was quenched with $NH_4Cl$. The product was extracted with $Et_2O$ and the organic layers was washed brine and then dried over $MgSO_4$. The solvent was removed and the crude material (mixture of N1 and N2 isomers) was dried under high vacuum. To the resulting residue was added PMBCl (0.70 mL, 5.15 mmol) and the mixture heated to 170° C. for 2.5 h. Cooled to room temperature and purified residue using Biotage Isolera (silica gel, 20-50% EtOAc in hexane) which gave the title compound (1.97 g, 72%). $^1H$ NMR (400 MHz, $CDCl_3$) δ 10.09 (s, 1H), 8.12 (s, 1H), 7.91 (s, 1H), 7.85 (d, J=8.4 Hz, 1H), 7.67 (d, J=8.4 Hz, 1H), 7.21 (d, J=8.5 Hz, 2H), 6.85 (d, J=8.6 Hz, 2H), 5.62 (s, 2H), 3.77 (s, 3H); MS ESI 266.9 $[M+H]^+$, calcd for $[C_{16}H_{14}N_2O_2+H]^+$ 267.1.

1-(4-Methoxybenzyl)-6-vinyl-1H-indazole

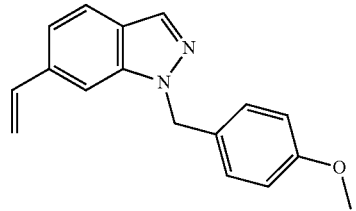 [SMILES: C=Cc1ccc2cnn(Cc3ccc(OC)cc3)c2c1]

An oven-dried flask under $N_{2\,(g)}$ was charged with NaH (60% wt) (592 mg, 14.8 mmol) and THF (30 mL) and the suspension cooled to 0° C. $CH_3PPh_3Br$ (5.29 g, 14.8 mmol) was added and stirred for 30 min at which time 1-(4-methoxybenzyl)-1H-indazole-6-carbaldehyde (1.97 g, 7.40 mmol) was added and the reaction was allowed to slowly warm to room temperature. After 2.5 h quenched with $NH_4Cl$ and extracted with $Et_2O$. The organic layers were washed with brine (2×) and dried over $MgSO_4$. The solvent was removed and the residue purified using Biotage Isolera (silica gel, 10-20% EtOAc in hexane) to give the title compound as a white solid (1.20 g, 61%); $^1H$ NMR (400 MHz, $CDCl_3$) δ 7.99 (s, 1H), 7.67 (d, J=8.8 Hz, 1H), 7.30-7.26 (m, 2H), 7.16 (d, J=8.3 Hz, 2H), 6.84-6.76 (m, 3H), 5.80 (d, J=17.5 Hz, 1H), 5.53 (s, 2H), 5.30 (d, J=10.9 Hz, 1H), 3.76 (s, 3H); MS ESI 264.9 $[M+H]^+$ calcd for $[C_{17}H_{16}N_2O+H]^+$ 265.1.

Preparation of Indazole Diols

1-(1-Benzyl-1H-indazol-6-yl)-ethane-1,2-diol

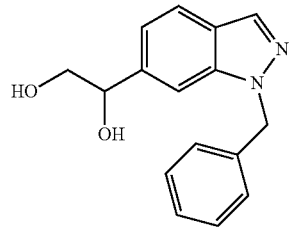

A sample of N1-benzyl-6-vinyl-1H-indazole (crude material, ~24 mmol) was stirred in a mixture of 'BuOH (25 mL), water (25 mL) and citric acid (10.1 g, 48.0 mmol). $K_2OsO_4\cdot2H_2O$ (44 mg, 0.12 mmol, 0.5 mol %) and N-methylmorpholine-N-oxide (3.1 g, 26.4 mmol) were added, and the resulting oily, biphasic mixture stirred overnight at rt. $^1H$ NMR of a sample showed approx. 40% conversion, and so the mixture was warmed to 50° C. (giving a single phase) for 7 h. Ethanol (50 mL) was added, and the mixture again left to stir overnight. Precipitated $OsO_2$ was removed by filtration through celite (washing with ethanol and ethyl acetate), and the filtrate was concentrated on a rotary evaporator. The residue was taken up in 1.0 M aq. HCl and EtOAc; the layers were separated and the aqueous phase extracted with further EtOAc. The combined organic portions were washed with brine, dried over $Na_2SO_4$, filtered and concentrated. The crude product was passed through a short silica plug, eluting with EtOAc, and concentrated to afford the title compound (6.26 g, 92% over two steps) as a reddish gum. $^1H$ NMR (400 MHz, $CDCl_3$) δ 7.96 (s, 1H), 7.65 (d, J=8.4 Hz, 1H), 7.38 (s, 1H), 7.27-7.18 (m, 3H), 7.16-7.09 (m, 2H), 7.04 (d, J=8.4 Hz, 1H), 5.50 (s, 2H), 4.86 (d, J=7.6 Hz, 1H), 3.78-3.68 (m, 1H), 3.60 (m, 1H), 3.46 (s, 1H), 2.84 (s, 1H). MS (ES+): 269 $([M+H]^+)$, calcd for $[C_{16}H_{16}N_2O_2+H]^+$ 269.1.

(S)-1-(N1-Benzyl-1H-indazol-6-yl)-ethane-1,2-diol

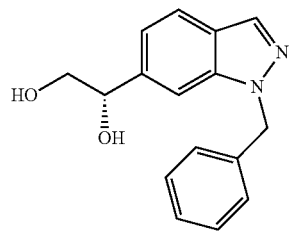 [SMILES: OC[C@@H](O)c1ccc2cnn(Cc3ccccc3)c2c1]

Method 1: $K_3Fe(CN)_6$ (16.7 g, 51.0 mmol), $K_2CO_3$ (7.05 g, 51.0 mmol), $(DHQ)_2PHAL$ (0.13 g, 0.17 mmol, 1 mol %) and $K_2OsO_4\cdot2H_2O$ (12.8 mg, 0.034 mmol, 0.2 mol %) were placed in a roundbottomed flask. A mixture of 'BuOH and water (1:1, 160 mL) was added, forming a clear, biphasic mixture on stirring. The mixture was cooled in an ice bath, resulting in partial precipitation, before addition of powdered N1-benzyl-6-vinyl-1H-indazole (4.0 g, 17.1 mmol). The resulting mixture was vigorously stirred in the ice bath for 5 h, at which point no further solid was visible and TLC indicated consumption of starting material. The reaction was quenched by addition of sodium metabisulfite (40 g), with the resulting effervescence causing the reaction mixture to overspill into the ice bath. The remaining material was added to the ice bath and the resulting mixture (containing approximately 1 L of water and ice) was stirred overnight, warming slowly. Celite and CH$_2$Cl$_2$ (200 mL) were added, the mixture thoroughly stirred and then filtered. The solids were washed thoroughly with further CH$_2$Cl$_2$ (2×50 mL). The biphasic filtrate was separated, and the aqueous layer extracted with CHCl$_3$ (4×50 mL). The combined organic portions were washed with brine, dried over MgSO$_4$, filtered and concentrated. The residue was taken up in EtOAc and filtered through a pad of silica (1 cm depth×8 cm diameter), eluting with further EtOAc, to remove baseline material. The eluate was concentrated and stripped with toluene to remove traces of $^t$BuOH. Finally, the residue was recrystallized from hot toluene (10 mL/g) to afford the title compound as white needles (3.87 g, 84%, 98.8% e.e.) with the major (S) enantiomer eluting at 16.8 min (Daicel Chiralpak IB (250×4.6 mm); isocratic 10% EtOH in n-heptane; 1 mL/min; ambient temperature (ca. 22° C.); Detection: 254, 230, 210 nm); From the racemic reference standard, the retention time of the (R) enantiomer was 14.8 min using this method and N1-benzyl-6-vinyl-1H-indazole eluted at 5.4 min. $^1$H NMR and mass spectral data were identical to racemic 1-(1-Benzyl-1H-indazol-6-yl)-ethane-1,2-diol obtained above. Optical Rotation: $[\alpha]^{22}_D = 13°$ (c 1.018, MeOH).

Method 2: Semi-crude N1-Benzyl-6-vinyl-1H-indazole (Method 4 above, 55.5 g) was dihydroxylated in a similar manner to afford, after recrystallization to obtain 2 crops of solid, pure (S)-1-(N1-Benzyl-1H-indazol-6-yl)-ethane-1,2-diol (38 g, quantitative).

Method 3: K$_3$Fe(CN)$_6$ (0.98 kg, 3 mol), K$_2$CO$_3$ (0.55 kg, 3 mol), (DHQ)$_2$PHAL (3.9 g, 5.0 mmol) and K$_2$OsO$_4$.2H$_2$O (0.37 g, 1 mmol) were placed in a 10 L clamp-top reaction vessel equipped with overhead stirrer. A mixture of $^t$BuOH and water (1:1, 7.5 L) was added, forming a clear, biphasic mixture on stirring. The mixture was cooled using a Haake EK90 chiller, resulting in partial precipitation, before addition of crude N1-benzyl-6-vinyl-1H-indazole (ca. 0.7-0.8 mol). The resulting mixture was vigorously stirred, but set solid as insufficient space was available for proper circulation in the cooling bath and the actual temperature dropped to around −20° C. when left over the weekend. Little conversion was evident. To speed up the reaction, further (DHQ)$_2$PHAL (2.5 mmol) and K$_2$OsO$_4$.2H$_2$O (0.5 mmol) were added, and the mixture let warm to approx. 10° C.; the reaction then proceeded satisfactorily. The reaction was quenched by portion-wise addition of sodium metabisulfite (1.5 kg). The mixture was stirred for 1 h at rt, becoming almost clear, then filtered through a pad of celite to remove precipitated OsO$_2$. The filtrate was extracted with CH$_2$Cl$_2$ (4 extracts, final volume 7 L), and the combined organic portions dried over MgSO$_4$, filtered and concentrated. The crude product was recrystallized from hot toluene (10 mL/g); two crops of the title compound were collected, of 98.7% and 98.0% e.e., totalling 163.7 g (55% from 6-bromo-1H-indazole).

(R)-1-(N1-Benzyl-1H-indazol-6-yl)-ethane-1,2-diol

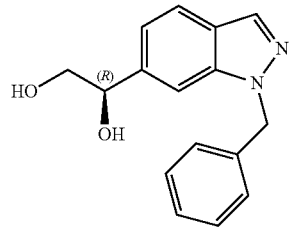

A similar procedure, carried out on N1-benzyl-6-vinyl-1H-indazole (0.89 g) using (DHQD)$_2$PHAL as ligand afforded the product of opposite configuration, (R)-1-(N1-Benzyl-1H-indazol-6-yl)-ethane-1,2-diol, in 94-96% e.e. The presence of an impurity that partially overlapped with the minor peak precluded a more accurate determination of e.e.

(S)-1-(1-(4-Methoxybenzyl)-1H-indazol-6-yl)ethane-1,2-diol

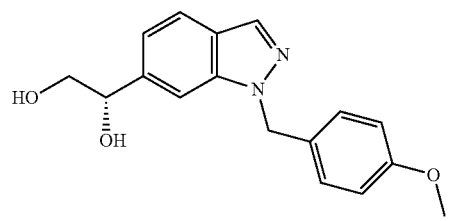 [SMILES: COc1ccc(Cn2ncc3ccc([C@H](O)CO)cc32)cc1]

A mixture of $^t$BuOH (10 mL), H$_2$O (10 mL), ACN (1.8 mL) and ADmix-α (1.28 g) was stirred for 5 min at room temperature and then cooled to 0° C. at which time 1-(4-methoxybenzyl)-6-vinyl-1H-indazole (320 mg, 1.21 mmol) was added. The reaction was stirred for 18 h and allowed to warm to room temperature. The reaction was then diluted with H$_2$O (25 mL) and extracted 3× with CH$_2$Cl$_2$. The organic layer was separated, washed with brine, dried over MgSO$_4$ and the solvent removed to give a white solid which was sonicated with hexane/Et$_2$O (1:1) and then filtered to give the title compound (270 mg, 75% after drying); $^1$H NMR (400 MHz, CD$_3$OD) δ 8.01 (s, 1H), 7.72 (d, J=8.2 Hz, 1H), 7.58 (s, 1H), 7.19-7.13 (m, 3H), 6.82 (d, J=8.4 Hz, 2H), 5.56 (s, 2H), 4.82-4.79 (m, 1H), 3.73 (s, 3H), 3.69-3.59 (m, 2H); MS ESI 298.9 [M+H]$^+$, calcd for [C$_{17}$H$_{18}$N$_2$O$_3$+H]$^+$ 299.14.

Preparation of Indazole Dimesylates

Methanesulfonic acid 2-(1-benzyl-1H-indazol-6-yl)-2-methanesulfonyloxy-ethyl ester

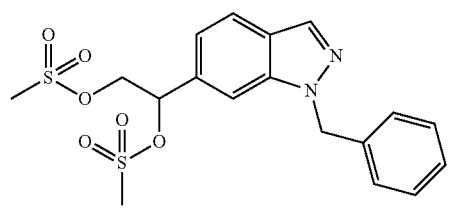 [SMILES: CS(=O)(=O)OCC(OS(C)(=O)=O)c1ccc2cnn(Cc3ccccc3)c2c1]

A solution of 1-(1-Benzyl-1H-indazol-6-yl)-ethane-1,2-diol (0.27 g, 1.0 mmol) and Et$_3$N (0.35 mL, 2.5 mmol) in dry CH$_2$Cl$_2$ (5 mL) was cooled in an ice bath before dropwise addition of MsCl (0.155 mL, 2.0 mmol) over 5 min. The resulting mixture was left to stir for 2 h, warming slowly to RT. After dilution with further CH$_2$Cl$_2$, the solution was washed quickly with 1.0 M aq. HCl (20 mL), sat. aq. NaHCO$_3$ (40 mL) and brine (20 mL), dried over Na$_2$SO$_4$, filtered and concentrated at 25° C. to afford the crude product. The crude product was part-purified by rapid column chromatography on silica using 1:1 Et$_2$O/CH$_2$Cl$_2$ as eluent, again concentrating at 25° C., giving the title compound (0.30 g, 71%) as an off-white, gummy foam. $^1$H NMR: (400 MHz, CDCl$_3$) δ 8.08 (s, 1H), 7.81 (d, J=8.3 Hz, 1H), 7.42 (s, 1H), 7.34-7.23 (m, 3H), 7.17 (dd, J=18.1, 7.6 Hz, 3H), 5.89 (dd, J=8.5, 3.2 Hz, 1H), 5.66 (d, J=15.8 Hz, 1H), 5.60 (d, J=15.8 Hz, 1H), 4.52 (dd, J=11.8, 8.6 Hz, 1H), 4.40 (dd, J=11.8, 3.2 Hz, 1H), 3.04 (s, 3H), 2.75 (s, 3H). MS (ES+): 425 ([M+H]$^+$), calcd for [C$_{18}$H$_{20}$N$_2$O$_6$S$_2$+H]$^+$ 425.1.

(S)-Methanesulfonic acid 2-(N1-benzyl-1H-indazol-6-yl)-2-methanesulfonyloxy-ethyl ester

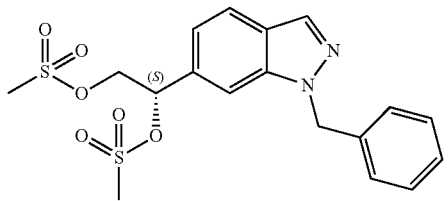

Method 1: A solution of (S)-1-(N1-Benzyl-1H-indazol-6-yl)-ethane-1,2-diol (3.75 g, 14.0 mmol, 98.8% e.e.) and Et$_3$N (4.9 mL, 35.0 mmol) in dry CH$_2$Cl$_2$ (350 mL) was cooled in an ice bath before dropwise addition of MsCl (2.17 mL, 28.0 mmol) over 10 min. The resulting mixture was left to stir for 30 min. After dilution with further CH$_2$Cl$_2$ (250 mL), the solution was washed with cold 1.0 M aq. HCl (2×50 mL), sat. aq. NaHCO$_3$ (50 mL) and brine (50 mL), then dried over Na$_2$SO$_4$. The solution was poured onto a short silica pad (1 cm depth×8 cm diameter) under suction. The initial filtrate did not contain any of the product; this was subsequently eluted with 1:1 Et$_2$O/CH$_2$Cl$_2$. The eluate was concentrated under reduced pressure to afford the title compound (5.98 g, ~quant.) as a white solid. $^1$H NMR and mass spectral data were identical to racemic methanesulfonic acid 2-(1-benzyl-1H-indazol-6-yl)-2-methanesulfonyloxy-ethyl ester obtained above. The e.e. of this batch of material was not determined at this stage but was carried forward to the next step. Optical Rotation: [α]$^{22}_D$=58° (c 0.73, CHCl$_3$).

Method 2: A solution of (S)-1-(N1-benzyl-1H-indazol-6-yl)-ethane-1,2-diol (134 g, 0.5 mol, ~98% e.e.) and Et$_3$N (174 mL, 1.25 mol) in CH$_2$Cl$_2$ (2.5 L) was cooled in an ice bath before slow addition of MsCl (81.3 mL, 1.05 mol) over approx. 1 h. The internal temperature increased to a maximum of 11° C. The resulting mixture was left to stir for 30 min. The reaction was quenched with cold 1.0 M aq. HCl (400 mL), the phases separated, and the organic phase washes with further cold 1.0 M aq. HCl, aq. NaHCO$_3$ and brine, then dried over MgSO$_4$. The solution was poured onto a short silica pad under suction. Some of the product eluted from the silica during this filtration, and the remainder was eluted using 1:1 Et$_2$O/CH$_2$Cl$_2$ (2 L). The eluate was concentrated under reduced pressure to afford a hard white solid. This was triturated with Et$_2$O (800 mL) overnight. The fine white powder was collected by filtration and washed with further Et$_2$O (2×100 mL) to yield the title compound (184.2 g, 87%, 99% e.e.) with the major (S) enantiomer eluting at 13.4 min (Daicel Chiralpak IB (250×4.6 mm); isocratic 30% EtOH in n-heptane; 1 mL/min; ambient temperature (ca. 22° C.); Detection: 254, 230, 210 nm); From the racemic reference standard, the retention time of the (R) enantiomer was 14.4 min using this method. The filtrate contained only a small quantity of product of low e.e. and was discarded.

(S)-1-(1-(4-Methoxybenzyl)-1H-indazol-6-yl)ethane-1,2-diyl dimethanesulfonate

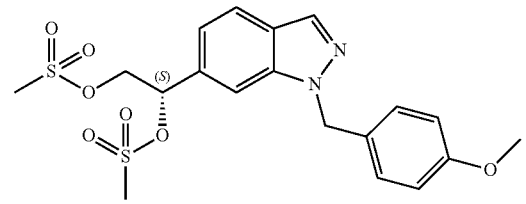

Methanesulfonyl chloride (0.88 mL, 11.3 mmol) was added dropwise to a solution of (S)-1-(1-(4-methoxybenzyl)-1H-indazol-6-yl)ethane-1,2-diol (1.68 g, 5.63 mmol), Et$_3$N (2.0 mL, 14.1 mmol) and CH$_2$Cl$_2$ (30 mL) at 0° C. After 1 h diluted with CH$_2$Cl$_2$ (100 mL) and washed with 0.5 M HCl, saturated aqueous NaHCO$_3$, brine, and then dried over MgSO$_4$. After the solvent was removed, purification using Biotage Isolera (silica gel, 50-66% EtOAc in hexane) gave the title compound as a sticky white solid (2.13 g, 83%); $^1$H NMR (400 MHz, CDCl$_3$) δ 8.05 (s, 1H), 7.78 (d, J=8.4 Hz, 1H), 7.42 (s, 1H), 7.18-7.12 (m, 3H), 6.82 (d, J=8.5 Hz, 2H), 5.90-5.87 (m, 1H), 5.59-5.50 (m, 2H), 4.55-4.50 (m, 1H), 4.42-4.38 (m, 1H), 3.76 (s, 3H), 3.04 (s, 3H), 2.77 (s, 3H); MS ESI 455.1 [M+H]$^+$, calcd for [C$_{19}$H$_{22}$N$_2$O$_7$S$_2$+H]$^+$ 455.1.

Preparation of Racemic Indazolyl-Spiro-Cyclopropane-Indolinones Reference Standards (1R*,2S*)-1'-benzyl-2-(1-benzyl-1H-indazol-6-yl)spiro[cyclopropane-1,3'-indolin]-2'-one

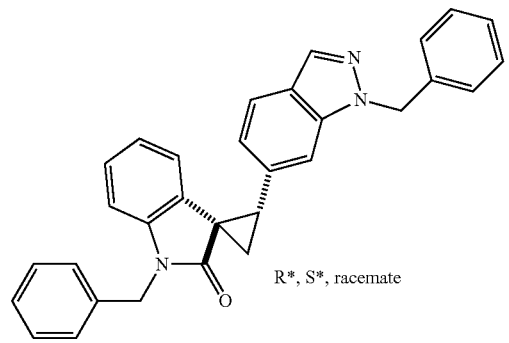

A solution of N-benzyl-oxindole (45 mg, 0.2 mmol) in dry THF (1 mL) was cooled in an ice bath before addition of NaH (60 wt % in mineral oil, 24 mg, 0.6 mmol); the solution quickly became a deep purple. A solution of racemic dimesylate (85 mg, 0.2 mmol, previously stripped twice with dry THF) in dry THF (1.5 mL) was added dropwise over 5 min. TLC indicated rapid conversion to a single compound with Rf 0.45 (25% EtOAc/cyclohexane, eluted twice; starting materials Rf 0.5 & Rf 0.2). The reaction mixture was left to stir overnight, warming slowly; no further change was observed by TLC and the purple color persisted. The mixture was diluted with water (10 mL), brine (10 mL) and EtOAc (25 mL), the phases separated and the aqueous layer extracted with further EtOAc (25 mL). The combined organic portions were washed with brine, dried over $Na_2SO_4$, filtered and concentrated to afford a crude product that, by $^1H$ NMR, appeared to consist almost exclusively of the title compound. The crude product was chromatographed on silica using 25-50% EtOAc/cyclohexane, concentrated and stripped with $Et_2O$/cyclohexane to afford the title compound (75 mg, 82%) as an off-white solid. $^1H$ NMR: (400 MHz, $CDCl_3$) δ 7.99 (s, 1H), 7.60 (d, J=8.3 Hz, 1H), 7.36-7.20 (m, 8H), 7.19 (s, 1H), 7.15-7.10 (m, J=6.4 Hz, 2H), 6.99 (td, J=7.8, 0.9 Hz, 1H), 6.92 (d, J=8.3 Hz, 1H), 6.74 (d, J=7.8 Hz, 1H), 6.50 (t, J=7.4 Hz, 1H), 5.76 (d, J=7.3 Hz, 1H), 5.61 (d, J=15.8 Hz, 1H), 5.53 (d, J=15.8 Hz, 1H), 5.08 (d, J=15.6 Hz, 1H), 4.97 (d, J=15.7 Hz, 1H), 3.48 (t, J=8.5 Hz, 1H), 2.28 (dd, J=9.0, 4.5 Hz, 1H), 2.02 (dd, J=8.0, 4.6 Hz, 1H). MS (ES+): 456 ([M+H]$^+$), calcd for $[C_{31}H_{25}N_3O+H]^+$ 456.2.

(1R*,2S*)-2-(3-iodo-1H-indazol-6-yl)spiro[cyclopropane-1,3'-indolin]-2'-one

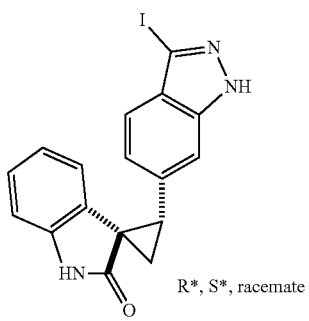

R*, S*, racemate

To a solution of 1H-indazole-6-carbaldehyde (2.00 g, 13.7 mmol), $K_2CO_3$ (3.79 g, 27.4 mmol) in DMF (15 mL) was added dropwise a solution of $I_2$ (5.91 g, 23.3 mmol) in DMF (15 mL) and the reaction allowed to stir for two h. An aqueous solution consisting of $Na_2S_2O_4$ (3.30 g)/$K_2CO_3$ (0.20 g)/$H_2O$ (30 mL) was then added and the solution stirred for one h. The product was then precipitated by pouring the solution over ice-water (300 mL) and collected by vacuum filtration to give 3-iodo-1H-indazole-6-carbaldehyde (beige powder, 3.02 g, 81%). $^1H$ NMR (400 MHz, $CD_3OD$) δ 10.11 (s, 1H), 8.11 (s, 1H), 7.74 (d, J=8.34 Hz, 1H), 7.62 (d, J=8.34 Hz, 1H); MS ESI 272.9 [M+H]$^+$, calcd for $[C_8H_5IN_2O+H]^+$ 272.95.

To a mixture of 3-iodo-1H-indazole-6-carbaldehyde (1.360 g, 5 mmol) and 2-oxindole (732 g, 5.5 mmol) in MeOH (25 mL) was added piperidine (0.1 mL, 1 mmol). The resulting mixture was refluxed (oil temp. 75° C.) for 90 min, then cooled to rt. The resulting precipitates were collected by suction filtration and dried to give (E/Z)-3-((3-iodo-1H-indazol-6-yl)methylene)-indolin-2-one as yellow solid (E:Z=5:1, 1.86 g). The mixture was used as an intermediate without purification of the isomers, or alternatively the pure E isomer could be purified by dissolving in THF (1.57 g in 46.85 mL) at room temperature. Hexane (146.8 mL) was added to the clear solution with stirring to give a yellow precipitate. The solid suspension was heated to 70° C. for 30 min & then cooled to room temperature. The yellow solid was filtered and washed with hexane (3.14 mL) to give (E)-3-((3-iodo-1H-indazol-6-yl)methylene)-indolin-2-one (1.22 g, 79%). $^1H$ NMR (400 MHz, $d_6$-DMSO) δ 13.71 (s, 1H), 10.64 (s, 1H), 7.88 (s, 1H), 7.77 (s, 1H), 7.57-7.46 (m, 3H), 7.23 (t, J=7.6 Hz, 1H), 6.87 (d, J=8.0 Hz, 1H), 6.83 (d, J=7.6 Hz, 1H); MS ESI 388.0 [M+H]$^+$, calcd for $[C_{16}H_{10}IN_3O+H]^+$ 387.99.

Sodium hydride (433.8 mg, 10.85 mmol) (60% dispersion in oil) added to anhydrous THF (7.0 ml) at room temperature. Then trimethylsulfoxonium iodide (795.7 mg, 3.62 mmol) was added to the suspension at the same temperature. The mixture was stirred for 15 min after which time a solution of (E/Z)-3-((3-iodo-1H-indazol-6-yl)methylene)-indolin-2-one (700 mg, 1.8 mmol) in THF (20.0 ml) was added. The solution was stirred at 50° C. for 6 h prior to quenching the reaction over 10% $NH_4Cl$ solution (40 mL) at room temperature. The product was extracted with ethyl acetate (20 mL, then 10 mL), dried over anhydrous $Na_2SO_4$ and concentrated to dryness. The title compound was isolated by adding toluene (21 ml) and collecting the solid (375 mg, 52%). The distereomeric mixture (375 mg) was purified by leaching with ethyl acetate (21 mL) at 55° C. for 2 h to give off-white solid (224 mg, 31%). $^1H$ NMR (400 MHz, $d_6$-DMSO) δ 13.47 (s, 1H), 10.62 (s, 1H), 7.47 (s, 1H), 7.30 (d, J=8.0 Hz, 1H), 7.02-6.98 (m, 2H), 6.84 (d, J=7.6 Hz, 1H), 6.53 (t, J=7.6 Hz, 1H), 5.97 (d, J=7.6 Hz, 1H), 3.18 (q, J=8.4 Hz, 1H), 2.31 (dd, J=7.2, 4.8 Hz, 1H), 1.98 (dd, J=8.8, 4.8 Hz, 1H); MS ESI 402.0 [M+H]$^+$, calcd for $[C_{17}H_{12}IN_3O+H]^+$ 402.0.

(1R*,2S*)-2-(1H-indazol-6-yl)spiro[cyclopropane-1,3'-indolin]-2'-one

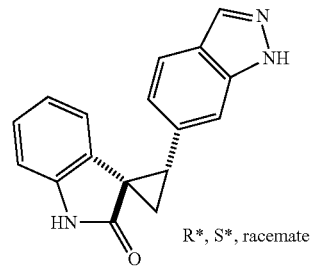

R*, S*, racemate

According to the method described for (E)-3-((3-iodo-1H-indazol-6-yl)methylene)-indolin-2-one, oxindole (67 mg, 0.216 mmol) and 1H-indazole-6-carbaldehyde (73 mg, 0.238 mmol) gave (E)-3-((1H-indazol-6-yl)methylene)indolin-2-one (32 mg, 51%). $^1H$ NMR (400 MHz, $CD_3OD$) δ 8.14 (s, 1H), 7.91 (d, J=8.5 Hz, 1H), 7.89 (s, 2H), 7.65 (d, J=7.6 Hz, 1H), 7.47 (d, J=8.4 Hz, 1H), 7.25 (t, J=7.7 Hz, 1H), 6.93 (d, J=7.8 Hz, 1H), 6.87 (t, J=7.6 Hz, 1H); MS ESI 262.0 [M+H]$^+$, calcd for $[C_{16}H_{11}N3O+H]^+$ 262.10.

To a solution of trimethylsulfoxonium iodide (264 mg, 1.2 mmol) in anhydrous DMF (40 mL) was added sodium hydride (60% dispersion in oil) (140 mg, 3.48 mmol) at 0° C. The mixture was stirred for 15 min after which time (E)-3-((1H-indazol-6-yl)methylene)indolin-2-one (151 mg, 0.58 mmol) was added. The solution was stirred overnight at rt. The reaction was quenched with sat. NH$_4$Cl solution (10 mL), extracted with EtOAc (4×50 mL), dried over MgSO$_4$ and concentrated to dryness. The major diastereomer was isolated by silica gel chromatography (50% EtOAc in hexane) as a beige solid (44 mg, 28%). $^1$H NMR (400 MHz, d$_6$-DMSO) δ 13.01 (s, 1H), 10.61 (d, J=8.3 Hz, 1H), 8.01 (s, 1H), 7.63 (d, J=8.3 Hz, 1H), 7.44 (s, 1H), 6.99 (t, J=7.5 Hz, 1H), 6.92 (d, J=8.0 Hz, 1H), 6.84 (d, J=8.0 Hz, 1H), 6.51 (t, J=7.0 Hz, 1H), 5.98 (d, 8.0 Hz, 1H), 3.20-3.17 (m, 1H), 2.30-2.26 (m, 1H), 2.00-1.95 (m, 1H); MS ESI 276.1 [M+H]$^+$, calcd for [C$_{17}$H$_{13}$N$_3$O+H]$^+$276.3.

(1R*,2S*)-5'-fluoro-2-(3-iodo-1H-indazol-6-yl)spiro[cyclopropane-1,3-indolin]-2'-one

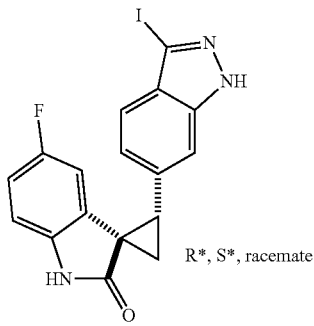

A round bottom flask was charged with 5-fluoroindolin-2-one (100 mg, 0.661 mmol), 3-iodo-1H-indazole-6-carbaldehyde (180 mg, 0.661 mmol), piperidine (13 uL, 0.027 mmol) and methanol (7.5 mL). The reaction was then heated to 60° C. for 3 h prior to cooling the reaction mass to room temperature. Filtration and washing with methanol (0.50 mL×2) gave (Z)-5-fluoro-3-((3-iodo-1H-indazol-6-yl)methylene)indolin-2-one as a yellow solid (260 mg, 96%). $^1$H NMR (400 MHz, d$_6$-DMSO) δ 13.82 (s, 1H), 10.72 (s, 1H), 9.00 (s, 1H), 8.06 (s, 1H), 7.98 (d, J=8.8 Hz, 1H), 7.71 (s, J=8.8 Hz, 1H), 7.48 (d, J=8.8 Hz, 1H), 7.07-7.02 (m, 1H), 6.81 (d, J=4.4 Hz, 1H).

Trimethylsulfoxonium iodide (173.8 mg, 0.789 mmol) was added to a suspension of sodium hydride (94.76 mg, 4.12 mmol) (60% dispersion in oil) in THF (4.0 mL) at room temperature. The mixture was stirred for 15 min after which time a solution of (Z)-5-fluoro-3-((3-iodo-1H-indazol-6-yl)methylene)indolin-2-one (160 mg, 0.394 mmol) in THF (2.4 mL) was added. The solution was stirred at 50° C. for 7 h prior to quenching the reaction mass over 10% NH$_4$Cl solution (15 mL) at room temperature. The product was extracted using ethyl acetate (15 mL×2) and the organic layer was dried over Na$_2$SO$_4$ and evaporated in vacuo. Trituration with hexane (5 mL) gave the title compound as a cream solid (89 mg, 53.7%). $^1$H NMR (400 MHz, d$_6$-DMSO) δ 13.50 (s, 1H), 10.65 (s, 1H), 7.50 (s, 1H), 7.31 (d, J=8.4 Hz, 1H), 7.00 (d, J=8.4 Hz, 1H), 6.85-6.81 (m, 2H), 5.81 (d, J=8.4 Hz, 1H), 3.22 (m, 1H), 2.43 (m, 1H), 2.01 (m, 1H); MS ESI 420.0 [M+H]$^+$, calcd for [C$_{17}$H$_{11}$FIN3O+H]$^+$ 420.0.

(1R*,2S*)-2-(3-iodo-1H-indazol-6-yl)-5'-methoxspiro[cyclopropane-1,3'-indolin]-2'-one

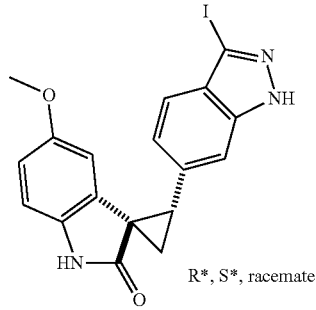

A round bottom flask was charged with 5-methoxyoxindole (commercial reagent from Prime Organics, 300 mg, 1.84 mmol), 3-iodo-1H-indazole-6-carbaldehyde (500 mg, 1.84 mmol), piperidine (20 uL, 0.18 mmol) and MeOH (7 mL). The reaction was then heated to 60° C. for 4 h. A bright red precipitate formed which was further precipitated by cooling to room temperature. The red powder was then filtered and washed with MeOH giving (E/Z)-3-((3-iodo-1H-indazol-6-yl)methylene)-5-methoxyindolin-2-one (658 mg, 86%, as a mixture of (E)- and (Z)-isomers, 84:16 by $^1$H NMR). $^1$H NMR (400 MHz, d$_6$-DMSO) δ 13.78 (br. s, 1H), 10.50 (s, 1H), 9.01 (s, 1H), 8.00 (s, 1H), 8.00 (d, J=8.3 Hz, 1H), 7.48 (d, J=8.3 Hz, 1H), 7.45 (d, J=2.1 Hz, 1H), 6.81 (dd, J=4.1, 2.2 Hz, 1H), 6.73 (d, J=8.4 Hz, 1H), 3.77 (s, 3H); MS ESI 418.0 [M+H]$^+$, calcd for [C$_{17}$H$_{12}$IN$_3$O$_2$+H]$^+$ 418.00.

To a solution of NaH (380 mg, 9.5 mmol) in DMF (8 mL) at 0° C. was added trimethylsulfoxonium iodide (694 mg, 3.15 mmol). The resulting mixture was stirred at rt for 30 min followed by the addition of (E/Z)-3-((3-iodo-1H-indazol-6-yl)methylene)-5-methoxyindolin-2-one (658 mg, 1.6 mmol, E/Z ratio 84:16) in DMF (2 mL). The reaction mixture was stirred at rt for 18 h. The reaction was cooled to 0° C. and quenched with saturated NH$_4$Cl. The mixture was extracted with EtOAc and the combined organic extracts were washed with brine, dried over MgSO$_4$ and concentrated to give a yellow viscous oil. The crude product was purified by silica gel chromatography (95:5 CH$_2$Cl$_2$/MeOH) to yield a yellow solid, which was then triturated with a 1:1 mixture of hexane and EtOAc to give the title compound as a white powder (471 mg, 69%). A mixture of diastereomers (88:12 by $^1$H NMR) was obtained. The compound was purified by crystallization from methanol to give the pure (1R*,2S*) diastereomer. $^1$H NMR (400 MHz, d$_6$-DMSO) δ 13.48 (s, 1H), 10.43 (s, 1H), 7.49 (s, 1H), 7.33 (d, J=8.4 Hz, 1H), 7.02 (d, J=8.4 Hz, 1H), 6.74 (d, J=8.4 Hz, 1H), 6.57 (dd, J=8.4, 2.4 Hz, 1H), 5.62 (d, J=2.4 Hz, 1H), 3.29 (s, 3H), 3.18 (t, J=8.2 Hz, 1H), 2.34 (dd, J=7.8, 4.6 Hz, 1H), 1.98 (dd, J=9.2, 4.8 Hz, 1H); MS ESI 432.1 [M+H]$^+$, calcd for [C$_{18}$H$_{14}$IN$_3$O$_2$+H]$^+$432.0.

61
(1R*,2S*)-2-(3-iodo-H-indazol-6-yl)-5'-methylspiro[cyclopropane-1,3'-indolin]-2'-one

62
(1R*,2S*)-2-(3-iodo-1-indazol-6-yl)-5'-methoxy-1'-methylspiro[cyclopropane-1,3'-indolin]-2'-one

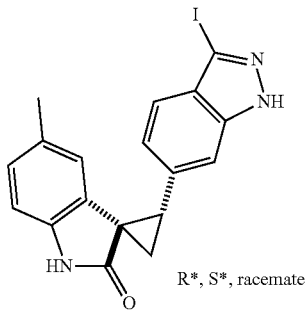

R*, S*, racemate

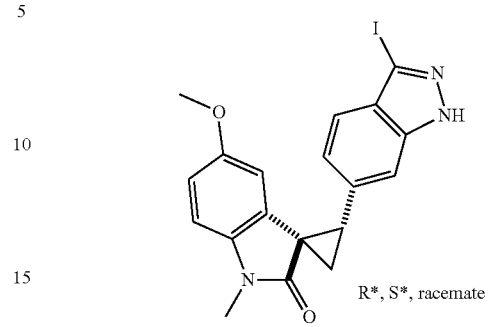

R*, S*, racemate

Using the method for the preparation of (1R*,2S*)-2-(3-iodo-1H-indazol-6-yl)spiro[cyclopropane-1,3'-indolin]-2'-one, with the exception that the cyclopropanation step was carried out at 60° C. for 1 h, 5-methylindolin-2-one (772 mg, 5.25 mmol) and 3-iodo-1H-indazole-6-carbaldehyde (1.36 g, 5 mmol), gave the title compound (yellow solid, 2.06 g, 99% over 2 steps, 6:1 mixture of diastereomers). $^1$H NMR (400 MHz, DMSO-d6) δ 13.43 (s, 1H), 10.51 (s, 1H), 7.47 (s, 1H), 7.32 (d, J=8.4 Hz, 1H), 7.02 (d, J=8.8 Hz, 1H), 6.81 (d, J=8.4 Hz, 1H), 6.73 (d, J=7.6 Hz, 1H), 5.86 (s, 1H), 3.18 (t, J=8.2 Hz, 1H), 2.30-2.20 (m 1H), 2.00-1.90 (m, 1H), 1.85 (s, 3H); MS ESI 416.1 [M+H]$^+$, calcd for [C$_{18}$H$_{14}$IN$_3$O+H]$^+$416.0.

A dry round-bottom flask was charged with NaH (60% wt) (64 mg, 1.61 mmol) and toluene (2.0 mL). The suspension was heated to 100° C. and then 5-methoxyindolin-2-one (250 mg, 1.53 mmol) was added. After 30 min at 100° C. Me$_2$SO$_4$ (0.16 mL, 1.68 mmol) was added and the temperature maintained at 100° C. for 2.5 h. The reaction was cooled to room temperature and the solvent removed. The residue was purified by column chromatography (silica gel, 25-33% EtOAc in hexane) to give 5-methoxy-1-methylindolin-2-one (beige solid, 144 mg, 53%); MS ESI 164.1 [M+H]$^+$, calcd for [C$_9$H$_9$NO$_2$+H]$^+$164.07.

A vial was charged with 5-methoxy-1-methylindolin-2-one (144 mg, 0.813 mg), 3-iodo-1H-indazole-6-carbaldehyde (221 mg, 0.813 mmol), MeOH (4.0 mL), and piperidine (7 uL, 0.081 mmol). The mixture was reacted at 50° C. for 18 h. The resulting orange product precipitate was filtered washing with MeOH and then dried under high vacuum. The orange solid was then added to a suspension of 60% NaH (155 mg, 3.87 mmol) and trimethylsulfoxonium iodide (284 mg, 1.29 mmol) in DMF (3.0 mL) that had been pre-stirred at room temperature for 30 min. This mixture was heated to 40° C. for 2 h. The reaction was cooled to 0° C., quenched with NH$_4$Cl (sat.) (2 mL) and extracted with EtOAc (100 mL). The organic layer was separated, washed with brine (10 mL) and dried over MgSO$_4$. The solvent was removed and the residue purified by column chromatography (silica gel, 16-25% acetone in hexane) to give the title compound (pink solid, 205 mg, 57% over 2 steps); MS ESI 446.0 [M+H]$^+$, calcd for [C$_{19}$H$_{16}$IN$_3$O$_2$+H]$^+$446.04.

(1R*,2S*)-2-(3-iodo-1H-indazol-6-yl)-1'-methylspiro[cyclopropane-1,3'-indolin]-2'-one

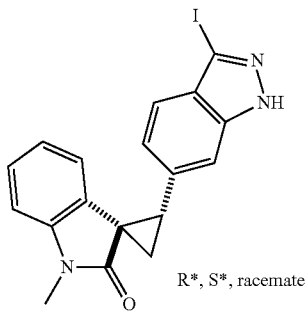

R*, S*, racemate

According to the method described for (E)-3-((3-iodo-1H-indazol-6-yl)methylene)-indolin-2-one except substituting 3-iodo-1H-indazole-6-carbaldehyde (462 mg, 1.70 mmol) and 1-methylindolin-2-one (250 mg, 1.70 mmol), (E)-3-((3-iodo-1H-indazol-6-yl)methylene)-1-methylindolin-2-one was obtained (yellow-orange solid, 545 mg, 80%); MS ESI 402.2 [M+H]$^+$, calcd for [C$_{17}$H$_{12}$IN$_3$O+H]$^+$402.01.

The title compound was synthesized according to the method of (1R*,2S*)-2-(3-iodo-1H-indazol-6-yl)spiro[cyclopropane-1,3'-indolin]-2'-one, except substituting (E)-3-((3-iodo-1H-indazol-6-yl)methylene)-1-methylindolin-2-one (545 mg, 1.36 mmol) to give the title compound as a 9:1 mixture of diastereomers (405 mg, 72%); MS ESI 416.0 [M+H]$^+$, calcd for [C$_{18}$H$_{14}$IN$_3$O+H]$^+$416.03.

(1R*,2S*)-2-(3-iodo-1H-indazol-6-yl)-1'-(2-methoxyethyl)spiro[cyclopropane-1,3'-indolin]-2'-one

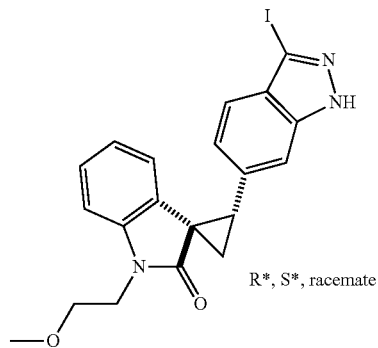

R*, S*, racemate

Using the method for the preparation of (1R*,2S*)-2-(3-iodo-1H-indazol-6-yl)spiro[cyclopropane-1,3'-indolin]-2'-one, with the exception that the cyclopropanation step was carried out at rt for 10 min, 1-(2-methoxyethyl)indolin-2-one (382 mg, 2 mmol) and 3-iodo-1H-indazole-6-carbaldehyde (544 mg, 2 mmol), gave the title compound (light beige solid, 750 mg, 82% over 2 steps, 6:1 mixture of diastereomers). $^1$H NMR (400 MHz, DMSO-d6) δ 13.48 (s, 1H), 7.47 (s, 1H), 7.30 (d, J=7.8 Hz, 1H), 7.10-7.05 (m, 2H), 6.98 (d, J=8.3 Hz, 1H), 6.64-6.56 (m, 1H), 6.01 (d, J=7.3 Hz, 1H), 3.98-3.92 (m, 2H), 3.63-3.57 (m, 2H), 3.25 (s, 3H and t, J=8.6 Hz, 1H overlapping; total 4H), 2.37 (t, J=6.1 Hz, 1H), 2.05 (dd, J=9.0, 5.0 Hz, 1H); MS ESI 460.1 [M+H]$^+$, calcd for [C$_{20}$H$_{18}$IN$_3$O$_2$+H]$^+$460.0

Preparation of Chiral
Indazolyl-Spiro-Cyclopropane-Indolinones

Example 1

(1R,2S)-2-(3-iodo-1H-indazol-6-yl)spiro[cyclopropane-1,3'-indolin]-2'-one

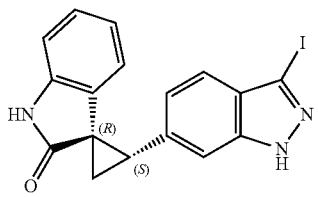

A. (1R,2S)-1'-benzyl-2-(1-benzyl-1H-indazol-6-yl)spiro[cyclopropane-1,3'-indolin]-2'-one

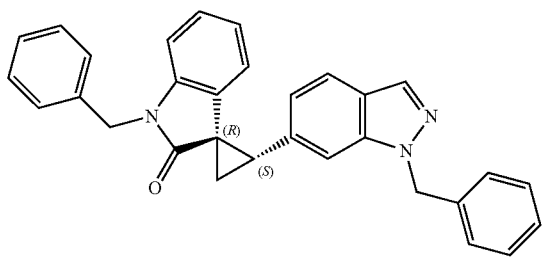

Method 1: A solution of N-benzyl-oxindole (3.57 g) in dry THF (120 mL) was cooled in an ice bath before addition of NaH (60 wt % in mineral oil, 1.92 g, 48.0 mmol) in four portions; the solution quickly became a deep purple. After 30 min, a solution of (S)-methanesulfonic acid 2-(N1-benzyl-1H-indazol-6-yl)-2-methanesulfonyloxy-ethyl ester (6.79 g, 16.0 mmol, ~98.5% e.e., previously stripped twice with dry THF) in dry THF (80 mL) was added by syringe pump over a period of 1 h. TLC indicated rapid conversion to a single compound with Rf 0.45 (25% EtOAc in cyclohexane, eluted twice; starting materials Rf 0.5 & Rf 0.2). After stirring for 2 h, the mixture was poured into sat. aq. NH$_4$Cl (50 mL), diluted with water (50 mL), and EtOAc (100 mL). The phases were separated and the aqueous layer extracted with further portions of EtOAc (4×50 mL). The combined organic portions were washed with brine, dried over Na$_2$SO$_4$, filtered and concentrated to afford a crude product that, by $^1$H NMR, appeared to consist almost exclusively of the title compound. The crude product was passed through a short silica pad (1 cm depth×5 cm diameter), eluting with 1:1 EtOAc in cyclohexane. The residue was triturated with n-heptane (3×50 mL) to remove mineral oil, and stripped with toluene to afford the title compound (7.0 g, up to 90% yield) as a glassy solid that contained some solvent. HPLC indicated an optical purity of 98% e.e. with the major (1R,2S) enantiomer eluting at 13.3 min (Daicel Chiralpak IA, 250×4.6 mm; isocratic 10% EtOH in n-heptane; 1 mL/min; ambient temperature (ca. 22° C.); Detection: 254, 230, 210 nm); From the racemic reference standard, the retention time of the (1S,2R) enantiomer was 12.1 min using this method. $^1$H NMR (400 MHz, CDCl$_3$) δ 7.99 (s, 1H), 7.60 (d, J=8.3 Hz, 1H), 7.36-7.20 (m, 8H), 7.19 (s, 1H), 7.15-7.10 (m, J=6.4 Hz, 2H), 6.99 (td, J=7.8, 0.9 Hz, 1H), 6.92 (d, J=8.3 Hz, 1H), 6.74 (d, J=7.8 Hz, 1H), 6.50 (t, J=7.4 Hz, 1H), 5.76 (d, J=7.3 Hz, 1H), 5.61 (d, J=15.8 Hz, 1H), 5.53 (d, J=15.8 Hz, 1H), 5.08 (d, J=15.6 Hz, 1H), 4.97 (d, J=15.7 Hz, 1H), 3.48 (t, J=8.5 Hz, 1H), 2.28 (dd, J=9.0, 4.5 Hz, 1H), 2.02 (dd, J=8.0, 4.6 Hz, 1H). MS (ES+): 456 ([M+H]$^+$), calcd for [C$_{31}$H$_{25}$N3O+H]$^+$456.2.

Method 2: In a separate set of individual experiments carried out in a similar manner as Method 1 but not performing any column chromatography, using between on 20-45 g of (S)-methanesulfonic acid 2-(N1-benzyl-1H-indazol-6-yl)-2-methanesulfonyloxy-ethyl ester per batch, a total of 133.8 g, 315 mmol was carried forward. Some batches were combined and passed through a silica plug to remove traces of baseline material before use, but this didn't seem to make any difference in subsequent reactions. The crude product was isolated as a foamy solid (174.1 g, containing mineral oil from the sodium hydride accounting for approximately 10% of each crude product, as well as varying amounts of EtOAc, estimated average yield >80% based on estimated individual batch purities). The material was carried forward without further purification.

B: (1R,2S)-2-(1H-indazol-6-yl)spiro-[cyclopropane-1,3'-indolin]-2'-one

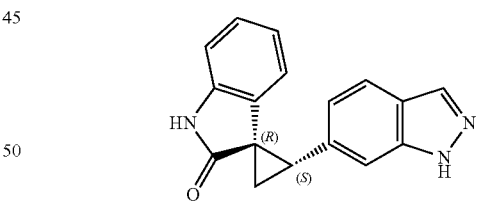

Method 1: A solution of (1R,2S)-2-(N1-benzyl-1H-indazol-6-yl)spiro-[N-benzyl-cyclopropane-1,3-indolin]-2'-one (6.5 g, up to 14 mmol; contains some solvent) in a mixture of DMSO (20 mL, 286 mmol) and THF (200 mL) was cooled in ice before addition of KO$^t$Bu (10.0 g, 89 mmol). The mixture darkened immediately. The mixture was purged gently with oxygen from balloons, warming slowly to rt. NMR of a sample after 5 h showed approx. 30% conversion, and so the mixture was let stir overnight under a balloon of oxygen (no purge). No further conversion had occurred, and so further KO$^t$Bu (20.0 g, 178 mmol) was added. Uptake of oxygen was immediately evident, suggesting that this large excess of base is required for effective deprotection. After a further 5 h, the mixture was poured into sat. aq. NH$_4$Cl (100 mL). Most of the THF was removed under reduced pressure, and the resulting mixture was extracted with portions of EtOAc (4×50 mL). The combined organic portions were washed with sat. aq. sodium thiosulfate (50 mL) and brine (50 mL), dried over $Na_2SO_4$, filtered and concentrated. The residue was slurried in $CH_2Cl_2$ (100 mL) and poured onto a short silica pad (2 cm depth×5 cm diameter) under suction. The major byproduct (Rf 0.6 in 1:1 EtOAc/cyclohexane, Rf 0.15 in $CH_2Cl_2$) was eluted using $CH_2Cl_2$ (ca. 1 L). The product (Rf 0.25 in 1:1 EtOAc/cyclohexane) was eluted using 2% then 5% MeOH/EtOAc. An impurity co-eluted with the product, as the latter 'streaked' badly. Concentrating the product containing fractions afforded the title compound (2.5 g, 64%) as a pale brown solid, contaminated with a second cyclopropane-containing compound (<10%; possibly a monobenzylated compound). HPLC indicated an optical purity of 94% e.e. (although the presence of a co-eluting impurity is suspected), with the major (1R,2S) enantiomer eluting at 14.3 min (Daicel Chiralpak AS-H (250×4.6 mm); isocratic 40% EtOH in n-heptane; 1 mL/min; 35° C.; Detection: 254, 230, 210 nm). From the racemic reference standard, the retention time of the (1S,2R) enantiomer was 9.9 min using this method. $^1$H NMR (400 MHz, $d_6$-DMSO) δ 13.01 (s, 1H), 10.61 (d, 1H J=8.3 Hz), 8.01 (s, 1H), 7.63 (d, J=8.3 Hz, 1H), 7.44 (s, 1H), 6.99 (t, J=7.5 Hz, 1H), 6.92 (d, J=8.0 Hz, 1H), 6.84 (d, J=8.0 Hz, 1H), 6.51 (t, J=7.0 Hz, 1H), 5.98 (d, 8.0 Hz, 1H), 3.20-3.17 (m, 1H), 2.30-2.26 (m, 1H), 2.00-1.95 (m, 1H); MS ESI 276.1 $[M+H]^+$, calcd for $[C_{17}H_{13}N_3O+H]^+$ 276.3.

Method 2: A number of batches of material were carried forward in this manner. A solution of (1R,2S)-2-(N1-benzyl-1H-indazol-6-yl)spiro-[N-benzyl-cyclopropane-1,3-indolin]-2'-one (10 g, up to 22 mmol; contains some solvent) in a mixture of DMSO (30 mL) and THF (300 mL) was cooled in ice before addition of KO$^t$Bu (37.0 g, 330 mmol). The mixture was purged gently with oxygen from balloons through a wide-gauge needle, and after an initiation period began to warm, reaching around 35-40° C. The purge was then stopped and the mixture left under an oxygen atmosphere (balloon). $^1$H NMR was used to monitor the course of each reaction, which was generally complete within 4-8 h. The mixture was poured into water (500 mL) and rendered acidic (pH 5-6) using dilute aq. HCl or citric acid. Most of the THF was removed under reduced pressure, and the product extracted using EtOAc (3-4 extracts, confirmed by TLC). The combined organic portions were washed with brine, dried over MgSO$_4$ and concentrated to afford the crude product. The crude products from a number of reactions were combined and purified using a dry-flash silica pad (4 cm depth×20 cm diameter). Byproducts were eluted using solvent of increasing eluent strength (0:1, 1:9, 1:4 EtOAc/cyclohexane), and then the product was eluted using EtOAc. Highly impure fractions were later re-purified in a similar fashion. The resulting material (31 g, containing traces of the Bn-derived reaction byproduct and an unidentified aromatic material) was used in the subsequent step without further purification.

Method 3: The title compound was also obtained from racemic (1R*,2S*)-2-(1H-indazol-6-yl)spiro-[cyclopropane-1,3-indolin]-2'-one (25 mg) by separation using chiral SFC: Chiralpak 1A (3×15 cm), isocratic 30% MeOH (0.1% DEA)/CO$_2$, 70 mL/min) to give a white solid (11.5 mg, 97% e.e., Rt=5.2 min, Chiralpak 1A (15×0.46 cm), 3.0 mL/min with isocratic 40% MeOH (0.1% DEA)/CO$_2$, 3.0 mL/min).

From this resolution process, the opposite enantiomer, (1S,2R)-2-(1H-indazol-6-yl)spiro-[cyclopropane-1,3-indolin]-2'-one was isolated as a white solid (11.8 mg, 98% e.e., Rt=2.7 min).

C: (1R,2S)-2-(3-iodo-1H-indazol-6-yl)spiro[cyclopropane-1,3'-indolin]-2'-one

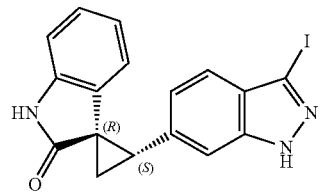

Method 1: A mixture of (1R,2S)-2-(1H-indazol-6-yl) spiro-[cyclopropane-1,3-indolin]-2'-one (2.20 g, 8.0 mmol, ca. 94% e.e.) and K$_2$CO$_3$ (2.21 g, 16.0 mmol) in dry DMF (20 mL) was treated with a solution of 12 (3.45 g, 13.6 mmol) in dry DMF (15 mL), adding the latter by syringe pump over 45 min. The mixture was stirred for 1.5 h and then poured into a mixture of water (400 mL) and sat. aq. Na$_2$S$_2$O$_3$. The resulting mixture was triturated in an ultrasound bath for 30 min to break up the sticky clumps of solid, then filtered. The solids were washed with water (2×50 mL), partially dried under suction, then stripped twice with acetone to remove residual water. HPLC of the crude mixture indicated an optical purity of 95% e.e. with the major (1R,2S) enantiomer eluting at 14.1 min (Daicel Chiralpak AS-H (250×4.6 mm); isocratic 40% EtOH in n-heptane; 1 mL/min; 35° C.; Detection: 254, 230, 210 nm). From the racemic reference standard, the retention time of the (1S,2R) enantiomer was 8.4 min using this method, and both enantiomers of the minor diasteremer product were also detected at 6.0 min and 6.9 min. Baseline material was removed by passing an EtOAc solution of the product through a short silica pad (2 cm depth×4 cm diameter), eluting with further EtOAc. Further purification was then attempted by trituration. Et$_2$O and toluene removed some of the impurities, but no enhancement of optical purity was observed. Recrystallization from THF/cyclohexane and EtOAc/cyclohexane were also unsuccessful, and so the material was purified by column chromatography on silica (20 cm depth×4 cm diameter) using 1:1 EtOAc/cyclohexane to afford the title compound (1.47 g, 46%) as an off-white powder. $^1$H NMR (400 MHz, d$_6$-DMSO) δ 13.47 (s, 1H), 10.62 (s, 1H), 7.47 (s, 1H), 7.30 (d, J=8.0 Hz, 1H), 7.02-6.98 (m, 2H), 6.84 (d, J=7.6 Hz, 1H), 6.53 (t, J=7.6 Hz, 1H), 5.97 (d, J=7.6 Hz, 1H), 3.18 (q, J=8.4 Hz, 1H), 2.31 (dd, J=7.2, 4.8 Hz, 1H), 1.98 (dd, J=8.8, 4.8 Hz, 1H); MS ESI 402.0 [M+H]$^+$, calcd for [C$_{17}$H$_{12}$IN$_3$O+H]$^+$ 402.0.

Method 2: Part-purified (1R,2S)-2-(1H-indazol-6-yl) spiro-[cyclopropane-1,3-indolin]-2'-one (10.6 g, up to 38 mmol) was dissolved in a mixture of 2.0 M aq. NaOH (150 mL, 300 mmol) and dioxane (150 mL). Iodine (13.4 g, 53.3 mmol) was added in several portions. No significant exotherm was observed during or following addition. The iodine rapidly dispersed. TLC was used to monitor conversion; in some batches a little extra (~0.2 eq) iodine had to be added to push the reaction to completion. After 30 min, excess reagent was quenched using sat. aq. Na$_2$S$_2$O$_3$ and most of the solvent was removed under reduced pressure. The residues were taken up in EtOAc and half-sat. brine. The layers were separated and the aqueous phase extracted with further EtOAc (2-3 further portions; confirmed by TLC). The combined organic portions were washed with brine, dried over MgSO₄ and concentrated to afford the crude product, which was combined with further batches for purification. Four reactions were carried out using part-purified material (likely to contain some inorganics, starting material weights 2.8 g, 10.6 g, 9.3 g and 8.3 g, Total 31 g, theoretically up to 111 mmol but actually less than this) gave a combined crude yield of 43 g crude product, which was triturated with EtOAc (100 mL) over a weekend. The off-white solid was collected by filtration, washed with further EtOAc (2×10 mL) then dried under suction and finally under high vacuum to afford the title compound (20.7 g; ≥98.5% e.e. by HPLC). Following a silica plug and trituration on mother liquor, a further 5 g (12.5 mmol, 11%) of the final product was isolated, again in good e.e. Overall average yield over three steps from pure dimesylate 20.6%. Optical Rotation: $[\alpha]^{21}_D = -214°$ (c 0.43, MeOH).

Method 3: The title compound was also obtained from racemic (1R*,2S*)-2-(3-iodo-1H-indazol-6-yl)spiro[cyclopropane-1,3'-indolin]-2'-one (35 mg) by separation using chiral HPLC (Lux Cellulose AXIA (150×21.2 mm), gradient of 10% isopropanol/Hexane to 90% isopropanol/hexane at 20 mL/min) to give a white solid (8.8 mg, 98% e.e., Rt=7.8 min, Lux Cellulose AXIA (150×4.6 mm), 1.0 mL/min with Gradient 10% isopropanol/Hexane to 90% isopropanol/hexane). From this resolution process, the opposite enantiomer, (1S,2R)-2-(3-iodo-1H-indazol-6-yl)spiro[cyclopropane-1,3'-indolin]-2'-one was isolated as a white solid (7.7 mg, 98% e.e., Rt=6.7 min).

Method 4: The title compound was also obtained from racemic (1R*,2S*)-2-(3-iodo-1H-indazol-6-yl)spiro[cyclopropane-1,3'-indolin]-2'-one (1 g) by separation using chiral SFC (Chiralcel OJ-H (2×25 cm), isocratic 40% methanol (0.1% DEA)/CO2, 100 bar at 50 mL/min) to give a white solid (478 mg, >99% e.e., Rt=1.7 min, Chiralcel OJ-H (10×0.46 cm), isocratic 40% methanol (0.1% DEA)/CO2, 100 bar at 3.0 mL/min). From this resolution process, the opposite enantiomer, (1S,2R)-2-(3-iodo-1H-indazol-6-yl)spiro[cyclopropane-1,3'-indolin]-2'-one was isolated as a white solid (426 mg, >99% e.e., Rt=2.5 min).

Example 2

(1R,2S)-5'-fluoro-2-(3-iodo-1H-indazol-6-yl)spiro[cyclopropane-1,3'-indolin]-2'-one

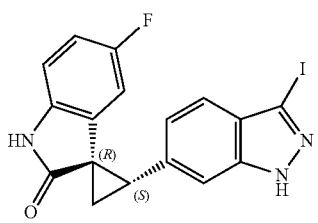

A. (1R,2S)-1'-benzyl-2-(1-benzyl-1H-indazol-6-yl)-5'-fluorospiro [cyclopropane-1,3'-indolin]-2'-one

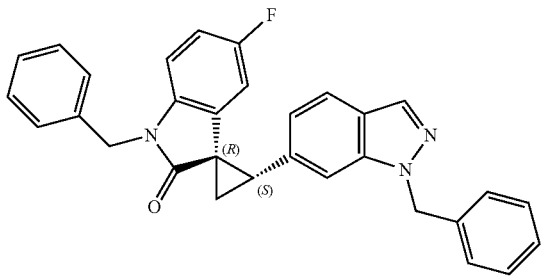

The title compound was prepared in a manner similar to the method of (1R,2S)-1'-benzyl-2-(1-benzyl-1H-indazol-6-yl)spiro[cyclopropane-1,3'-indolin]-2'-one using (S)-1-(1-benzyl-1H-indazol-6-yl)ethane-1,2-diyl dimethanesulfonate (501.4 mg, 1.181 mmol) and 1-benzyl-5-fluoroindolin-2-one (285.0 mg, 1.181 mmol). Purification using Biotage Isolera (SNAP 25 g column, 25-100% EtOAc in hexane) yielded the title compound as a cream solid (352 mg, 63%; 97% e.e.) with the major (1R,2S) enantiomer eluting at 7.03 min (Phenomenex Lux 5µ Cellulose-1 (150×4.6 mm), 1.0 mL/min isocratic at 80% EtOH in hexane for 1.0 min, then gradient 80-90% EtOH in hexane over 10 min). From the racemic reference standard, the retention time of the (1S,2R) enantiomer was 5.95 min using this method. $^1$H NMR (400 MHz, CDCl₃) δ 8.04 (s, 1H), 7.67 (d, J=8.8 Hz, 1H), 7.40-7.27 (m, 8H), 7.17 (s, 1H), 7.11 (d, J=7.2 Hz, 2H), 6.92 (d, J=8.4 Hz, 1H), 6.67-6.62 (m, 2H), 5.62 (d, J=15.6 Hz, 1H), 5.55 (d, J=15.6 Hz, 1H), 5.51 (t, J=6.0 Hz, 1H), 5.10 (d, J=15.6 Hz, 1H), 4.94 (d, J=16.0 Hz, 1H), 3.53 (t, J=8.4 Hz, 1H), 2.32 (dd, J=9.2, 4.4 Hz, 1H), 2.02 (dd, J=8.0, 3.2 Hz, 1H), MS ESI 474.3 [M+H]⁺, calcd for [C₃₁H₂₄FN₃O+H]⁺ 474.2.

B. (1R,2S)-5'-fluoro-2-(1H-indazol-6-yl)spiro[cyclopropane-1,3'-indolin]-2'-one

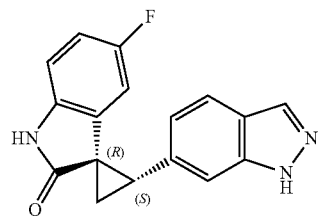

The title compound was prepared in a manner similar to the method of (1R,2S)-2-(1H-indazol-6-yl)spiro[cyclopropane-1,3'-indolin]-2'-one using (1R,2S)-1'-benzyl-2-(1-benzyl-1H-indazol-6-yl)-5'-fluorospiro[cyclopropane-1,3'-indolin]-2'-one (560 mg, 1.18 mmol). Purification by using silica gel column chromatography with 5-95% EtOAc in hexane to give the title compound as a creamy solid (179 mg, 52%). $^1$H NMR (400 MHz, CD₃OD) δ 8.03 (s, 1H), 7.71 (d, J=8.0 Hz, 1H), 7.62-7.46 (m, 2H), 6.94 (d, J=8.4 Hz, 1H), 6.88 (t, J=4.8 Hz, 1H), 5.69 (d, J=9.2 Hz, 1H), 3.39 (t, J=8.0 Hz, 1H), 2.30-2.71 (m, 1H), 2.23-2.18 (m, 1H); MS ESI 294.1 [M+H]⁺, calcd for [C₁₇H₁₂FN₃O+H]⁺ 294.10.

C. (1R,2S)-5'-fluoro-2-(3-iodo-1H-indazol-6-yl)spiro[cyclopropane-1,3'-indolin]-2'-one

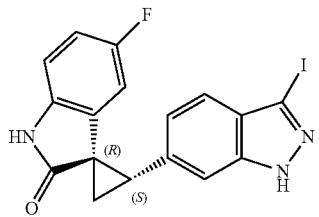

The title compound was prepared in a manner similar to the method of (1R,2S)-2-(3-iodo-1H-indazol-6-yl)spiro[cyclopropane-1,3'-indolin]-2'-one using (1R,2S)-5'-fluoro-2-(1H-indazol-6-yl)spiro[cyclopropane-1,3'-indolin]-2'-one (240 mg, 0.818 mmol). Purification using Biotage Isolera with SNAP 25 g column with 5-90% EtOAc in hexane yielded the title compound as a cream solid (195 mg, 57%; 97% e.e.) with the major (1R,2S) enantiomer eluting at 3.7 min (Phenomenex Lux 5 g Cellulose-2 (150×4.6 mm); isocratic 25% EtOH in n-hexane; 1.5 mL/min; 24° C.; Detection: 254 nm). From the racemic reference standard, the retention time of the (1S,2R) enantiomer was 3.2 min using this method. $^1$H NMR (400 MHz, CD$_3$OD) δ 7.47 (s, 1H), 7.38 (d, J=8.4 Hz, 1H), 7.01 (d, J=8.8 Hz, 1H), 6.88 (dd, J=8.8, 4.4 Hz, 1H), 6.79 (t, J=8.8 Hz, 1H), 5.69 (d, J=8.4 Hz, 1H), 3.38 (t, J=8.8 Hz, 1H), 2.28 (dd, J=8.8, 4.2 Hz, 1H), 2.21 (dd, J=9.2, 4.4 Hz, 1H); MS ESI 420.0 [M+H]$^+$, calcd for [C$_{17}$H$_{11}$FIN$_3$O+H]$^+$ 420.0.

Example 3

(1R,2S)-2-(3-iodo-1H-indazol-6-yl)-5'-methylspiro[cyclopropane-1,3'-indolin]-2'-one

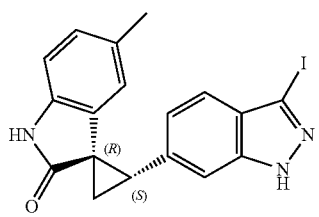

A. (1R,2S)-1'-benzyl-2-(1-benzyl-1H-indazol-6-yl)-5'-methylspiro[cyclopropane-1,3'-indolin]-2'-one

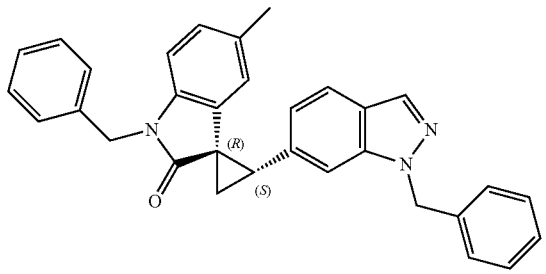

To a 250 mL round bottom flask charged with 60% NaH (1.20 g, 30 mmol) was added anhydr. THF (20 mL) and the resulting mixture was cooled to 0° C. A solution of 1-benzyl-5-methylindolin-2-one (2.37 g, 10 mmol) in dry THF (25 mL) was added over 2 min, followed by rinsing with THF (5 mL). After stirring for 20 min at 0° C., a solution of (S)-1-(1-benzyl-1H-indazol-6-yl)ethane-1,2-diyl dimethanesulfonate (4.24 g, 10 mmol) in dry THF (45 mL) was added dropwise through dropping funnel over 40 min, followed by rinsing with THF (5 mL). After addition, the resulting mixture was stirred for 30 min at 0° C. (TLC showed completion) then left O/N at rt. After cooling to 0° C., the reaction mixture was poured into an Erlenmeyer flask containing ice (100 mL) and sat. NH$_4$Cl (30 mL) and extracted with EtOAc (150 mL×2), dried (Na$_2$SO$_4$). After removal of solvents, the residue was transferred to a 100 mL RBF using 30 mL of EtOAc and crystals formed. Suction filtration gave the title compound as a beige solid (1.537 g). The filtrate was concentrated and purified by Biotage Isolera (20-30% EtOAc in hexane) and triturated with EtOAc/hexane to give 2nd crop as off white solid (1.560 g). The filtrate was purified using the above procedure to give 3rd crop as a beige solid (115 mg). Total 3.212 g (68%). $^1$H NMR (400 MHz, CDCl$_3$) δ 8.02 (s, 1H), 7.63 (d, J=8.0 Hz, 1H), 7.36-7.20 (m, 9H), 7.14 (d, J=6.0 Hz, 2H), 6.94 (d, J=8.4 Hz, 1H), 6.80 (d, J=8.0 Hz, 1H), 6.64 (d, J=7.2 Hz, 1H), 5.62 (d, J=16.8 Hz, 1H, partially overlapping with s at 5.59), 5.59 (s, 1H, partially overlapping with d at 5.62), 5.55 (d, J=16.8 Hz, 1H), 5.08 (d, J=16.0 Hz, 1H), 4.97 (d, J=15.6 Hz, 1H), 3.48 (t, J=8.4 Hz, 1H), 2.30-2.25 (m, 1H), 2.02-1.96 (m, 1H), 1.85 (s, 3H); MS ESI 470.3 [M+H]$^+$, calcd for [C$_{32}$H$_{27}$N$_3$O+H]$^+$ 470.2

B. (1R,2S)-2-(1H-indazol-6-yl)-5'-methylspiro[cyclopropane-1,3'-indolin]-2'-one

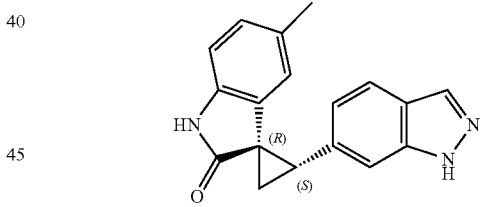

To a 100 mL flask charged with (1R,2S)-1'-benzyl-2-(1-benzyl-1H-indazol-6-yl)-5'-methylspiro[cyclopropane-1,3'-indolin]-2'-one (469 mg, 1 mmol) was added dry THF (2 mL) and the resulting mixture was stirred at 0° C. before KO$^t$Bu (1 M in THF, 18 mL, 18 mmol) was added over 2 min. After addition, the resulting mixture was stirred for 15 min at 0° C. and DMSO (1.85 mL) was added. Oxygen was bubbled through for 1 h and reaction turned from homogeneous to heterogeneous. LC-MS showed good conversion at 50 min. It was quenched with sat. NH$_4$Cl.

The above reaction was repeated on a larger scale using (1R,2S)-1'-benzyl-2-(1-benzyl-1H-indazol-6-yl)-5'-methylspiro[cyclopropane-1,3'-indolin]-2'-one (1.41 g, 3 mmol). After quenching with saturated NH$_4$Cl, two reactions were combined, diluted with H$_2$O and extracted with EtOAc (100 mL×2). Purification by Biotage Isolera (10-95% EtOAc in hexane) gave the title compound as a light solid (680 mg, 53%). $^1$H NMR (400 MHz, CD$_3$OD) δ 8.02 (s, 1H), 7.67 (d, J=8.4 Hz, 1H), 7.46 (s, 1H), 6.94 (d, J=8.4 Hz, 1H), 6.85 (d, J=8.0 Hz, 1H), 6.81 (d, J=7.6 Hz, 1H), 5.78 (s, 1H), 3.32 (t, overlapping with MeOH residue), 2.20-2.12 (m, 2H), 1.87 (s, 3H); MS ESI 290.1 [M+H]$^+$, calcd for [C$_{18}$H$_{15}$N$_3$O+H]$^+$ 290.1.

C. (1R,2S)-2-(3-iodo-1H-indazol-6-yl)-5'-methyl-spiro[cyclopropane-1,3'-indolin]-2'-one

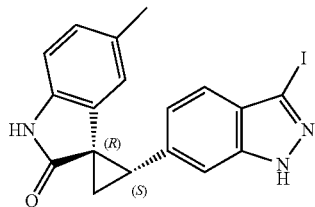

Method 1: To a solution of (1R,2S)-2-(1H-indazol-6-yl)-5'-methylspiro[cyclopropane-1,3'-indolin]-2'-one (680 mg, 2.35 mmol) in DMF (16 mL) was added K$_2$CO$_3$ (544 mg, 4 mmol), followed by iodine (851 mg, 3.2 mmol). The resulting mixture was stirred for 3 h at rt, cooled to 0° C., quenched with sat. Na$_2$S$_2$O$_3$, diluted with H$_2$O, extracted with EtOAc (50 mL×3) and dried (Na$_2$SO$_4$). Evaporation of solvents and purification by Biotage Isolera (EtOAc/hexane gradient: 10-90%) gave the title compound as a light yellow solid (794 mg, 81%; >98% e.e.). The major (1R,2S)-enantiomer eluted at 9.6 min (Phenomenex Lux 5u Cellulose-2 (150×4.6 mm); isocratic 10% EtOH in n-hexane 1.75 L/min; ambient temperature; Detection: 254, 214 nm). From the racemic reference standard, the retention time of the (1S,2R)-enantiomer was 7.7 min using this method. $^1$H NMR (400 MHz, DMSO-d6) δ 13.46 (s, 1H), 10.51 (s, 1H), 7.47 (s, 1H), 7.32 (d, J=8.8 Hz, 1H), 7.02 (d, J=8.0 Hz, 1H), 6.81 (d, J=7.6 Hz, 1H), 6.73 (d, J=7.6 Hz, 1H), 5.86 (s, 1H), 3.16 (t, overlapping with trace MeOH residue), 2.32-2.25 (m, 1H), 2.00-1.93 (m, 1H), 1.85 (s, 3H); MS ESI 416.0 [M+H]$^+$, calcd for [C$_{18}$H$_{14}$IN$_3$O+H]$^+$ 416.0. Optical Rotation: [α]$^{23}_D$=−145° (c 0.488, MeOH).

Method 2: The title compound was also obtained from racemic (1R*,2S*)-2-(3-iodo-1H-indazol-6-yl)-5'-methylspiro[cyclopropane-1,3'-indolin]-2'-one (1 g) by separation using chiral SFC (Chiralcel OJ-H (3×15 cm), isocratic 40% ethanol (0.1% DEA)/CO$_2$, 100 bar at 75 mL/min) to give a white solid (392 mg, >99% e.e., Rt=2.10 min, Chiralcel OJ-H (10×0.46 cm), isocratic 40% ethanol (0.1% DEA)/CO$_2$, 100 bar at 3.0 mL/min). Optical Rotation: [α]$^{22}_D$=−146° (c 0.52, MeOH). From this resolution process, the opposite enantiomer, (1S,2R)-2-(3-iodo-1H-indazol-6-yl)-5'-methylspiro[cyclopropane-1,3'-indolin]-2'-one was isolated as a white solid (387 mg, >99% e.e., Rt=1.59 min).

Example 4

(1R,2S)-2-(3-iodo-1H-indazol-6-yl)-5'-methoxyspiro[cyclopropane-1,3'-indolin]-2'-one

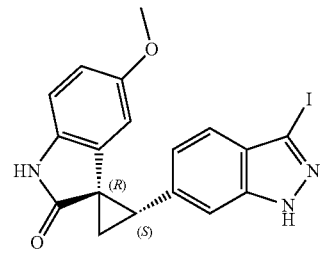

A. (1R,2S)-1'-benzyl-2-(1-benzyl-1H-indazol-6-yl)-5'-methoxyspiro[cyclopropanane-1,3'-indolin]-2'-one

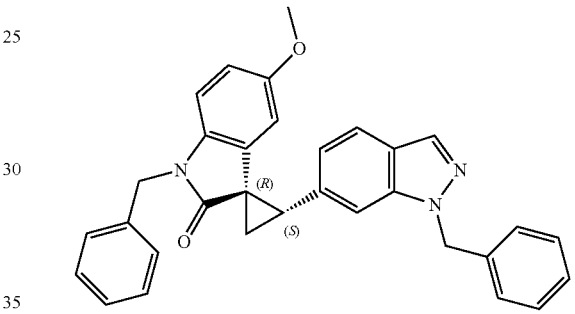

Method 1: The title compound was prepared in a manner similar to the method of (1R,2S)-1'-benzyl-2-(1-benzyl-1H-indazol-6-yl)spiro[cyclopropane-1,3'-indolin]-2'-one using (S)-1-(1-benzyl-1H-indazol-6-yl)ethane-1,2-diyl dimethanesulfonate (3.35 g, 7.90 mmol) and 1-benzyl-5-methoxy-indolin-2-one (2.00 g, 7.90 mmol). The crude product was purified by silica gel chromatography (15-40% EtOAc in hexane) followed by trituration (EtOAc) to give the title compound as a white solid (1.97 g, 52%). $^1$H NMR (400 MHz, CDCl$_3$) δ 8.01 (s, 1H), 7.64 (d, J=8.2 Hz, 1H), 7.36-7.23 (m, 10H), 7.14 (d, J=7.2 Hz, 2H), 6.94 (d, J=8.3 Hz, 1H), 6.63 (d, J=8.3 Hz, 1H), 6.53 (d, J=8.4 Hz, 1H), 5.61 (d, J=15.1 Hz, 1H), 5.54 (d, J=15.4 Hz, 1H), 5.37 (s, 1H), 5.07 (d, J=15.4 Hz, 1H), 4.95 (d, J=15.7 Hz, 1H), 3.51 (t, J=8.1 Hz, 1H), 3.18 (s, 3H), 2.32-2.29 (m, 1H), 2.09-2.00 (m, 1H). MS ESI 486.3 [M+H]$^+$, calcd for [C$_{32}$H$_{27}$N$_3$O$_2$+H]$^+$ 486.2.

Method 2: In a similar manner to Example 4A Method 1, the title compound was prepared in 2 batches using (S)-1-(1-benzyl-1H-indazol-6-yl)ethane-1,2-diyl dimethanesulfonate (total 13.41 g, 31.6 mmol) and 1-benzyl-5-methoxy-indolin-2-one (total 8 g, 31.6 mmol). Following extraction with EtOAc and evaporation, water (75 mL) was added to the residue and the resulting mixture was stirred for 30 min at RT. Filtration and washing with water (7.5 mL×2) gave a solid which was suspended in methanol (75 mL) with stirring at 65° C. for 30 min, then at RT for 30 min. Filtration and washing with methanol (5 mL×3) gave the title compound as a light brown solid (9 g, 59%). $^1$H NMR and mass spectral data were identical to material obtained from Method 1.

Method 3: In a similar manner to Example 4A) Method 1, the title compound was prepared in 2 batches using (S)-1-(1-benzyl-1H-indazol-6-yl)ethane-1,2-diyl dimethanesulfonate (total 22.37 g, 52.7 mmol) and 1-benzyl-5-methoxy-indolin-2-one (13.35 g, 52.7 mmol). Following extraction with EtOAc and evaporation, water (125 mL) was added to the residue and the resulting mixture was stirred for 30 min at RT. Filtration and washing with water (15 mL×3) gave a solid which was suspended in toluene (96 mL) and hexane (96 mL) with stirring at 80° C. for 30 min, then at RT for 30 min. Filtration and washing with hexane (15 mL×3) gave the title compound as a light brown solid (19.94 g, 78%). $^1$H NMR and mass spectral data were identical to material obtained from Method 1.

B. (1R,2S)-2-(1H-indazol-6-yl)-5'-methoxyspiro[cyclopropane-1,3'-indolin]-2'-one

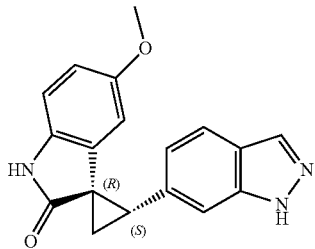

Method 1: The title compound was prepared in a manner similar to the method of (1R,2S)-2-(1H-indazol-6-yl)-5'-methylspiro[cyclopropane-1,3'-indolin]-2'-one using (1R,2S)-1'-benzyl-2-(1-benzyl-1H-indazol-6-yl)-5'-methoxyspiro[cyclopropane-1,3'-indolin]-2'-one (1.0 g, 2.1 mmol). Purification via column chromatography (silica gel, 30-80% EtOAc in hexane) yielded the title compound as a white solid (0.50 g, 80%). $^1$H NMR (400 MHz, DMSO-d$_6$) δ 13.02 (br s, 1H), 10.42 (br s, 1H), 8.02 (s, 1H), 7.64 (d, J=8.3 Hz, 1H), 7.45 (s, 1H), 6.94 (d, J=7.8 Hz, 1H), 6.73 (d, J=8.2 Hz, 1H), 6.55 (d, J=8.6 Hz, 1H), 5.62 (s, 1H), 3.20 (s, 3H), 3.18 (t, J=8.7 Hz, 1H), 2.34-2.28 (m, 1H), 1.98-1.95 (m, 1H). MS ESI 306.1 [M+H]$^+$, calcd for [C$_{18}$H$_{15}$N$_3$O$_2$+H]$^+$306.12. Optical Rotation: [α]$^{23}_D$=−225° (c 0.441, MeOH).

Method 2: In a similar manner to Example 4B) Method 1, the title compound was prepared in 3 batches using (1R,2S)-1'-benzyl-2-(1-benzyl-1H-indazol-6-yl)-5'-methoxyspiro[cyclopropane-1,3'-indolin]-2'-one (total 28.9 g, 59.5 mmol). The O$_2$ purge was carried out for 3-4 h at 0° C. to RT. After a further 15 min, the mixture was quenched with 20% aq. NH$_4$Cl, extracted with EtOAc, dried and evaporated. For one batch, acetonitrile (25 mL) was added, and the solid suspension was stirred at RT for 30 min, filtered and dried under vacuum to give the title compound as a creamy solid (3.14 g, 1st crop). The residue obtained by evaporation of the filtrate was purified using Biotage Isolera (10-90% EtOAc in hexane, SNAP 50 g column) to give the 2nd crop (1.1 g). Combined batch yield (4.24 g, 59%). The other batches were processed in the same way to give a total yield (10.4 g, 53-59%).

C. (1R,2S)-2-(3-iodo-1H-indazol-6-yl)-5'-methoxyspiro[cyclopropanane-1,3'-indolin]-2'-one

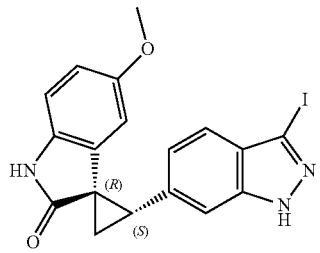

Method 1: The title compound was prepared in a manner similar to the method 2 for (1R,2S)-2-(3-iodo-1H-indazol-6-yl)spiro[cyclopropane-1,3'-indolin]-2'-one using (1R,2S)-2-(1H-indazol-6-yl)-5'-methoxyspiro[cyclopropane-1,3'-indolin]-2'-one (0.40 g, 1.3 mmol). Crude product was triturated with EtOAc (5 mL) to yield the title compound as a white solid (0.52 g, 93%, >98% e.e.) with the major (1R,2S) enantiomer eluting at 8.5 min (Phenomenex Lux 5µ Cellulose-2 (150×4.6 mm); 1.0 mL/min; isocratic at 10% $^i$PrOH in n-hexane for 1.0 min, then gradient 10-90% $^i$PrOH in n-hexane over 10 min, then isocratic at 90% $^i$PrOH in n-hexane for 2.0 min; 1.0 mL/min; 24° C.; Detection: 254 nm). From the racemic reference standard, the retention time of the (1S,2R) enantiomer was 6.2 min using this method. $^1$H NMR (400 MHz, DMSO-d6) δ 13.48 (br s, 1H), 10.43 (br s, 1H), 7.49 (s, 1H), 7.31 (d, J=8.6 Hz, 1H), 7.02 (d, J=8.1 Hz, 1H), 6.73 (d, J=8.4 Hz, 1H), 6.57 (d, J=8.6 Hz, 1H), 5.62 (s, 1H), 3.29 (s, 3H), 3.19 (t, J=8.4 Hz, 1H), 2.36-2.32 (m, 1H), 1.99-1.96 (m 1H). MS ESI 432.1 [M+H]$^+$, calcd for [C$_{18}$H$_{14}$IN$_3$O$_2$+H]$^+$432.0. Optical Rotation: [α]$^{22}_D$=−143° (c 0.399, MeOH).

Method 2: The title compound was prepared by adding anhydrous K$_2$CO$_3$ (9.41 g, 68 mol) to a solution of (1R,2S)-2-(1H-indazol-6-yl)-5'-methoxyspiro[cyclopropane-1,3'-indolin]-2'-one (10.4 g, 34 mmol) in DMF (60 mL), followed by iodine (12.97 g, 0.051 mol). The resulting mixture was stirred for 18 h at RT and then poured with stirring into Na$_2$S$_2$O$_3$.5H$_2$O (aqueous, 1%, 1.0 L). Filtration and washing with water (50 mL×2) gave a solid which was suspended in IPA:hexane (60 mL, 1:1) with stirring at 65° C. for 30 min, then at RT for 30 min. The solid was filtered and washed with hexane (10 mL×2) to give the title compound as a light brown solid (13 g, 88%, 96.8% e.e. by HPLC). Optical Rotation: [α]$^{22}_D$=−132° (c 0.43, MeOH).

Method 3: The title compound was also obtained from racemic (1R*,2S*)-2-(3-iodo-1H-indazol-6-yl)-5'-methoxyspiro spiro[cyclopropane-1,3'-indolin]-2'-one (15 g) by separation using chiral SFC: Chiralcel OJ-H (3×15 cm), (30% methanol (0.1% DEA)/CO$_2$, 75 mL/min) to give a white solid (6.75 g, 99% e.e., Rt=2.1 min, Chiralpak 1A (150×4.6 mm), 3.0 mL/min isocratic 40% isopropanol (0.1% DEA)/CO$_2$). From this resolution process, the opposite enantiomer, (1S,2R)-2-(3-iodo-1H-indazol-6-yl)-5'-methoxyspiro[cyclopropane-1,3'-indolin]-2'-one was isolated as a white solid (6.6 g, 99% e.e., Rt=3.4 min).

Example 5

(1R,2S)-2-(3-iodo-1H-indazol-6-yl)-1'-methylspiro[cyclopropane-1,3'-indolin]-2'-one

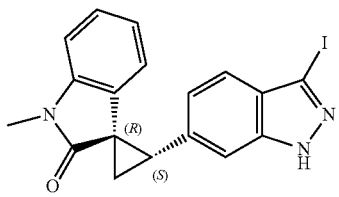

A. (1R,2S)-2-(1-benzyl-1H-indazol-6-yl)-1'-methylspiro[cyclopropane-1,3'-indolin]-2'-one

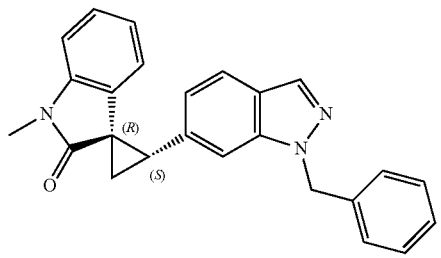

The title compound was prepared in a manner similar to the method of (1R,2S)-1'-benzyl-2-(1-benzyl-1H-indazol-6-yl)spiro[cyclopropane-1,3'-indolin]-2'-one using (S)-1-(1-benzyl-1H-indazol-6-yl)ethane-1,2-diyl dimethanesulfonate (6.70 g, 15.8 mmol) and 1-methylindolin-2-one (2.33 g, 15.8 mmol). Purification via column chromatography (silica gel, 25-50% EtOAc in hexane) yielded the title compound as a pale-orange crystalline solid (5.01 g, 84%); $^1$H NMR (400 MHz, CDCl$_3$) δ 8.00 (s, 1H), 7.60 (d, J=8.3 Hz, 1H), 7.30-7.25 (m, 3H), 7.18 (s, 1H), 7.13-7.10 (m, 3H), 6.92 (d, J=8.6 Hz, 1H), 6.85 (d, J=7.6 Hz, 1H), 6.55 (t, J=7.0 Hz, 1H), 5.76 (d, J=7.2 Hz, 1H), 5.63-5.49 (m, 2H), 3.41 (t, J=8.8 Hz, 1H), 3.33 (s, 3H), 2.22-2.18 (m, 1H), 2.00-1.96 (m, 1H); MS ESI 380.2 [M+H]$^+$, calcd for [C$_{25}$H$_{21}$N$_3$O+H]$^+$ 380.18.

B. (1R,2S)-2-(1-(4-methoxybenzyl)-1H-indazol-6-yl)-1'-methylspiro[cyclopropane-1,3'-indolin]-2'-one

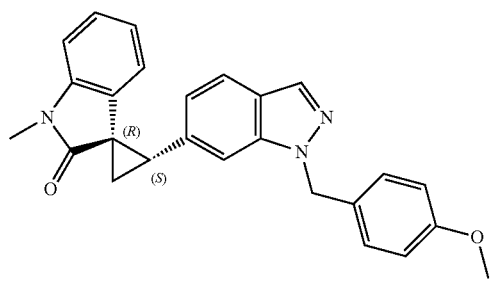

The title compound was prepared in a manner similar to the method of (1R,2S)-1'-benzyl-2-(1-benzyl-1H-indazol-6-yl)spiro[cyclopropane-1,3'-indolin]-2'-one using (S)-1-(1-(4-methoxybenzyl)-1H-indazol-6-yl)ethane-1,2-diyl dimethanesulfonate (2.03 g, 4.47 mmol) and 1-methylindolin-2-one (658 mg, 4.47 mmol). Purification using Biotage Isolera (silica gel, 20-50% EtOAc in hexane) yielded the title compound as a yellowish crystalline solid (1.47 g, 80%); $^1$H NMR (400 MHz, CD$_3$OD) δ 7.98 (s, 1H), 7.61 (d, J=8.4 Hz, 1H), 7.43 (s, 1H), 7.13-7.06 (m, 3H), 6.97 (d, J=7.8 Hz, 1H), 6.92 (d, J=8.4 Hz, 1H), 6.80 (d, J=8.3 Hz, 2H), 6.50 (t, J=7.6 Hz, 1H), 5.78 (d, J=7.6 Hz, 1H), 5.58-5.47 (m, 2H), 3.72 (s, 3H), 3.36-3.30 (m, 4H), 2.22-2.19 (m, 1H), 2.16-2.12 (m, 1H); MS ESI 410.2 [M+H]$^+$, calcd for [C$_{26}$H$_{23}$N$_3$O$_2$+H]$^+$ 410.19.

C. (1R,2S)-2-(1H-indazol-6-yl)-1'-methylspiro[cyclopropane-1,3'-indolin]-2'-one

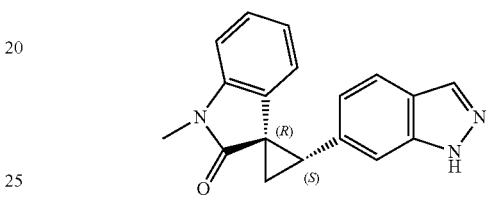

Method 1 (Bn): The title compound was prepared in a manner similar to the method of (1R,2S)-2-(1H-indazol-6-yl)spiro[cyclopropane-1,3'-indolin]-2'-one using (1R,2S)-2-(1-benzyl-1H-indazol-6-yl)-1'-methylspiro[cyclopropane-1,3'-indolin]-2'-one (1.16 g, 3.06 mmol). Purification via column chromatography (silica gel, 3-6% MeOH in CH$_2$Cl$_2$) yielded the title compound as a pale-yellow solid (656 mg, 74%); $^1$H NMR (400 MHz, CDCl$_3$) δ 10.06 (br. s, 1H), 8.05 (s, 1H), 7.64 (d, 1H, J=7.6 Hz), 7.36 (s, 1H), 7.14 (t, J=8.7 Hz, 1H), 6.97 (d, J=8.7 Hz, 1H), 6.87 (d, J=8.2 Hz, 1H), 6.62 (t, J=7.6 Hz, 1H), 5.91 (d, J=7.9 Hz, 1H), 3.46 (t, J=7.8 Hz, 1H), 3.34 (s, 3H), 2.26-2.23 (m, 1H), 2.08-2.04 (m, 1H); MS ESI 290.1 [M+H]$^+$, calcd for [C$_{18}$H$_{15}$N$_3$O+H]$^+$ 290.13.

Method 2 (PMB): (1R,2S)-2-(1-(4-methoxybenzyl)-1H-indazol-6-yl)-1'-methylspiro[cyclopropane-1,3'-indolin]-2'-one (1.47 g, 3.59 mmol) was dissolved into TFA (7.0 mL) and then TfOH (0.70 mL) was added. The reaction was heated to reflux for 18 h and then cooled to 0° C. before neutralization with 1.0M NaOH. Extracted with CH$_2$Cl$_2$ (3×), washed organic layer with brine and dried over MgSO$_4$. The solvent was removed and the resulting residue dried under high vacuum. The crude sample was carried forward without further purification. $^1$H NMR and mass spectral data were identical to material obtained from Method 1 (Bn) above.

D. (1R,2S)-2-(3-iodo-1H-indazol-6-yl)-1'-methylspiro[cyclopropane-1,3'-indolin]-2'-one

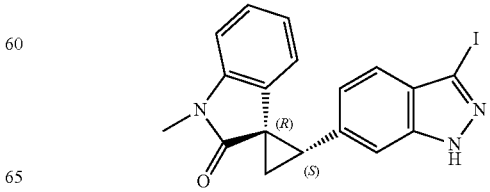

Method 1 (Bn): The title compound was prepared in a manner similar to the method of (1R,2S)-2-(3-iodo-1H-indazol-6-yl)spiro[cyclopropane-1,3'-indolin]-2'-one using (1R,2S)-2-(1H-indazol-6-yl)-1'-methylspiro[cyclopropane-1,3'-indolin]-2'-one from method 1 (Bn) (930 mg, 3.21 mmol). Precipitation with EtOAc followed by filtration and rinsing with EtOAc gave the title compound (970 mg, 73%; >98% e.e.) with the major enantiomer eluting at 2.4 min (Phenomenex Lux 5μ Amylose-2 150×4.6 mm, 2.5 mL/min with isocratic at 20% EtOH in hexane for 0.5 min, then gradient 20-50% EtOH in hexane over 2.5 min, then isocratic at 50% for 1 min). From the racemic reference standard, the retention time of the (1S,2R) enantiomer was 3.0 min using this method. $^1$H NMR (400 MHz, CDCl$_3$) δ 10.96 (br. s, 1H), 7.43-7.39 (m, 2H), 7.16 (t, J=7.6 Hz, 1H), 7.05 (d, J=8.0 Hz, 1H), 6.89 (d, J=7.8 Hz, 1H), 6.66 (t, J=7.2 Hz, 1H), 5.91 (d, J=8.0 Hz, 1H), 3.47 (t, J=8.4 Hz, 1H), 3.35 (s, 3H), 2.30-2.26 (m, 1H), 2.08-2.04 (m, 1H); MS ESI 416.0 [M+H]$^+$, calcd for [C$_{18}$H$_{14}$IN$_3$O+H]$^+$416.03. Optical Rotation: [α]$^{23}_D$=−210° (c 0.4, MeOH).

Method 2: Crude (1R,2S)-2-(3-iodo-1H-indazol-6-yl)spiro[cyclopropane-1,3'-indolin]-2'-one from method 2 (PMB) was iodinated according to the method for (1R,2S)-2-(3-iodo-1H-indazol-6-yl)spiro[cyclopropane-1,3'-indolin]-2'-one. The resulting solid was further purified by column chromatography (silica gel, 3% MeOH in CH$_2$Cl$_2$) to give a beige solid (763 mg, 51% over 2 steps; >98% e.e.). $^1$H NMR and mass spectral data were identical to material obtained from Method 1.

Example 6

(1R,2S)-2-(3-iodo-1H-indazol-6-yl)-5'-methoxy-1'-methylspiro[cyclopropane-1,3'-indolin]-2'-one

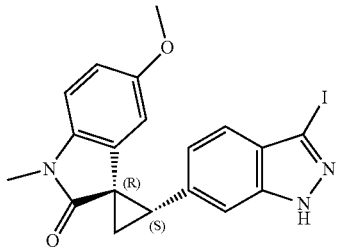

A. (1R,2S)-2-(1-benzyl-1H-indazol-6-yl)-5'-methoxy-1'-methylspiro[cyclopropane-1,3'-indolin]-2'-one

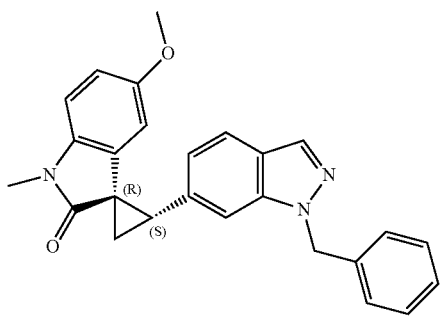

Method 1: The title compound was prepared in a manner similar to the method of (1R,2S)-1'-benzyl-2-(1-benzyl-1H-indazol-6-yl)spiro[cyclopropane-1,3'-indolin]-2'-one using (S)-1-(1-benzyl-1H-indazol-6-yl)ethane-1,2-diyl dimethanesulfonate (1.44 g, 3.39 mmol) and 5-methoxy-1-methylindolin-2-one (0.601 g, 3.39 mmol). Purification using Biotage Isolera (1-50% EtOAc in hexane, SNAP 25 g column) yielded the title compound (light brown solid, 1.05 g, 76%). $^1$H NMR (400 MHz, CDCl$_3$) δ 8.03 (s, 1H), 7.67 (d, J=8.8 Hz, 1H), 7.50 (s, 1H), 7.26-7.23 (m, 3H), 7.11 (d, J=7.6 Hz, 2H), 6.95 (d, J=8.4 Hz, 1H), 6.89 (d, J=8.4 Hz, 1H), 6.67 (d, J=8.4 Hz, 1H), 5.63 (d, J=16.4 Hz, 1H), 5.58 (d, J=16.0 Hz, 1H), 5.41 (s, 1H), 3.37 (t, J=8.8 Hz, 1H), 3.15 (s, 3H), 2.23-2.19 (m, 1H), 2.18-2.14 (m, 1H), —OCH$_3$ proton is obscured by methanol peak. MS ESI 410.2 [M+H]$^+$, calcd for [C$_{26}$H$_{23}$N$_3$O$_2$+H]$^+$410.2.

B. (1R,2S)-2-(1H-indazol-6-yl)-5'-methoxy-1'-methylspiro[cyclopropane-1,3'-indolin]-2'-one

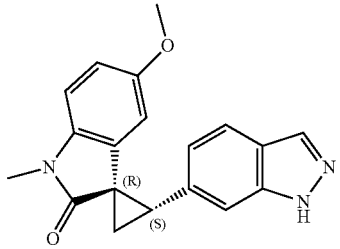

Method 1: A solution of potassium-t-butoxide (1M, 19.23 mL, 19.2 mmol) was added to a solution of (1R,2S)-2-(1-benzyl-1H-indazol-6-yl)-5'-methoxy-1'-methylspiro[cyclopropane-1,3'-indolin]-2'-one (0.875 g, 2.1 mmol) in anhydrous THF (2.62 mL) at 0° C. and the mixture was stirred for 15 min at the same temperature. Then anhydrous DMSO (1.97 mL, 27 mmol) was added via syringe to the mixture at 0° C. and stirring was continued for 5 min. The reaction mixture was purged O$_2$ gas for 1.5 h at 0° C. After stirring at 0° C. for a further 15 min, the reaction mixture was quenched with 25% aq. NH$_4$Cl (20 mL). The product was extracted using EtOAc (40 mL×2), and the combined EtOAc layer was washed with water (10 mL) and dried (Na$_2$SO$_4$) and concentrated under vacuum at 40° C./125 mbar. The resultant pale yellow residue was purified by silica gel column chromatography using 5-10% EtOAc in hexane to give the title compound as an off-white solid (445 mg, 65%). $^1$H NMR (400 MHz, CD$_3$OD) δ 8.02 (s, 1H), 7.67 (d, J=8.4 Hz, 1H), 7.47 (s, 1H), 6.95-6.90 (m, 2H), 6.68 (d, J=8.8 Hz, 1H), 5.58 (s, 1H), 3.38 (t, J=8.4 Hz, 1H), 3.20 (s, 3H), 2.28 (dd, J=9.2, 4.4 Hz, 1H), 2.06 (dd, J=8.4, 4.8 Hz, 1H), —OCH$_3$ proton is merged with Methanol peak. MS ESI 320.1 [M+H]$^+$, calcd for [C$_{19}$H$_{17}$N$_3$O$_2$+H]$^+$320.2.

Method 2: In a separate experiment in a similar manner to Example 6B) Method 1, the title compound was prepared using (1R,2S)-2-(1-benzyl-1H-indazol-6-yl)-5'-methoxy-1'-methylspiro[cyclopropane-1,3'-indolin]-2'-one (16 g, 39 mmol). The O$_2$ purge was carried out for 2.5 h between 0° to 15° C. After a further 15 min, the mixture was quenched with 20% aq. NH$_4$Cl, extracted with EtOAc, dried and evaporated to yield a semi solid residue. Cyclohexane (52 mL) and EtOAc (39 mL) were added, and the solid suspension was stirred at 70° C. for 30 min, then cooled to 5° C. and stirred for 30 min. The solid was filtered and washed with cyclohexane (5 mL×3) to give the title compound as a creamy solid (10 g, 1st crop). The residue obtained by evaporation of the filtrate was purified using Biotage Isolera (5-90% EtOAc in hexane, SNAP 25 g column) to give the 2nd crop (1.0 g). Total yield (11 g, 88%).

C. (1R,2S)-2-(3-iodo-1H-indazol-6-yl)-5'-methoxy-1'-methylspiro[cyclopropane-1,3'-indolin]-2'-one

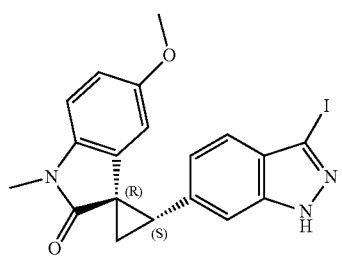

Method 1: In a manner similar to the method of (1R,2S)-2-(3-iodo-1H-indazol-6-yl)spiro[cyclopropane-1,3'-indolin]-2'-one using (1R,2S)-2-(1H-indazol-6-yl)-5'-methoxy-1'-methylspiro[cyclopropane-1,3'-indolin]-2'-one (1.34 g, 4.19 mmol), the title compound was obtained as a cream color solid (1.71 g, 91%; 98% e.e.) with the major (1R,2S) enantiomer eluting at 2.6 min (Phenomenex Lux 5μ Amylose-2 150×4.6 mm, 2.5 mL/min with isocratic at 20% EtOH in hexane for 0.5 min, then gradient 20-50% EtOH in hexane over 2.5 min, then isocratic at 50% for 1 min). From the racemic reference standard, the retention time of the (1S,2R) enantiomer was 3.25 min using this method. $^1$H NMR (400 MHz, CDCl$_3$) δ 10.38 (s, 1H), 7.42 (d, J=8.4 Hz, 1H), 7.35 (s, 1H), 7.04 (d, J=8.8 Hz, 1H), 6.77 (d, J=8.4 Hz, 1H), 6.66 (d, J=8.4 Hz, 1H), 5.53 (s, 1H), 3.46 (t, J=8.0 Hz, 1H), 3.38 (s, 3H), 3.32 (s, 3H), 2.24 (dd, J=8.4, 4.8 Hz, 1H), 2.04 (dd, J=12.4, 4.8 Hz, 1H); MS ESI 446.1 [M+H]$^+$, calcd for [C$_{19}$H$_{16}$IN$_3$O$_2$+H]$^+$ 446.0. Optical Rotation: [α]$^{22}_D$=−134° (c 0.238, MeOH).

Method 2: In a manner similar to the method of (1R,2S)-2-(3-iodo-1H-indazol-6-yl)spiro[cyclopropane-1,3'-indolin]-2'-one using (1R,2S)-2-(1H-indazol-6-yl)-5'-methoxy-1'-methylspiro[cyclopropane-1,3'-indolin]-2'-one (11 g, 34 mmol), the crude product (20 g) was obtained by filtration. This solid was suspended in IPA (60 mL) and stirred at 75° C. for 30 min, then cooled to 5° C. and stirred for 30 min. Filtration of the solid, using IPA (10 mL×2) to rinse, provided the title compound as a creamy solid (10.2 g, 1st crop, 99.5% e.e. by HPLC as for method 1). Optical Rotation: [α]$^{22}_D$=−136.7° (c 1.08, MeOH). The residue obtained by evaporation of the filtrate was purified using Biotage Isolera (0-80% EtOAc in hexane, SNAP 50 g column) to yield a 2nd crop (2.8 g, 97.9% e.e. by HPLC as for method 1). Total yield (13 g, 84.7%).

Example 7

(1R,2S)-2-(3-iodo-1H-indazol-6-yl)-1'-(2-methoxyethyl)spiro[cyclopropane-1,3'-indolin]-2'-one

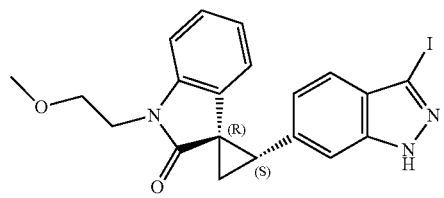

A. (1R,2S)-1'-benzyl-2-(1-benzyl-1H-indazol-6-yl)-1'-(2-methoxyethyl)spiro[cyclopropane-1,3'-indolin]-2'-one

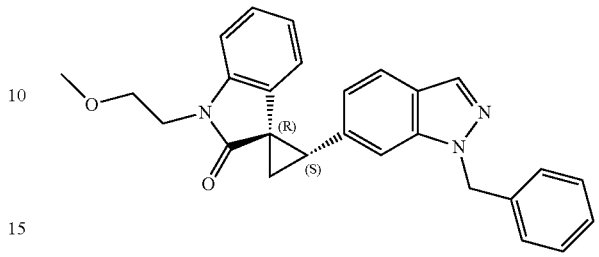

The title compound was prepared in a manner similar to the method of (1R,2S)-1'-benzyl-2-(1-benzyl-1H-indazol-6-yl)spiro[cyclopropane-1,3'-indolin]-2'-one using (S)-1-(1-benzyl-1H-indazol-6-yl)ethane-1,2-diyl dimethanesulfonate (1.22 g, 2.87 mmol) and 1-(2-methoxyethyl)indolin-2-one (550.0 mg, 2.87 mmol). Purification on Biotage Isolera (0-60% EtOAc in hexane, SNAP 25 g column) yielded the title compound as a pale brown solid (774 mg, 64%). $^1$H NMR (400 MHz, CDCl$_3$) δ 8.01 (s, 1H), 7.60 (d, J=8.0 Hz, 1H), 7.29-7.27 (m, 3H), 7.19 (s, 1H), 7.14-7.09 (m, 3H), 6.98 (d, J=7.6 Hz, 1H), 6.92 (d, J=8.4 Hz, 1H), 6.54 (t, J=7.2 Hz, 1H), 5.75 (d, J=7.6 Hz, 1H), 5.60 (t, J=16.0 Hz, 1H), 5.51 (d, J=16.0 Hz, 1H), 4.08-4.03 (m, 1H), 4.00-3.95 (m, 1H), 3.69 (t, J=5.6 Hz, 2H), 3.43 (t, J=8.0 Hz, 1H), 3.38 (s, 3H), 2.24 (dd, J=9.2, 4.8 Hz, 1H), 2.00 (dd, J=8.4, 5.6 Hz, 1H); MS ESI 424.2 [M+H]$^+$, calcd for [C$_{27}$H$_{25}$N$_3$O$_2$+H]$^+$ 424.2.

B. (1R,2S)-2-(1H-indazol-6-yl)-1'-(2-methoxyethyl)spiro[cyclopropane-1,3'-indolin]-2'-one

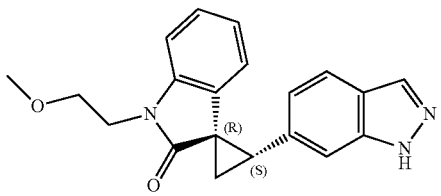

A solution of KO$^t$Bu (1M, 11.97 mL, 11.9 mmol) was added to a solution of (1R,2S)-2-(1H-indazol-6-yl)-1'-(2-methoxyethyl)spiro[cyclopropane-1,3'-indolin]-2'-one (390 mg, 0.92 mmol) in anhydrous THF (1.95 mL) at 0° C. and the mixture was stirred for 15 min at the same temperature. Then anhydrous DMSO (1.18 mL, 16.6 mmol) was added via syringe to the mixture in single lot at 0° C. and stirring was continued for 5 min. Then, reaction mixture was purged with O$_2$ gas for 1.5 h at 0° C. After stirring at 0° C. for a further 15 min, reaction mixture was quenched with 25% aq. NH$_4$Cl (10 mL). The product was extracted using EtOAc (20 mL×2), and the combined EtOAc layer was washed with water (10 mL) and dried over anhydrous sodium sulfate and concentrated under vacuum at 40° C./125 mbar. The resultant pale yellowish residue was purified by flash chromatography on Biotage Isolera (using 5-10% EtOAc in hexane, SNAP 25 g column) to give the title compound as a white solid (205 mg, 67%). $^1$H NMR (400 MHz, CDCl$_3$) δ 8.08 (s, 1H), 7.65 (d, J=8.4 Hz, 1H), 7.42 (s, 1H), 7.12 (t, J=7.6 Hz, 1H), 7.00 (t, J=8.0 Hz, 2H), 6.60 (t, J=7.6 Hz, 1H), 5.90 (d, J=7.2 Hz, 1H), 4.10-3.97 (m, 2H), 3.70 (t, J=5.6 Hz, 2H), 3.47 (t, J=8.4 Hz, 1H), 3.38 (s, 3H), 2.29 (dd, J=8.8, 4.4 Hz, 1H), 2.08 (dd, J=6.8, 4.4 Hz, 1H); MS ESI 334.2 [M+H]⁺, calcd for [C₂₀H₁₉N₃O₂+H]⁺334.2.

C. (1R,2S)-2-(3-iodo-1H-indazol-6-yl)-1'-(2-methoxyethyl)spiro[cyclopropane-1,3'-indolin]-2'-one

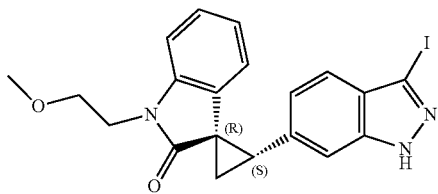

The title compound was prepared in a manner similar to the method of (1R,2S)-2-(3-iodo-1H-indazol-6-yl)spiro[cyclopropane-1,3'-indolin]-2'-one using (1R,2S)-2-(1H-indazol-6-yl)-1'-(2-methoxyethyl)spiro[cyclopropane-1,3'-indolin]-2'-one (260 mg, 0.779 mmol). Purification using 0-30% EtOAc in hexane on Biotage Isolera with SNAP 25 g column yielded the title compound as a white solid (235 mg, 66%; 98% e.e.) with the major (1R,2S) enantiomer eluting at 2.6 min (Phenomenex Lux 5µ Amylose-2 150×4.6 mm, 2.5 mL/min with isocratic at 20% EtOH in hexane for 0.5 min, then gradient 20-50% EtOH in hexane over 2.5 min, then isocratic at 50% for 1 min). From the racemic reference standard, the retention time of the (1S,2R) enantiomer was 3.2 min using this method. ¹H NMR (400 MHz, CDCl₃) δ 10.39 (s, 1H), 7.40 (d, J=8.8 Hz, 1H), 7.34 (s, 1H), 7.14 (t, J=7.6 Hz, 1H), 7.06-7.01 (m, 2H), 6.63 (t, J=7.2 Hz, 1H), 5.87 (d, J=7.6 Hz, 1H), 4.14-3.97 (bm, 2H), 3.70 (t, J=5.6 Hz, 2H), 3.46 (t, J=7.6 Hz, 1H), 3.39 (s, 3H), 2.28-2.26 (m, 1H), 2.05-2.01 (m, 1H); MS ESI 460.1 [M+H]⁺, calcd for [C₂₀H₁₈IN₃O₂+H]⁺460.0. Optical Rotation: [α]²²_D=−239° (c 0.243, MeOH).

Suzuki Coupling of Chiral
Indazolyl-Spiro-Cyclopropane-Indolinone-Iodides

Example 8

(1R,2S)-(E)-2-(3-(4-((cis-2,6-dimethylmorpholino)methyl)stryl)-1H-indazol-6-yl)spiro[cyclopropane-1,3'-indolin]-2'-one

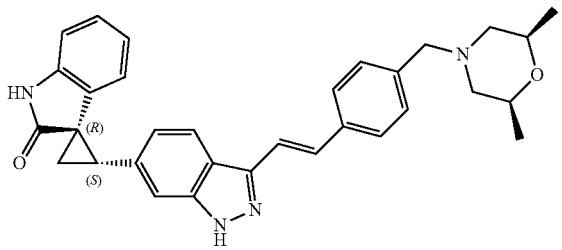

A. 4-(4-bromobenzyl)-cis-2,6-dimethylmorpholine

To a mixture of 4-bromobenzaldehyde (3.70 g, 20 mmol) and cis-2,6-dimethylmorpholine (2.52 g, 22 mmol) in DCE (100 mL) was added NaBH(OAc)₃ (5.30 g, 25 mmol), followed by AcOH (0.5 mL). After addition, the resulting mixture was stirred O/N at rt. The reaction as quenched with sat. NaHCO₃ (30 mL) and H₂O (30 mL), and was extracted with DCM (30 mL×2). Concentration of the solvents afforded the crude title compound as a pale yellow liquid (6.41 g, quantitative yield). ¹H NMR (400 MHz, CDCl₃) δ 7.45 (d, J=7.2 Hz, 2H), 7.21 (d, J=7.2 Hz, 2H), 3.64-3.55 (m, 2H), 3.44 (s, 2H), 2.68 (d, J=11.6 Hz, 2H), 1.75 (t, J=11.0 Hz, 2H), 1.54 (d, J=6.0 Hz, 6H); MS ESI 284.0 [M+H]⁺, calcd for [C₁₃H₁₈BrNO+H]⁺284.1.

B. (Cis-2,6-dimethyl-4-(4-((E)-2-(4,4,5,5-tetramethyl-1,3,2-dioxaborolan-2-yl)vinyl)benzyl)morpholine To a solution of 4-(4-bromobenzyl)-cis-2,6-dimethylmorpholine (20 g, 71 mmol) and 4,4,5,5-tetramethyl-2-vinyl-1,3,2-dioxaborolane (13 mL, 77 mmol, 1.1 eq.) in toluene (250 mL) was added triethylamine (19.7 mL, 142 mmol) and Pd(P'Bu₃)₂ (368 mg, 0.71 mmol) and the solution was heated to 80° C. for 2 h under argon. After cooling to rt, the reaction was quenched with sat. NaHCO₃ (50 mL), water (50 mL), extracted with EtOAc (3×100 mL) and dried over MgSO₄. After evaporation of the solvents, the residue was purified by Biotage column system (EtOAc/hex gradient: 0-100%) to give the title compound as a white solid (16 g, 64%). ¹H NMR (400 MHz, CDCl₃) δ 7.46 (d, J=8.0 Hz, 2H), 7.40 (d, J=18.4 Hz, 1H), 7.30 (d, J=7.6 Hz, 2H), 6.16 (d, J=18.4 Hz, 1H), 3.75-3.65 (m, 2H), 3.47 (s, 2H), 2.70 (d, J=10.8 Hz, 2H), 1.75 (t, J=10.2 Hz, 2H), 1.32 (s, 12H), 1.14 (d, J=6.4 Hz, 6H); MS ESI 358.2 [M+H]⁺, calcd for [C₂₁H₃₂BNO₃+H]⁺358.2.

C. (1R,2S)-(E)-2-(3-(4-((cis-2,6-dimethylmorpholino)methyl)styryl)-1H-indazol-6-yl)spiro[cyclopropane-1,3'-indolin]-2'-one hydrochloride A mixture of (1R,2S)-2-(3-iodo-1H-indazol-6-yl)spiro [cyclopropane-1,3'-indolin]-2'-one (obtained from example 1C, 8.0 g, 20 mmol) and cis-2,6-dimethyl-4-(4-((E)-2-(4,4,5,5-tetramethyl-1,3,2-dioxaborolan-2-yl)vinyl)benzyl)morpholine (8.4 g, 24 mmol) in PhCH₃ (100 mL) and EtOH (50 mL), with 1M Na₂CO₃ (40 mL, 40 mmol) and Pd(PPh₃)₄ (924 mg, 0.8 mmol, 4 mol %) was heated at 110° C. for 2 h in an oil bath. The solution was cooled to rt and was diluted with ethyl acetate (500 mL). The solution was washed with water (2×50 mL), brine (50 mL) and dried over MgSO₄. The solution was concentrated to and orange oil which was purified by column chromatography (gradient 0-10% MeOH in CH₂Cl₂) to give free base of the title compound as a yellow foam. The product was dissolved into CH₂Cl₂ (10 mL) and added dropwise into a solution of diethyl ether (150 mL) containing 15 mL of 1M HCl in ether. The resulting precipitate was filtered, dissolved into water and lyophilized to give the title compound as a yellow powder (5.6 g, 51%, 97.5% e.e. as determined by chiral SFC with the major (1R,2S) enantiomer eluting at 5.2 min (Chiralcel OJ-H (15×0.46 cm) 40% methanol (0.1% DEA)/CO₂; 100 bar 3 mL/min; Detection 220 and 254 nm); From the racemic reference standard, the retention time of the (1S,2R) enantiomer was 2.5 min using this method); ¹H NMR (CD₃OD) δ: 8.03 (d, J=8.3 Hz, 1H), 7.78 (d, J=8.3 Hz, 2H), 7.63-7.52 (m, 4H), 7.49 (s, 1H), 7.09-7.02 (m, 2H), 6.94 (d, J=7.8 Hz, 1H), 6.58 (t, J=7.5 Hz, 1H), 5.99 (d, J=7.5 Hz, 1H), 4.37 (s, 2H), 3.94-3.84 (m, 2H), 3.41-3.34 (m, 3H), 2.79 (t, J=11.8 Hz, 2H), 2.25 (dd, J=7.9, 4.6 Hz, 1H), 2.19 (dd, J=9.0, 4.8 Hz, 1H), 1.24 (d, J=6.3 Hz, 6H); [M+H]$^+$, calcd for [C$_{32}$H$_{32}$N$_4$O$_2$+H]$^+$505.3; Optical Rotation [α]$^{21}_D$=−165° (c 0.52, MeOH).

Example 9

(1R,2S)-(E)-5'-fluoro-2-(3-(4-(morpholinomethyl) styryl-1H-indazol-6-yl)spiro [cyclopropane-1,3'-indolin]-2'-one 2,2,2-trifluoroacetate

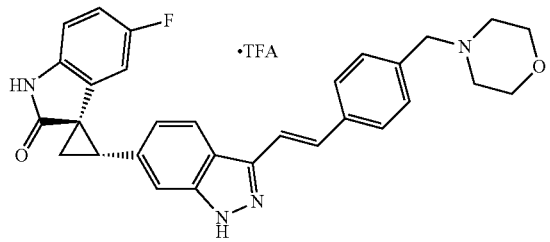 [SMILES: O=C1Nc2ccc(F)cc2[C@]12C[C@H]2c1ccc2c(/C=C/c3ccc(CN4CCOCC4)cc3)n[nH]c2c1]

A. (E)-4-(4-(2-(4,4,5,5-tetramethyl-1,3,2-dioxaborolan-2-yl)vinyl)benzyl)morpholine To a mixture of 4-(4-bromobenzyl)morpholine (4.18 g, 16.3 mmol) and 4,4,5,5-tetramethyl-2-vinyl-1,3,2-dioxaborolane (3 mL, 17.7 mmol, 1.1 eq.) and toluene (30 mL) in a 20 mL microwave vial was added Et$_3$N (4.56 mL, 32.4 mmol, 2 eq.), followed by Pd(P$^t$Bu$_3$)$_2$ (83 mg, 0.16 mmol, 1 mol %). The resulting mixture was purged with argon, then capped and heated at 80° C. oil bath for 1 h. After cooling to rt, the reaction was diluted with half saturated NaHCO$_3$ (40 mL) and the product was extracted with EtOAc (2×60 mL). The organic layer was dried (Na$_2$SO$_4$) and the solvent was evaporated in vacuo. Trituration with hexane and sonication provided a solid that was collected by suction filtration (white solid, 2.55 g). After evaporation of the solvent in vacuo, the residue solidified and a second crop of crystals was obtained by suction filtration from a small amount of hexane (pale yellow crystals, 0.22 g). Evaporation of the mother liquor provided a yellow liquid which was purified using Biotage Isolera (20-80% EtOAc in hexane, SNAP-50 g column) to give a third portion of the product (yellow solid, 1.58 g; total yield 4.35 g, 71%). $^1$H NMR (400 MHz, CDCl$_3$) δ 7.45 (d, J=8.0 Hz, 2H), 7.40 (d, J=18.4 Hz, 1H), 7.31 (d, J=8.0 Hz, 2H), 6.16 (d, J=18.0 Hz, 1H), 3.72 (t, J=4.4 Hz, 4H), 3.50 (s, 2H), 2.47-2.42 (m, 4H), 1.32 (s, 12H); MS ESI 330.1 [M+H]$^+$, calcd for [C$_{19}$H$_{28}$BNO$_3$+H]$^+$ 330.2.

B. (1R,2S)-(E)-5' fluoro-2-(3-(4-(morpholinomethyl)styryl)-1H-indazol-6-yl)spiro[cyclopropane-1, 3'-indolin]-2'-one 2,2,2-trifluoroacetate To a mixture of (1R,2S)-5'-fluoro-2-(3-iodo-1H-indazol-6-yl)spiro[cyclopropane-1,3'-indolin]-2'-one (Example 2C, 240.0 mg, 0.571 mmol) and (E)-4-(4-(2-(4,4,5,5-tetramethyl-1,3,2-dioxaborolan-2-yl)vinyl)benzyl)morpholine (216.7 mg, 0.658 mmol) in PhCH$_3$/EtOH (7.2 mL/3.6 mL) in a 20 mL microwave vial was added 1M Na$_2$CO$_3$ (1.14 mL, 1.14 mmol), followed by Pd(PPh$_3$)$_4$ (16.5 mg, 0.014 mmol, 2.5 mol %). The resulting mixture was purged with argon, then heated to 120° C. for 2 h under microwave irradiation. After cooling to rt, the reaction was diluted with H$_2$O (5 mL). The product was extracted with EtOAc (20 mL×2) and the organic layer was washed with brine (5 mL) and dried (Na$_2$SO$_4$). After the solvent was evaporated in vacuo, purification by preparative HPLC gave the title compound as a cream solid (230 mg, 66%, TFA salt). $^1$H NMR (400 MHz, CD$_3$OD) δ 8.04 (d, J=8.8 Hz, 1H), 7.77 (d, J=7.2 Hz, 2H), 7.59-7.52 (m, 5H), 7.05 (d, J=8.0 Hz, 1H), 6.91-6.88 (m, 1H), 6.79 (t, J=8.0 Hz, 1H), 5.74 (d, J=8.8 Hz, 1H), 4.39 (s, 2H), 4.08-4.05 (bm, 2H), 3.76-3.70 (bt, 2H), 3.42-3.35 (m, 3H), 3.26-3.23 (bm, 2H), 2.30 (t, J=5.6 Hz, 1H), 2.24-2.20 (m, 1H); MS ESI 495.3 [M+H]$^+$, calcd for [C$_{30}$H$_{27}$FN$_4$O$_2$+H]$^+$495.22. Optical Rotation: [α]$^{22}_D$=−136° (c 0.404, MeOH).

Example 10

(1R,2S)-(E)-5'-methyl-2-(3-(4-(morpholinomethyl) styryl)-1H-indazol-6-yl)spiro[cyclopropane-1,3'-indolin]-2'-one 2,2,2-trifluoroacetate

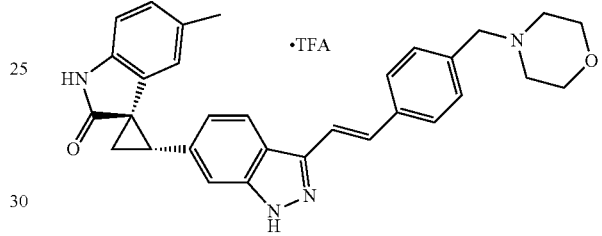

The title compound (470 mg, 78%, TFA salt) was obtained as a yellow solid from (1R,2S)-2-(3-iodo-1H-indazol-6-yl)-5'-methylspiro[cyclopropane-1,3'-indolin]-2'-one (Example 3C, 415 mg, 1 mmol) and (E)-4-(4-(2-(4,4,5,5-tetramethyl-1,3,2-dioxaborolan-2-yl)vinyl)benzyl) morpholine (329 mg, 1 mmol) using the method for the preparation of Example 9B (PhCH$_3$/EtOH=4.5 mL/9 mL, 2 mol % Pd(PPh$_3$)$_4$, 110° C., 2 h). $^1$H NMR (400 MHz, CD$_3$OD) δ 7.73 (d, J=8.4 Hz, 1H), 7.53 (d, J=8.0 Hz, 2H), 7.44 (d, J=8.0 Hz, 2H), 7.38 (s, 1H), 7.32 (d, J=16.8 Hz, 1H), 7.27 (d, J=16.8 Hz, 1H), 6.82 (d, J=8.4 Hz, 1H), 6.77 (d, J=8.0 Hz, 1H), 6.73 (d, J=8.0 Hz, 1H), 5.78 (s, 1H), 4.29 (s, 2H), 3.99 (d, J=11.2 Hz, 2H), 3.75 (t, J=11.6 Hz, 2H), 3.42-3.32 (m, 2H), 3.21 (t, J=8.4 Hz, 1H), 3.18-3.08 (m, 2H), 2.09-2.01 (m, 2H), 1.72 (s, 3H); MS ESI 491.3 [M+H]$^+$, calcd for [C$_{31}$H$_{30}$N$_4$O$_2$+H]$^+$491.2. Optical Rotation: [α]$^{23}_D$=−89° (c 0.28, MeOH).

Example 11

(1R,2S)-5'-methoxy-2-(3-(4-(4-methylpiperazin-1-yl)phenyl)-1H-indazol-6-yl)spiro[cyclopropane-1,3'-indolin]-2'-one hydrochloride

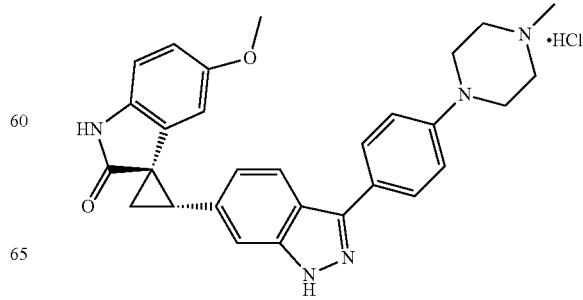

A mixture of (1R,2S)-2-(3-iodo-1H-indazol-6-yl)-5'-methoxyspiro[cyclopropane-1,3'-indolin]-2'-one (Example 4C, 540 mg, 1.25 mmol), 1-methyl-4-(4-(4,4,5,5-tetramethyl-1,3,2-dioxaborolan-2-yl)phenyl)piperazine (416 mg, 1.38 mmol), Pd(PPh$_3$)$_4$ (7 mg, 0.06 mmol), LiCl (159 mg, 3.75 mmol) and 1M Na$_2$CO$_3$ (6.3 mL, 6.3 mmol) in dioxane (20 mL) was heated to reflux in an oil bath until the iodide had been consumed as determined by LCMS. The reaction was then allowed to cool to room temperature and was diluted with EtOAc and water was added. The resulting mixture was extracted with EtOAc and the combined organic extracts were washed with brine, dried over MgSO$_4$ and concentrated to give an orange solid. The title compound was purified by silica gel chromatography (95:3:2 to 85:13:2 CH$_2$Cl$_2$/MeOH/NH$_3$) to yield a yellow solid. HCl (1M in diethyl ether, 3.1 mL, 3.1 mmol) was added in a dropwise manner to a solution of (1R,2S)-5'-methoxy-2-(3-(4-(4-methylpiperazin-1-yl)phenyl)-1H-indazol-6-yl)spiro[cyclopropane-1,3'-indolin]-2'-one (240 mg, 0.500 mmol) in THF (1 mL). A yellow precipitate formed and the solid was then filtered and washed with ether (2 mL) giving the title compound (256 mg, 42%, HCl salt). $^1$H NMR (400 MHz, CD$_3$OD) δ 7.94 (d, J=8.2 Hz, 1H), 7.88 (d, J=8.4 Hz, 2H), 7.52 (s, 1H), 7.19 (d, J=8.6 Hz, 2H), 7.05 (d, J=8.2 Hz, 1H), 6.84 (d, J=8.4 Hz, 1H), 6.62 (d, J=7.7 Hz, 1H), 5.62 (s, 1H), 4.01-3.98 (m, 2H), 3.67-3.64 (m, 2H), 3.39-3.32 (m, 3H), 3.28 (s, 3H), 3.18-3.11 (m, 2H), 3.00 (s, 3H), 2.28-2.25 (m, 1H), 2.21-2.18 (m, 1H); MS ESI 480.4 [M+H]$^+$, calcd for [C$_{29}$H$_{29}$N$_5$O$_2$+H]$^+$ 480.23. Optical Rotation: [α]$^{22}_D$=−126° (c 0.40, MeOH).

Example 12

(1R,2S)-(E)-1'-methyl-2-(3-(4-(pyrrolidin-1-ylmethyl)styryl)-1H-indazol-6-yl)spiro[cyclopropane-1,3'-indolin]-2'-one 2,2,2-trifluoroacetate

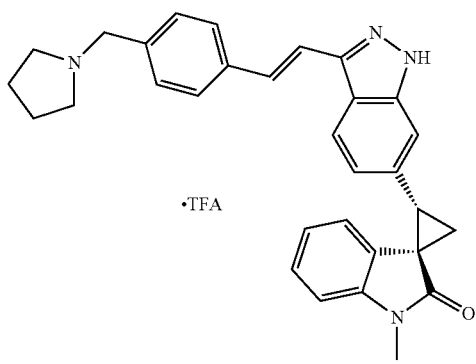 [SMILES: CN1C(=O)[C@@]2(C[C@H]2c2ccc3c(/C=C/c4ccc(CN5CCCC5)cc4)n[nH]c3c2)c2ccccc21]

A. 1-(4-ethynylphenyl)pyrrolidine

Glacial acetic acid (0.2 mL) was added to a mixture of 4-ethynylbenzaldehyde (1 g, 7.5 mmol), pyrrolidine (1.2 mL, 15 mmol) and NaBH(OAc)$_3$ (2.5 g, 11.5 mmol) in DCE (35 mL). The resulting mixture was stirred for 2 h at rt. The reaction was quenched with saturated aqueous NaHCO$_3$ (50 mL). The product was extracted into CH$_2$Cl$_2$ (2×100 mL), and the combined organic layer was washed with brine (25 mL), dried (MgSO$_4$) and evaporated in vacuo to give 1-(4-ethynylphenyl)pyrrolidine in quantitative yield. $^1$H NMR (CDCl$_3$) δ: 7.45 (d, J=7.8 Hz, 2H), 7.30 (d, J=8.3 Hz, 2H), 3.62 (s, 2H), 3.06 (s, 1H), 2.51 (bs, 4H), 1.80 (bs, 4H).

B. ((E)-1-(4-(2-(4,4,5,5-tetramethyl-1,3,2-dioxaborolan-2-yl)vinyl)benzyl)pyrrolidine To a solution of 4,4,5,5-tetramethyl-1,3,2-dioxaborolane (1.9 g, 15 mmol) in toluene (20 mL) was added 1-(4-ethynylphenyl)pyrrolidine (1 g, 5 mmol) and HRuCl(CO)(PPh$_3$)$_3$ (120 mg, 0.11 mmol) under argon. The resulting mixture was heated at 50° C. for 4 h. The product was extracted into EtOAc (250 mL), and the organic layer was washed sequentially with water (3×20 mL) and brine (20 mL), dried (MgSO$_4$) and evaporated in vacuo. Purification by column chromatography (silica gel, 0-20% MeOH/EtOAc) gave the title compound (1.2 g, 77%). $^1$H NMR (400 MHz, CDCl$_3$) δ 7.45 (d, J=7.8 Hz, 2H), 7.39 (d, J=18.6 Hz, 1H), 7.33-7.29 (m, 2H), 6.15 (d, J=18.6 Hz, 1H), 3.61 (s, 2H), 2.51 (bs, 4H), 1.79 (bs, 4H), 1.32 (s, 12H).

C. (1R,2S)-(E)-1'-methyl-2-(3-(4-(pyrrolidin-1-ylmethyl)styryl)-1H-indazol-6-yl)spiro[cyclopropane-1,3'-indolin]-2'-one 2,2,2-trifluoroacetate A round-bottom flask was charged with (1R,2S)-2-(3-iodo-1H-indazol-6-yl)-1'-methylspiro[cyclopropane-1,3'-indolin]-2'-one (Example 5D, 147 mg, 0.353 mmol), (E)-1-(4-(2-(4,4,5,5-tetramethyl-1,3,2-dioxaborolan-2-yl)vinyl)benzyl)pyrrolidine (133 mg, 0.424 mmol), LiCl (45 mg, 1.06 mmol), dioxane (3.5 mL), and 1M Na$_2$CO$_{3(aq)}$ (1.8 mL, 1.8 mmol). The mixture was purged with a balloon of Ar$_{(g)}$ for 15 min and then Pd(PPh$_3$)$_4$ (13 mg, 0.011 mmol) was added and the reaction heated to 100° C. for 18 h. After the reaction mixture was cooled, saturated NaHCO$_3$ was added and the product was extracted into EtOAc. The organic layer was washed with sequentially with saturated NaHCO$_3$ and brine, and dried over MgSO$_4$. After the solvent was removed in vacuo, purification by prep-HPLC gave the title compound as an pale-yellow solid (46 mg, 22%, TFA salt); $^1$H NMR (400 MHz, CD$_3$OD) δ 7.98 (d, 1H, J=8.7 Hz), 7.73 (d, 2H, J=7.4 Hz), 7.53-7.44 (m, 5H), 7.14 (t, 1H, J=7.2 Hz), 7.01 (d, 2H, J=7.9 Hz), 6.63 (t, 1H, J=7.4 Hz), 6.01 (d, 1H, J=7.6 Hz), 4.38 (s, 2H), 3.55-3.45 (m, 2H), 3.40-3.32 (m, 1H), 3.34 (s, 3H), 3.26-3.16 (m, 2H), 2.28-2.17 (m, 4H), 2.05-1.95 (m, 2H); MS ESI [M+H]$^+$ 475.4, calcd for [C$_{31}$H$_{30}$N$_4$O+H]$^+$ 475.25. Optical Rotation: [α]$^{22}_D$=−148° (c 0.40, MeOH).

Example 13

(1R,2S)-5'-methoxy-1'-methyl-2-(3-(4-(piperazin-1-yl)phenyl)-1H-indazol-6-yl)spiro[cyclopropane-1,3'-indolin]-2'-one 2,2,2-trifluoroacetate

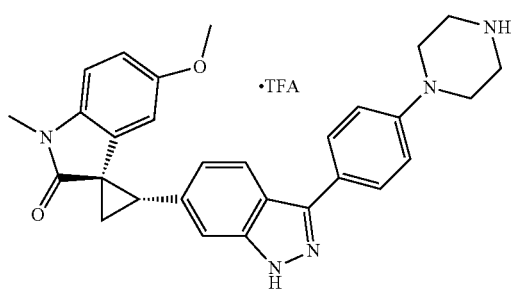 [SMILES: COc1ccc2c(c1)[C@]1(C[C@H]1c1ccc3c(-c4ccc(N5CCNCC5)cc4)n[nH]c3c1)C(=O)N2C ; "·TFA"]

The Boc protected title compound was synthesized according to the method of Example 9B, except substituting (1R,2S)-2-(3-iodo-1H-indazol-6-yl)-5'-methoxy-1'-methyl-spiro[cyclopropane-1,3'-indolin]-2'-one (Example 6C, 600 mg, 1.35 mmol) and tert-butyl 4-(4-(4,4,5,5-tetramethyl-1,3,2-dioxaborolan-2-yl)phenyl)piperazine-1-carboxylate (534 mg, 1.37 mmol). The Boc protected compound was purified by column chromatography (silica gel, hexanes/EtOAc, 100:0 to 5:95) which gave 400 mg. This material was dissolved in $CH_2Cl_2$ (12 mL) and TFA (3 mL) and the reaction stirred for 3 h at which time the solvent was removed and the residue purified by prep-HPLC which yielded the title product as a pale-yellow solid (339 mg, 42%, TFA salt); $^1$H NMR (400 MHz, $CD_3OD$) δ 7.90 (d, J=8.2 Hz, 1H), 7.86 (d, J=8.4 Hz, 2H), 7.48 (s, 1H), 7.17 (d, J=8.4 Hz, 2H), 7.00 (d J=8.6 Hz, 1H,), 6.92 (d, J=8.5 Hz, 1H), 6.69 (d, J=8.6 Hz, 1H), 5.64 (s, 1H), 3.53-3.48 (m, 4H), 3.43-3.37 (m, 5H), 3.31 (s, 3H), 3.29 (s, 3H), 2.29-2.26 (m, 1H), 2.22-2.18 (m, 1H); MS ESI [M+H]$^+$480.3, calcd for [$C_{29}H_{29}N_5O_2$+H]$^+$480.24. Optical Rotation: $[α]^{22}_D$=−113° (c 0.62, MeOH).

Example 14

(1R,2S)-(E)-2-(3-(4-((dimethylamino)methyl)styryl)-1H-indazol-6-yl)-1'-(2-methoxyethyl)spiro[cyclopropane-1,3'-indolin]-2'-one 2,2,2-trifluoroacetate

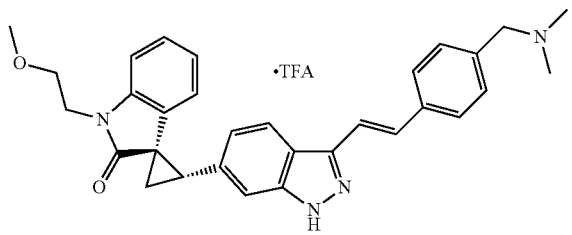

The title compound was synthesized according to the method of Example 9B, by using (1R,2S)-2-(3-iodo-1H-indazol-6-yl)-1'-(2-methoxyethyl)spiro[cyclopropane-1,3'-indolin]-2'-one (Example 7C, 490 mg, 1.07 mmol) and (E)-N,N-dimethyl-1(4-(2-(4,4,5,5-tetramethyl-1,3,2-dioxaborolan-2-yl)vinyl)benzyl)methanamine (321.7 mg, 1.12 mmol). Purification by preparative HPLC gave the title compound as an off-white solid (297 mg, 46%, TFA salt). $^1$H NMR (400 MHz, $CD_3OD$) δ 7.90 (d, J=8.0 Hz, 1H), 7.68 (d, J=7.6 Hz, 2H), 7.50-7.42 (m, 5H), 7.08-7.03 (m, 2H), 6.93 (d, J=8.4 Hz, 1H), 6.55 (t, J=7.6 Hz, 1H), 5.96 (d, J=7.6 Hz, 1H), 4.30 (s, 2H), 4.01 (t, J=4.8 Hz, 2H), 3.67 (t, J=5.2 Hz, 2H), 3.35-3.31 (m, 4H), 2.86 (s, 6H), 2.21-2.20 (m, 1H), 2.17-2.14 (m, 1H); MS ESI 493.4 [M+H]$^+$, calcd for [$C_{31}H_{32}N_4O_2$+H]$^+$493.26. Optical Rotation: $[α]^{23}_D$=−169° (c 0.36, MeOH).

Example 15

(1R,2S)-(E)-2-(3-(4-((cis-2,6-dimethylmorpholino)methyl)styryl)-1H-indazol-6-yl)-5'-methoxyspiro[cyclopropane-1,3'-indolin]-2'-one hydrochloride

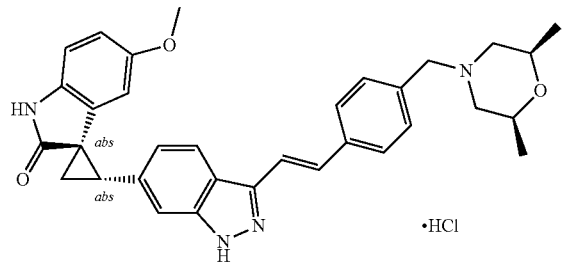 [SMILES: COc1ccc2c(c1)[C@]1(C[C@H]1c1ccc3c(/C=C/c4ccc(CN5C[C@@H](C)O[C@@H](C)C5)cc4)n[nH]c3c1)C(=O)N2 ; Cl]

The title compound was obtained according to the method for Example 8C from (1R,2S)-2-(3-iodo-1H-indazol-6-yl)-5'-methoxyspiro[cyclopropane-1,3'-indolin]-2'-one (obtained from preparative HPLC separation Example 4C method 3, 5.5 g, 12.7 mmol) and cis-2,6-dimethyl-4-(4-((E)-2-(4,4,5,5-tetramethyl-1,3,2-dioxaborolan-2-yl)vinyl)benzyl)morpholine (5.21 g, 14.6 mmol) with Pd(PPh$_3$)$_4$ (294 mg, 0.25 mmol, 2 mol %) and Na$_2$CO$_3$ (1M, 25.5 mL, 25.5 mmol) in PhCH$_3$ (80 mL) and EtOH (40 mL) at 110° C. for 18 h in oil bath. Purification gave the title compound as a yellow solid (3.44 g, 47%, HCl salt, 99.8% e.e. as determined by chiral SFC with the major (1R,2S) enantiomer eluting at 3.9 min (Chiralpak AS-H (25×0.46 cm); 40% ethanol (0.1% DEA)/CO$_2$, 100 bar; 3 mL/min; Detection: 254, 220 nm); From the racemic reference standard, the retention time of the (1S,2R) enantiomer was 2.0 min using this method); $^1$H NMR (400 MHz, CD$_3$OD) δ 8.00 (d, J=8.3 Hz, 1 H), 7.74 (d, J=7.5 Hz, 2 H), 7.63 (d, J=7.6 Hz, 2 H), 7.58-7.51 (m, 2 H), 7.47 (d, J=16.8 Hz, 1 H), 7.05 (d, J=8.0 Hz, 1 H), 6.84 (d, J=8.3 Hz, 1 H), 6.59 (dd, J=8.4, 2.1 Hz, 1 H), 5.61 (m, 1 H), 4.38 (s, 2 H), 4.02-3.89 (m, 2 H), 3.42-3.32 (m, 3 H), 3.26 (s, 3 H), 2.79 (t, J=11.4 Hz, 2 H), 2.27-2.21 (m, 1 H), 2.16 (dd, J=8.9, 4.4 Hz, 1 H), 1.22 (d, J=6.0 Hz, 6 H); MS ESI 535.3 [M+H]$^+$, calcd for [$C_{33}H_{34}N_4O_3$+H]$^+$535.26; Optical Rotation $[α]^{22}_D$=−103° (c 0.55, MeOH).

Example 16

(1R,2S)-(E)-5'-methoxy-1'-methyl-2-(3-(4-(morpholinomethyl)styryl)-1H-indazol-6-yl)spiro[cyclopropane-1,3'-indolin]-2'-one hydrochloride

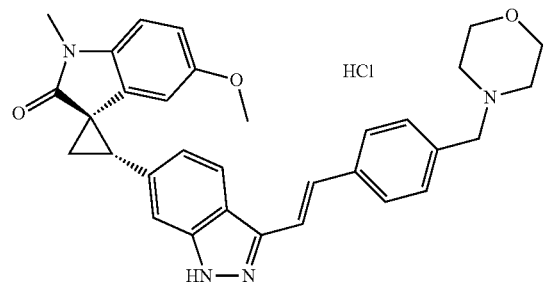 [SMILES: COc1ccc2c(c1)[C@]1(C[C@H]1c1ccc3c(/C=C/c4ccc(CN5CCOCC5)cc4)n[nH]c3c1)C(=O)N2C ; Cl]

The title compound was obtained according to the method of Example 11 from (1R,2S)-2-(3-iodo-1H-indazol-6-yl)-5'-methoxy-1'-methylspiro[cyclopropane-1,3'-indolin]-2'-one (Example 6C, 512 mg, 1.15 mmol) and (E)-4-(4-(2-(4,4,5,5-tetramethyl-1,3,2-dioxaborolan-2-yl)vinyl)benzyl)morpholine (454 mg, 1.38 mmol) with Pd(PPh$_3$)$_4$ (40 mg, 0.035 mmol, 3 mol %), LiCl (146 mg, 3.45 mmol) and Na$_2$CO$_3$ (1M, 5.8 mL, 5.8 mmol) in dioxane (12 mL) at 100° C. overnight in oil bath. Purification by column chromatography (silica gel, 5-8% MeOH in DCM) gave the free base as a yellow solid. The HCl salt was prepared according to the method of Example 8C, which gave after drying, the title product as a pale-yellow solid (346 mg, 54%); $^1$H NMR (400 MHz, CD$_3$OD) δ 8.02 (d, J=8.6 Hz, 1H), 7.77 (d, J=8.0 Hz, 2H), 7.56-7.49 (m, 5H), 7.04 (d, J=8.4 Hz, 1H), 6.92 (d, J=7.8 Hz, 1H), 6.69 (d, J=8.6 Hz, 1H), 5.63 (s, 1H), 4.39 (s, 2H), 4.08-4.05 (m, 2H), 3.77-3.71 (m, 2H), 3.35-3.23 (m, 11H), 2.27-2.25 (m, 1H), 2.22-2.19 (m, 1H); MS ESI [M+H]$^+$521.3, calcd for [C$_{32}$H$_{32}$N$_4$O$_3$+H]$^+$521.26; Optical Rotation: [α]$^{22}_D$=−85° (c 0.59, MeOH).

In a separate experiment, the title compound was also obtained according to the method of Example 8C, using (1R,2S)-2-(3-iodo-1H-indazol-6-yl)-5'-methoxy-1'-methyl-spiro[cyclopropane-1,3'-indolin]-2'-one (8.0 g, 18 mmol) and (E)-4-(4-(2-(4,4,5,5-tetramethyl-1,3,2-dioxaborolan-2-yl)vinyl)benzyl)morpholine (6.21 g, 18.9 mmol) with Pd(PPh$_3$)$_4$ (1.04 g, 0.9 mmol, 5 mol %) and Na$_2$CO$_3$ (1M, 36 mL, 36 mmol) in PhCH$_3$ (120 mL) and EtOH (60 mL) at 110° C. for 16 h. Purification and salt formation with HCl, followed by addition of water and lyophilization provided the title compound as a yellow solid (3.67 g, 39%, 96% e.e. as determined by chiral SFC with the major (1R,2S) enantiomer eluting at 3.2 min (Chiralpak AS-H (25×0.46 cm); 30% isobutanol (0.1% DEA)/CO$_2$, 100 bar; 3 mL/min; Detection: 254, 220 nm); From the racemic reference standard, the retention time of the (1S,2R) enantiomer was 1.9 min using this method.

By application of the methods described above but substituting with the appropriate (1R,2S)-2-(3-iodo-1H-indazol-6-yl)-spiro[cyclopropane-1,3'-indolin]-2'-one or (1S,2R)-2-(3-iodo-1H-indazol-6-yl)-spiro[cyclopropane-1,3'-indolin]-2'-one and boronic acids and/or boronate esters the following compounds were prepared:

(1R,2S)-(E)-2-(3-(4-((dimethylamino)methyl)-3,5-difluorostyryl)-1H-indazol-6-yl)-5'-methoxyspiro[cyclopropane-1,3'-indolin]-2'-one 2,2,2;

(1R,2S)-(E)-2-(3-(4-((diethylamino)methyl)styryl)-1H-indazol-6-yl)spiro-[cyclopropane-1,3'-indolin]-2'-one;

(1R,2S)-(E)-2-(3-(4-(2-morpholinoethyl)styryl)-1H-indazol-6-yl)spiro[cyclopropane-1,3'-indolin]-2'-one;

(1R,2S)-5'-methoxy-2-(3-((E)-2-(5-(morpholinomethyl)thiophen-3-yl)vinyl)-1H-indazol-6-yl)spiro[cyclopropane-1,3'-indolin]-2'-one;

(1R,2S)-(E)-2-(3-(3-(morpholinomethyl)styryl)-1H-indazol-6-yl)spiro[cyclopropane-1,3'-indolin]-2'-one;

(1R,2S)-2-(3-(4-(4-ethylpiperazin-1-yl)phenyl)-1H-indazol-6-yl)-5'-methoxyspiro[cyclopropane-1,3'-indolin]-2';

(1R,2S)-(E)-2-(3-(4-(1-methylpiperidin-4-yloxy)styryl)-1H-indazol-6-yl)spiro[cyclopropane-1,3'-indolin]-2'-one;

(1R,2S)-5'-methoxy-2-(3-((E)-2-(2-methyl-1,2,3,4-tetrahydroisoquinolin-6-yl)vinyl)-1H-indazol-6-yl)spiro[cyclopropane-1,3'-indolin]-2'-one;

(1R,2S)-(E)-2-(3-(4-((1,4-oxazepan-4-yl)methyl)styryl)-1H-indazol-6-yl)spiro[cyclopropane-1,3'-indolin]-2'-one;

(1R,2S)-2-(3-((E)-2-(2-methyl-1,2,3,4-tetrahydroisoquinolin-7-yl)vinyl)-1H-indazol-6-yl)spiro[cyclopropane-1,3'-indolin]-2'-one;

(1R,2S)-(E)-2-(3-(4-(pyrrolidin-1-ylmethyl)styryl)-1H-indazol-6-yl)spiro[cyclopropane-1,3'-indolin]-2'-one;

(1R,2S)-(E)-2-(3-(4-(morpholinomethyl)styryl)-1H-indazol-6-yl)spiro[cyclopropane-1,3'-indolin]-2'-one;

(1R,2S)-(E)-5'-methoxy-2-(3-(4-(2-morpholinoethyl)styryl)-1H-indazol-6-yl)spiro[cyclopropane-1,3'-indolin]-2'-one;

(1R,2S)-(E)-2-(3-(4-((dimethylamino)methyl)styryl)-1H-indazol-6-yl)spiro[cyclopropane-1,3'-indolin]-2'-one;

(1R,2S)-2-(3-((E)-2-(pyridin-3-yl)vinyl)-1H-indazol-6-yl)spiro[cyclopropane-1,3'-indolin]-2'-one;

(1R,2S)-5'-methoxy-2-(3-((E)-2-(6-(4-methylpiperazin-1-yl)pyridin-3-yl)vinyl)-H-indazol-6-yl)spiro[cyclopropane-1,3'-indolin]-2'-one;

(1R,2S)-(E)-2-(3-(4-((dimethylamino)methyl)styryl)-1H-indazol-6-yl)-5'-methoxyspiro[cyclopropane-1,3'-indolin]-2'-one;

(1R,2S)-(E)-5'-methoxy-2-(3-(4-(morpholinomethyl)styryl)-1H-indazol-6-yl)spiro[cyclopropane-1,3'-indolin]-2'-one;

(1R,2S)-5'-methoxy-2-(3-(4-(piperazin-1-yl)phenyl)-1H-indazol-6-yl)spiro[cyclopropane-1,3'-indolin]-2'-one;

(1R,2S)-(E)-2-(3-(4-(piperidin-1-ylmethyl)styryl)-1H-indazol-6-yl)spiro[cyclopropane-1,3'-indolin]-2'-one;

(1R,2S)-(E)-5'-methoxy-2-(3-(4-(piperidin-1-ylmethyl)styryl)-1H-indazol-6-yl)spiro[cyclopropane-1,3'-indolin]-2'-one;

(1R,2S)-(E)-2-(3-(4-(pyrrolidin-1-ylmethyl)styryl)-1H-indazol-6-yl)spiro[cyclopropane-1,3'-indolin]-2'-one;

(1R,2S)-5'-methoxy-2-(3-((E)-2-(2-methyl-1,2,3,4-tetrahydroisoquinolin-7-yl)vinyl)-H-indazol-6-yl)spiro[cyclopropane-1,3'-indolin]-2'-one;

(1R,2S)-2-(3-((E)-2-(2-methyl-1,2,3,4-tetrahydroisoquinolin-7-yl)vinyl)-1H-indazol-6-yl)spiro[cyclopropane-1,3'-indolin]-2'-one;

(1R,2S)-5'-methoxy-2-(3-(4-(2-(piperidin-1-yl)ethoxy)phenyl)-1H-indazol-6-yl)spiro[cyclopropane-1,3'-indolin]-2'-one;

(1R,2S)-5'-methoxy-2-(3-(4-(2-morpholinoethoxy)phenyl)-1H-indazol-6-yl)spiro[cyclopropane-1,3'-indolin]-2'-one;

(1R,2S)-2-(3-(4-(2-(dimethylamino)ethoxy)phenyl)-1H-indazol-6-yl)-5'-methoxyspiro[cyclopropane-1,3'-indolin]-2'-one;

(1R,2S)-5'-methoxy-2-(3-(2-methyl-1,2,3,4-tetrahydroisoquinolin-7-yl)-1H-indazol-6-yl)spiro[cyclopropane-1,3'-indolin]-2'-one;

(1R,2S)-5'-methoxy-2-(3-(1,2,3,4-tetrahydroisoquinolin-7-yl)-1H-indazol-6-yl)spiro[cyclopropane-1,3'-indolin]-2'-one;

(1R,2S)-(E)-2-(3-(4-((1,4-oxazepan-4-yl)methyl)styryl)-1H-indazol-6-yl)-5'-methoxyspiro[cyclopropane-1,3'-indolin]-2'-one;

(1R,2S)-2-(3-((E)-2-(2-methyl-1,2,3,4-tetrahydroisoquinolin-6-yl)vinyl)-1H-indazol-6-yl)spiro[cyclopropane-1,3'-indolin]-2'-one;

(1R,2S)-2-(3-(2-methyl-1,2,3,4-tetrahydroisoquinolin-6-yl)-1H-indazol-6-yl)spiro[cyclopropane-1,3'-indolin]-2'-one;

(1R,2S)-2-(3-((E)-2-(2-(morpholinomethyl)thiazol-4-yl)vinyl)-1H-indazol-6-yl)spiro[cyclopropane-1,3'-indolin]-2'-one;

(1R,2S)-(E)-5'-methoxy-2-(3-(4-(1-methylpiperidin-4-yloxy)styryl)-1H-indazol-6-yl)spiro[cyclopropane-1,3'-indolin]-2'-one;

(1R,2S)-(E)-2-(3-(4-(2-morpholinopropan-2-yl)styryl)-1H-indazol-6-yl)spiro [cyclopropane-1,3'-indolin]-2'-one;

(1R,2S)-(E)-2-(3-(4-((1-methylpiperidin-4-yl)methyl)styryl)-1H-indazol-6-yl)spiro[cyclopropane-1,3'-indolin]-2'-one;

(1R,2S)-(E)-5'-methoxy-2-(3-(4-((1-methylpiperidin-4-yl)methyl)styryl)-1H-indazol-6-yl)spiro[cyclopropane-1,3'-indolin]-2'-one;

(1R,2S)-(E)-1'-methyl-2-(3-(4-(piperazin-1-yl)styryl)-1H-indazol-6-yl)spiro[cyclopropane-1,3'-indolin]-2'-one;

(1R,2S)-(E)-2-(3-(4-(piperazin-1-yl)styryl)-1H-indazol-6-yl)spiro[cyclopropane-1,3'-indolin]-2'-one (1R,2S)-(E)-1'-methyl-2-(3-(4-(piperidin-1-ylmethyl)styryl)-1H-indazol-6-yl)spiro[cyclopropane-1,3'-indolin]-2'-one;

(1R,2S)-2-(3-(4-(4-isopropylpiperazin-1-yl)phenyl)-1H-indazol-6-yl)-5'-methoxyspiro[cyclopropane-1,3'-indolin]-2'-one;

(1R,2S)-5'-methoxy-2-(3-((E)-2-(5-(morpholinomethyl)thiophen-2-yl)vinyl)-1H-indazol-6-yl)spiro[cyclopropane-1,3'-indolin]-2'-one;

(1R,2S)-(E)-2-(3-(4-(((R)-3-fluoropyrrolidin-1-yl)methyl)styryl)-1H-indazol-6-yl)spiro[cyclopropane-1,3'-indolin]-2'-one;

(1R,2S)-2-(3-(imidazo[1,2-a]pyridin-6-yl)-1H-indazol-6-yl)-5'-methoxyspiro[cyclopropane-1,3'-indolin]-2'-one;

(1R,2S)-2-(3-(4-(2-(1H-imidazol-1-yl)ethoxy)phenyl)-1H-indazol-6-yl)-5'-methoxyspiro[cyclopropane-1,3'-indolin]-2'-one;

(1R,2S)-(E)-2-(3-(4-((dimethylamino)methyl)styryl)-1H-indazol-6-yl)-1'-methylspiro[cyclopropane-1,3'-indolin]-2'-one;

(1R,2S)-1'-methyl-2-(3-((E)-2-(6-(4-methylpiperazin-1-yl)pyridin-3-yl)vinyl)-1H-indazol-6-yl)spiro[cyclopropane-1,3'-indolin]-2'-one;

(1R,2S)-5'-methoxy-2-(3-((E)-2-(pyridin-4-yl)vinyl)-1H-indazol-6-yl)spiro[cyclopropane-1,3'-indolin]-2'-one;

(1R,2S)-(E)-2-(3-(4-(((R)-3-fluoropyrrolidin-1-yl)methyl)styryl)-1H-indazol-6-yl)-5'-methoxyspiro[cyclopropane-1,3'-indolin]-2'-one;

(1R,2S)-2-(3-((E)-2-(2,3,4,5-tetrahydrobenzo[f][1,4]oxazepin-7-yl)vinyl)-1H-indazol-6-yl)spiro[cyclopropane-1,3'-indolin]-2'-one;

(1R,2S)-2-(3-((E)-1-(4-(morpholinomethyl)phenyl)prop-1-en-2-yl)-1H-indazol-6-yl)spiro[cyclopropane-1,3'-indolin]-2'-one;

(1R,2S)-(E)-2-(3-(3,5-difluoro-4-(morpholinomethyl)styryl)-1H-indazol-6-yl)spiro[cyclopropane-1,3'-indolin]-2'-one;

(1R,2S)-2-(3-(4-(4-(dimethylamino)piperidin-1-yl)phenyl)-1H-indazol-6-yl)-5'-methoxyspiro[cyclopropane-1,3'-indolin]-2'-one;

(1R,2S)-5'-methoxy-2-(3-(4-(4-morpholinopiperidin-1-yl)phenyl)-1H-indazol-6-yl)spiro[cyclopropane-1,3'-indolin]-2'-one;

(1R,2S)-5'-methoxy-2-(3-(4-(1-methylpiperidin-4-yl)phenyl)-1H-indazol-6-yl)spiro[cyclopropane-1,3'-indolin]-2'-one;

(1R,2S)-2-(3-(4-(4-fluoro-1-methylpiperidin-4-yl)phenyl)-1H-indazol-6-yl)-5'-methoxyspiro[cyclopropane-1,3'-indolin]-2'-one;

(1R,2S)-5'-methoxy-2-(3-(5-(morpholinomethyl)thiophen-3-yl)-1H-indazol-6-yl)spiro[cyclopropane-1,3'-indolin]-2'-one;

(1R,2S)-2-(3-(4-(cis-3,5-dimethylpiperazin-1-yl)phenyl)-1H-indazol-6-yl)-5'-methoxyspiro[cyclopropane-1,3'-indolin]-2'-one;

(1R,2S)-2-(3-(4-((R)-3-(dimethylamino)pyrrolidin-1-yl)phenyl)-1H-indazol-6-yl)-5'-methoxyspiro[cyclopropane-1,3'-indolin]-2'-one;

(1R,2S)-2-(3-(4-((S)-3-(dimethylamino)pyrrolidin-1-yl)phenyl)-1H-indazol-6-yl)-5'-methoxyspiro[cyclopropane-1,3'-indolin]-2'-one;

(1R,2S)-2-(3-(4-((2-(dimethylamino)ethyl)(methyl)amino)phenyl)-1H-indazol-6-yl)-5'-methoxyspiro[cyclopropane-1,3'-indolin]-2'-one;

(1R,2S)-5'-methoxy-2-(3-(3-(morpholinomethyl)styryl)-1H-indazol-6-yl)spiro[cyclopropane-1,3'-indolin]-2'-one;

(1R,2S)-2-(3-(3-((dimethylamino)methyl)styryl)-1H-indazol-6-yl)-5'-methoxyspiro[cyclopropane-1,3'-indolin]-2'-one;

(1R,2S)-(E)-2-(3-(4-((diethylamino)methyl)-3,5-difluorostyryl)-1H-indazol-6-yl)-5'-methoxyspiro[cyclopropane-1,3'-indolin]-2'-one;

(1R,2S)-(E)-5'-methoxy-2-(3-(4-(4-methylpiperazin-1-yl)styryl)-1H-indazol-6-yl)spiro[cyclopropane-1,3'-indolin]-2'-one;

(1R,2S)-(E)-2-(3-(4-(4-ethylpiperazin-1-yl)styryl)-1H-indazol-6-yl)-5'-methoxyspiro[cyclopropane-1,3'-indolin]-2'-one;

(1R,2S)-2-(3-(4-(4-(2-hydroxyethyl)piperazin-1-yl)phenyl)-1H-indazol-6-yl)-5'-methoxyspiro[cyclopropane-1,3'-indolin]-2'-one;

(1R,2S)-2-(3-(4-(4-cyclopentylpiperazin-1-yl)phenyl)-1H-indazol-6-yl)-5'-methoxyspiro[cyclopropane-1,3'-indolin]-2'-one;

(1R,2S)-2-(3-(4-(4-cyclohexylpiperazin-1-yl)phenyl)-1H-indazol-6-yl)-5'-methoxyspiro[cyclopropane-1,3'-indolin]-2'-one;

(1R,2S)-(E)-5'-methoxy-2-(3-(4-(2-morpholinoethoxy)styryl)-1H-indazol-6-yl)spiro[cyclopropane-1,3'-indolin]-2'-one;

(1R,2S)-5'-methoxy-2-(3-((E)-2-(pyridin-3-yl)vinyl)-1H-indazol-6-yl)spiro[cyclopropane-1,3'-indolin]-2'-one;

(1R,2S)-(E)-2-(3-(3-fluoro-4-(morpholinomethyl)styryl)-1H-indazol-6-yl)-5'-methoxyspiro[cyclopropane-1,3'-indolin]-2'-one;

(1R,2S)-(E)-2-(3-(3-fluoro-4-(morpholinomethyl)styryl)-1H-indazol-6-yl)spiro[cyclopropane-1,3'-indolin]-2'-one (1R,2S)-(E)-2-(3-(4-((cis-2,6-dimethylpiperidin-1-yl)methyl)styryl)-1H-indazol-6-yl)spiro[cyclopropane-1,3'-indolin]-2'-one;

(1R,2S)-2-(3-((E)-2-(5-(morpholinomethyl)thiophen-3-yl)vinyl)-1H-indazol-6-yl)spiro[cyclopropane-1,3'-indolin]-2'-one;

(1R,2S)-(E)-2-(3-(4-((cis-2,6-dimethylpiperidin-1-yl)methyl)styryl)-1H-indazol-6-yl)-5'-methoxyspiro[cyclopropane-1,3'-indolin]-2'-one;

(1R,2S)-(E)-2-(3-(4-(2-morpholinoethoxy)styryl)-1H-indazol-6-yl)spiro[cyclopropane-1,3'-indolin]-2'-one;

(1R,2S)-(E)-2-(3-(4-((diethylamino)methyl)styryl)-1H-indazol-6-yl)-5'-methoxy spiro[cyclopropane-1,3'-indolin]-2'-one;

(1R,2S)-(E)-2-(3-(3,5-difluoro-4-(morpholinomethyl)styryl)-1H-indazol-6-yl)-5'-methoxyspiro[cyclopropane-1,3'-indolin]-2'-one;

(1R,2S)-(E)-2-(3-(4-((diethylamino)methyl)-3,5-difluorostyryl)-1H-indazol-6-yl)spiro[cyclopropane-1,3'-indolin]-2'-one;

(1R,2S)-5'-methoxy-2-(3-(4-(1-methylpiperidin-4-yloxy)phenyl)-1H-indazol-6-yl)spiro[cyclopropane-1,3'-indolin]-2'-one;

(1R,2S)-2-(3-(4-(3-(dimethylamino)azetidin-1-yl)phenyl)-1H-indazol-6-yl)-5'-methoxyspiro[cyclopropane-1,3'-indolin]-2'-one;

(1R,2S)-5'-methoxy-2-(3-(3-methyl-4-(4-methylpiperazin-1-yl)phenyl)-1H-indazol-6-yl)spiro[cyclopropane-1,3'-indolin]-2'-one;

(1R,2S)-5'-methoxy-2-(3-(3-methoxy-4-(4-methylpiperazin-1-yl)phenyl)-1H-indazol-6-yl)spiro[cyclopropane-1,3'-indolin]-2'-one;

(1R,2S)-5'-methoxy-2-(3-(4-(4-methyl-2-oxopiperazin-1-yl)phenyl)-1H-indazol-6-yl)spiro[cyclopropane-1,3'-indolin]-2'-one;

(1R,2S)-5'-methoxy-2-(3-(4-((3S,5R)-3,4,5-trimethylpiperazin-1-yl)phenyl)-1H-indazol-6-yl)spiro[cyclopropane-1,3'-indolin]-2'-one;

(1R,2S)-2-(3-((E)-4-((ethyl(2-methoxyethyl)amino)methyl)styryl)-1H-indazol-6-yl)spiro[cyclopropane-1,3'-indolin]-2'-one;

(1R,2S)-2-(3-((E)-4-((S)-1-morpholinoethyl)styryl)-1H-indazol-6-yl)spiro[cyclopropane-1,3'-indolin]-2'-one (1R,2S)-2-(3-((E)-4-(8-oxa-3-azabicyclo[3.2.1]octan-3-ylmethyl)styryl)-1H-indazol-6-yl)spiro[cyclopropane-1,3'-indolin]-2'-one;

(1R,2S)-2-(3-((E)-4-((1-isopropylpiperidin-4-yl)oxy)styryl)-1H-indazol-6-yl)spiro[cyclopropane-1,3'-indolin]-2'-one;

(1R,2S)-5'-methoxy-1'-methyl-2-(3-(4-(4-methylpiperazin-1-yl)phenyl)-1H-indazol-6-yl)spiro[cyclopropane-1,3'-indolin]-2'-one;

(1R,2S)-2-(3-((E)-3-(((2S,6R)-2,6-dimethylmorpholino)methyl)styryl)-1H-indazol-6-yl)-5'-methoxyspiro[cyclopropane-1,3'-indolin]-2'-one;

(1R,2S)-2-(3-((E)-3-(((2S,6R)-2,6-dimethylmorpholino)methyl)styryl)-1H-indazol-6-yl)spiro[cyclopropane-1,3'-indolin]-2'-one;

(1R,2S)-2-(3-((E)-4-(((2S,6R)-2,6-dimethylmorpholino)methyl)styryl)-1H-indazol-6-yl)-5'-methoxy-1'-methylspiro[cyclopropane-1,3'-indolin]-2'-one;

(1R,2S)-2-(3-((E)-4-(((2S,6R)-2,6-dimethylmorpholino)methyl)styryl)-1H-indazol-6-yl)-5'-methylspiro[cyclopropane-1,3'-indolin]-2'-one;

(1R,2S)-2-(3-((E)-3-(((2S,6R)-2,6-dimethylmorpholino)methyl)styryl)-1H-indazol-6-yl)-5'-methylspiro[cyclopropane-1,3'-indolin]-2'-one;

(1R,2S)-5'-methoxy-2-(3-((E)-4-(((2R,6S)-2,4,6-trimethylpiperazin-1-yl)methyl)styryl)-1H-indazol-6-yl)spiro[cyclopropane-1,3'-indolin]-2'-one;

(1R,2S)-5'-methoxy-2-(3-((E)-4-(((3S,5R)-3,4,5-trimethylpiperazin-1-yl)methyl)styryl)-1H-indazol-6-yl)spiro[cyclopropane-1,3'-indolin]-2'-one;

(1R,2S)-2-(3-((E)-4-(((3S,5R)-3,4,5-trimethylpiperazin-1-yl)methyl)styryl)-1H-indazol-6-yl)spiro[cyclopropane-1,3'-indolin]-2'-one;

(1R,2S)-2-(3-((E)-4-((bis(2-methoxyethyl)amino)methyl)styryl)-1H-indazol-6-yl)spiro[cyclopropane-1,3'-indolin]-2'-one;

(1R,2S)-2-(3-(4-(1-isopropylpiperidin-4-yloxy)phenyl)-1H-indazol-6-yl)-5'-methoxyspiro[cyclopropane-1,3'-indolin]-2'-one;

(1S,2R)-(E)-2-(3-(4-((dimethylamino)methyl)styryl)-1H-indazol-6-yl)spiro[cyclopropane-1,3'-indolin]-2'-one;

(1S,2R)-2-(3-((E)-2-(pyridin-3-yl)vinyl)-1H-indazol-6-yl)spiro[cyclopropane-1,3'-indolin]-2'-one;

(1S,2R)-(E)-2-(3-(4-((dimethylamino)methyl)styryl)-1H-indazol-6-yl)-5'-methoxyspiro[cyclopropane-1,3'-indolin]-2'-one;

(1S,2R)-5'-methoxy-2-(3-(4-(piperazin-1-yl)phenyl)-1H-indazol-6-yl)spiro[cyclopropane-1,3'-indolin]-2'-one;

(1S,2R)-(E)-2-(3-(4-cis-((2,6-dimethylmorpholino)methyl)styryl)-1H-indazol-6-yl)-5'-methoxyspiro[cyclopropane-1,3'-indolin]-2'-one;

(1S,2R)-5'-methoxy-2-(3-((E)-4-(morpholinomethyl)styryl)-1H-indazol-6-yl)spiro[cyclopropane-1,3'-indolin]-2'-one; and (1S,2R)-5'-methoxy-2-(3-((E)-2-(6-(4-methylpiperazin-1-yl)pyridin-3-yl)vinyl)-1H-indazol-6-yl)spiro[cyclopropane-1,3'-indolin]-2'-one.

The preparation of the compounds recited above and the remainder of the compounds depicted herein (including those depicted in the Exemplification), salts thereof (e.g., pharmaceutically acceptable salts) and the neutral form thereof, by the methods described herein are included in the invention. Also included is the preparation of the intermediates required in synthesis of these compounds by the disclosed methods. The compounds recited above and the remainder of the compound depicted herein (including those depicted in the Exemplification), the neutral form thereof and pharmaceutically acceptable salts thereof are included in the invention.

Preparation of Chiral Intermediate for X-Ray Structure Analysis

Example 17

(1R,2S)-2-(1-benzyl-3-iodo-1H-indazol-6-yl)-1'-methylspiro[cyclopropane-1,3'-indolin]-2'-one

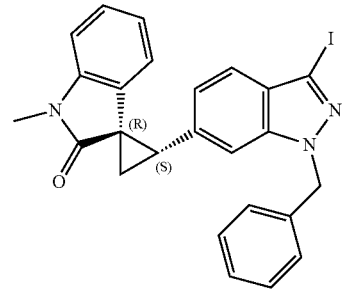

A round-bottom flask was charged with (1R,2S)-2-(3-iodo-1H-indazol-6-yl)-1'-methylspiro[cyclopropane-1,3'-indolin]-2'-one (200 mg, 0.482 mmol), tetrabutylammonium bromide (2.0 mg, 0.005 mmol), $CH_2Cl_2$ (3.5 mL), and KOH (1.0 mL, 50% wt aqueous solution). The mixture was then treated with BnBr (69 uL, 0.578 mmol) and the reaction stirred for 18 h at which time the product was extracted with $CH_2Cl_2$ (3×) and the combined organic layers washed with brine and dried over $MgSO_4$. After removal of solvent, purification using a Biotage Isolera (silica gel, 1-5% MeOH in DCM) gave the title compound. $^1$H NMR (400 MHz, $CDCl_3$) δ 7.35 (d, 1H, J=8.2 Hz), 7.29-7.25 (m, 3H), 7.15-7.10 (m, 4H), 6.97 (d, 1H, J=8.3 Hz), 6.85 (d, 1H, J=8.0 Hz), 6.56 (t, 1H, J=7.3 Hz), 5.72 (d, J=7.5 Hz, 1H), 5.63-5.49 (m, 2H), 3.39 (t, J=8.8 Hz, 1H), 3.32 (s, 3H), 2.22-2.19 (m, 1H), 1.97-1.94 (m, 1H); MS ESI 506.1 [M+H]$^+$, calcd for [$C_{25}H_{20}IN_3O$+H]$^+$ 506.07. Recrystallization from neat MeOH yielded clear, colorless crystals which were submitted for single crystal X-ray structure determination. The structure obtained (see FIGURE) confirmed the relative and absolute stereochemistry as (1R,2S), i.e. identical to that predicted by the "Sharpless mnemonic". The crystallographic data is summarized in the table below.

TABLE

Crystal data and structure refinement for compound example 17

| | |
|---|---|
| Empirical formula | C25H20I N30 |
| Formula weight | 505.34 |
| Temperature | 150(1) K |
| Wavelength | 0.71073 Å |
| Crystal system | Monoclinic |
| Space group | P 21 |
| Unit cell dimensions | a = 11.8719(4) Å  α = 90°. |
| | b = 5.72430(10) Å β = 95.2820(12)°. |
| | c = 15.4393(6) Å  γ = 90°. |
| Volume | 1044.77(6) Å$^3$ |
| Z | 2 |
| Density (calculated) | 1.606 Mg/m$^3$ |
| Absorption coefficient | 1.555 mm$^{-1}$ |
| F(000) | 504 |
| Crystal size | 0.22 × 0.06 × 0.05 mm$^3$ |
| Theta range for data collection | 2.65 to 27.52°. |
| Index ranges | −15<=h<=15, |
| | −7<=k<=7, |
| | −18<=l<=19 |
| Reflections collected | 7662 |
| Independent reflections | 4460 [R(int) = 0.0354] |
| Completeness to theta = 25.24° | 99.4% |
| Absorption correction | Semi-empirical from equivalents |
| Max. and min. transmission | 0.928 and 0.853 |
| Refinement method | Full-matrix least-squares on F$^2$ |
| Data/restraints /parameters | 4460/1/272 |
| Goodness-of-fit on F$^2$ | 1.069 |
| Final R indices [I > 2 sigma (I)] | R1 = 0.0363 |
| | wR2 = 0.0717 |
| R indices (all data) | R1 = 0.0465, |
| | wR2 = 0.0771 |
| Absolute structure parameter | −0.05(2) |
| Largest diff. peak and hole | 0.891 and −0.785 e.Å$^{-3}$ |

What is claimed is:

1. A method of preparing a diol compound represented by the following Structural Formula:

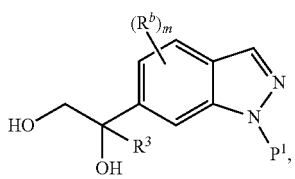

(V)

comprising the step of reacting a vinyl indazole compound represented by the following Structural Formula:

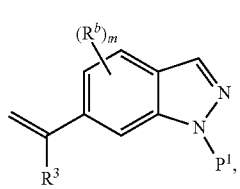

(IV)

with a dihydroxylation reagent, wherein:

each $R^b$ independently is —H, halogen, —C(O)OR$^1$, —C(O)R$^1$, —C(S)R$^1$, —OC(O)R$^1$—, —C(O)NR$^1$R$^2$, —C(S)NR$^1$R$^2$, —OC(O)NR$^1$R$^2$, —S(O)R$^1$, —S(O)$_2$R$^1$, —SO$_3$R$^1$, —SO$_2$NR$^1$R$^2$, —OR$^1$, —SR$^1$, —NR$^1$R$^2$, —NR$^2$C(O)R$^1$, —NR$^2$S(O)R$^1$, —NR$^2$C(O)OR$^1$, —NR$^2$C(O)ONR$^1$R$^2$, —N(R$^2$)C(O)NR$^1$R$^2$, —NR$^2$SO$_2$NR$^1$R$^2$, —NR$^2$SO$_2$R$^1$; —NO$_2$, —CN, —NCS; or two ortho R$^a$ groups taken together form —O—[CH$_2$]$_p$—O—, —S—[CH$_2$]$_p$—S— or —[CH$_2$]$_q$—; or C$_{1-10}$ aliphatic group optionally substituted with one or more substituents selected from the group consisting halogen, nitro, cyano, —N(R$^{21}$)$_2$, —C(O)N(R$^{21}$)$_2$, —C(O)N(R$^{21}$)$_2$, —NR$^{21}$C(O)R$^{21}$, —SO$_2$R$^{22}$, —SO$_2$N (R$^{21}$)$_2$, —NR$^{21}$SO$_2$R$^{22}$, —NR$^{21}$C(O)OR$^{21}$, —OC(O) N(R$^{21}$)$_2$, —NR$^{21}$C(O)N(R$^{21}$)$_2$, —NR$^{21}$C(O)ON(R$^{21}$)$_2$, —NR$^{21}$SO$_2$N(R$^{21}$)$_2$, —OR$^{21}$, —SR$^{21}$, C$_{1-10}$ haloalkoxy, —C(O)R$^{21}$, —C(O)OR$^{21}$ and —OC(O) R$^{21}$; or (C$_{0-10}$ alkylene)-Ar$^1$, wherein Ar$^1$ is a C$_{6-14}$ aryl group or a 5-14 membered heteroaryl group, each optionally and independently substituted with one or more substituents selected from the group consisting of halogen, nitro, cyano, C$_{1-10}$ alkyl, C$_{1-10}$haloalkyl, (C$_{1-10}$ haloalkoxy)C$_{1-10}$ alkyl, (C$_{1-10}$ alkoxy)C$_{1-10}$ alkyl, C$_{1-10}$ hydroxyalkyl, C$_{1-10}$ aminoalkyl, (C$_{1-10}$ alkylamino) C$_{1-10}$ alkyl, (C$_{1-10}$ dialkylamino)C$_{1-10}$ alkyl, —N(R$^{21}$)$_2$, —C(O)N(R$^{21}$)$_2$, —C(O)N(R$^{21}$)$_2$, —NR$^{21}$C (O)R$^{21}$, —SO$_2$R$^{22}$, —SO$_2$N(R$^{21}$)$_2$, —NR$^{21}$SO$_2$R$^{22}$, NR$^{21}$C(O)N(R$^{21}$)$_2$, —NR$^{21}$C(O)ON(R$^{21}$)$_2$, —NR$^{21}$SO$_2$N(R$^{21}$)$_2$, —OR$^{21}$, —SR$^{21}$, C$_{1-10}$ haloalkoxy, —C(O)R$^{21}$, —C(O)OR$^{21}$, —OC(O)R$^{21}$, phenyl and 5-6 membered heteroaryl, wherein said phenyl and said 5-6 membered heteroaryl are each independently and optionally substituted with one or more substituents selected from the group consisting of halogen, hydroxy, nitro, cyano, amino, C$_{1-3}$ alkyl, C$_{1-3}$ haloalkyl, C$_{1-3}$ alkoxy and C$_{1-3}$ haloalkoxy;

each R$^1$ independently is:
i) hydrogen;
ii) a C$_{6-14}$ aryl group or a 5-14 membered heteroaryl group, each optionally and independently substituted with one or more substituents selected from the group consisting of halogen, —NO$_2$, —CN, —NCS, C$_1$-C$_{10}$ aliphatic, (C$_{1-10}$ alkylene)-Ar$^{10}$, —C(O)OR$^{10}$, —C(O) R$^{10}$, —C(S)R$^{10}$, —OC(O)R$^{10}$, —C(O)N(R$^{11}$)$_2$, —C(S) N(R$^{11}$)$_2$, —OC(O)N(R$^{11}$)$_2$, —S(O)R$^{12}$, —S(O)$_2$R$^{12}$, —SO$_3$R$^{12}$, —SO$_2$N(R$^{11}$)$_2$, —OR$^{10}$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$ and —NR$^{11}$SO$_2$R$^{12}$; or
iii) a C$_{1-10}$ aliphatic group optionally substituted with one or more substituents selected from the group consisting of halogen, —NO$_2$, —CN, —NCS, Ar$^{10}$, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —OC(O)N(R$^{11}$)$_2$, —S(O)R$^{12}$, —S(O)$_2$ R$^{12}$, —SO$_3$R$^{12}$, —SO$_2$N(R$^{11}$)$_2$, —OR$^{10}$, —SR$^{10}$, —N(R$^{11}$)$_2$, —NR$^{11}$C(O)R$^{10}$, —NR$^{11}$S(O) R$^{12}$, —NR$^{11}$C(O)OR$^{12}$, —N(R$^{11}$)C(O)N(R$^{11}$)$_2$, —NR$^{11}$SO$_2$N(R$^{11}$)$_2$ and —NR$^{11}$SO$_2$R$^{12}$, provided that R$^1$ is other than hydrogen when R$^a$ or R$^b$ is —S(O)R$^1$, —S(O)$_2$R$^1$, —SO$_3$R$^1$, —NR$^2$S(O)R$^1$ or —NR$^2$SO$_2$R$^1$; and each R$^2$ independently is —H or C$_1$-C$_6$ alkyl, or, taken together with NR$^1$, forms a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl;

$R^3$ is —H, halogen, $C_{1-6}$ alkyl or $C_{1-6}$ haloalkyl;

each $R^{10}$ independently is:
i) hydrogen;
ii) a $C_{6-14}$ aryl group or a 5-14 membered heteroaryl group, each optionally and independently substituted with one or more substituents selected from the group consisting of halogen, nitro, cyano, hydroxy, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$-alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ alkoxy, $C_{1-10}$ haloalkoxy, $C_{1-10}$ alkylcarbonyloxy, $C_{1-10}$ alkoxycarbonyl and $C_{1-10}$ alkylcarbonyl; or
iii) a $C_{1-10}$ alkyl group optionally substituted with one or more substituents selected from the group consisting of halogen, nitro, cyano, hydroxy, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each $R^{11}$ independently is $R^{10}$, —$CO_2R^{10}$, —$SO_2R^{10}$ or —$C(O)R^{10}$, or —$N(R^{11})_2$ taken together is a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl; and each $R^{12}$ is independently is $R^{10}$ provided that $R^{12}$ is not hydrogen;

each $R^{21}$ independently is hydrogen, $C_{1-6}$ alkyl, phenyl or 5-6 membered heteroaryl, wherein each of the phenyl and heteroaryl groups represented by $R^{21}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{21}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{21}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy; or $N(R^{21})_2$ forms a non-aromatic heterocyclic group optionally substituted with one or more substituents selected from the group consisting of halogen, hydroxy, nitro, cyano, =O, $C_{1-3}$ alky, $C_{1-3}$ haloalkyl, $C_{1-3}$ alkoxy, $C_{1-3}$ haloalkoxy and amino; and each $R^{22}$ independently $C_{1-6}$ alkyl, phenyl or 5-6 membered heteroaryl, wherein each of the phenyl and heteroaryl groups represented by $R^{22}$ is independently and optionally substituted with one or substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{22}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each $Ar^{10}$ independently is a $C_{6-14}$ aryl group or a 5-14 membered heteroaryl group, each optionally and independently substituted with one or more substituents selected from the group consisting of halogen, nitro, cyano, —OH, —SH, —O($C_{1-10}$ alkyl), —S($C_{1-10}$ alkyl), $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, ($C_{1-10}$ aminoalkyl, ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ haloalkoxy, $C_{1-10}$ alkylcarbonyloxy, $C_{1-10}$ alkoxycarbonyl and $C_{1-10}$ alkylcarbonyl;

$P^1$ is —H or a nitrogen protecting group;
each p is 1, 2 or 3;
each q is 2, 3, 4 or 5; and
m is 1 or 2.

2. The method of claim 1, wherein the diol compound is represented by the following Structural Formula:

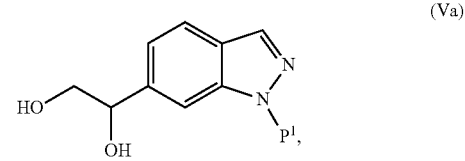

(Va)

and the vinyl indazole compound is represented by the following Structural Formula:

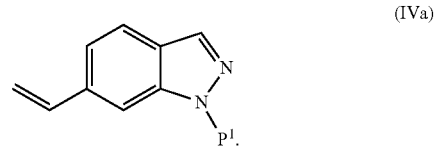

(IVa)

3. The method of claim 2, wherein the diol compound is represented by the following Structural Formula:

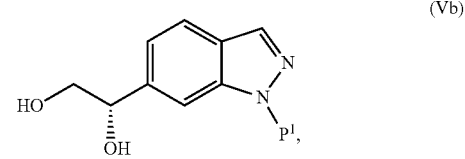

(Vb)

and the dihydroxylation step is carried out in the presence of a chiral induction agent.

4. The method of claim 3, wherein the chiral induction agent comprises (DHQ)-$_2$PHAL or Q$_2$(PHAL) and wherein the dihydroxylation reagent comprises an osmium reagent and an oxidant.

5. The method of claim 4, wherein the osmium reagent is OsO$_4$ or potassium osmate and the oxidant is selected from the group consisting of t-BuOOH, N-methylmorpholine-N-oxide (NMO) and K$_3$Fe(CN)$_6$.

6. The method of claim 1, wherein the dihydroxylation is carried out in the presence of a base, wherein the base is an alkali carbonate, an alkali hydroxide, an amine or an ammonium hydroxide.

7. The method of claim 1, wherein the dihydroxylation is carried out in the presence of an acid, wherein the acid is citric acid or acetic acid.

8. The method of claim 1, wherein the dihydroxylation is carried out in a mixture of water and an organic solvent.

9. The method of claim 1, wherein the dihydroxylation is carried out at a temperature ranging from 0° C. to 50° C.

10. The method of claim 1, wherein P$^1$ is benzyl optionally substituted one or more substituents independently selected from the group consisting of halogen, nitro, C$_{1-6}$ alkyl, C$_{1-6}$ alkoxy, and (C$_{1-6}$ alkoxy)C$_{1-6}$ alkyl.

11. The method of claim 10, wherein P$^1$ is benzyl, p-methoxybenzyl, 3,4-dimethoxybenzyl, 3-methoxybenzyl, 3,5-dimethoxybenzyl, p-nitrobenzyl or 2,4-dinitrobenzyl.

12. A compound represented by the following Structural Formula:

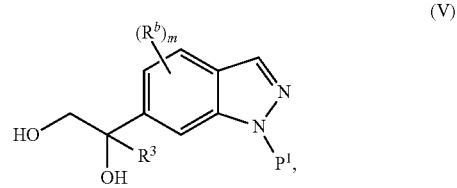

(V)

wherein:
- each of R$^b$ independently is —H, halogen, —C(O)OR$^1$, —C(O)R$^1$, —C(S)R$^1$, —OC(O)R$^1$—, —C(O)NR$^1$R$^2$, —C(S)NR$^1$R$^2$, —OC(O)NR$^1$R$^2$, —S(O)R$^1$, —S(O)$_2$R$^1$, —SO$_3$R$^1$, —SO$_2$NR$^1$R$^2$, —OR$^1$, —SR$^1$, —NR$^1$R$^2$, —NR$^2$C(O)R$^1$, —NR$^2$S(O)R$^1$, —NR$^2$C(O)OR$^1$, —NR$^2$C(O)ONR$^1$R$^2$, —N(R$^2$)C(O)NR$^1$R$^2$, —NR$^2$SO$_2$NR$^1$R$^2$, —NR$^2$SO$_2$R$^1$; —NO$_2$, —CN, —NCS; or two ortho R$^a$ groups taken together form —O—[CH$_2$]$_p$—O—, —S—[CH$_2$]$_p$—S— or —[CH$_2$]$_q$—; or
C$_{1-10}$ aliphatic group optionally substituted with one or more substituents selected from the group consisting halogen, nitro, cyano, —N(R$^{21}$)$_2$, —C(O)N(R$^{21}$)$_2$, —C(O)N(R$^{21}$)$_2$, —NR$^{21}$C(O)R$^{21}$, —SO$_2$R$^{22}$, —SO$_2$N(R$^{21}$)$_2$, —NR$^{21}$SO$_2$R$^{22}$, —NR$^{21}$C(O)OR$^{21}$, —OC(O)N(R$^{21}$)$_2$, —NR$^{21}$C(O)N(R$^{21}$)$_2$, —NR$^{21}$C(O)ON(R$^{21}$)$_2$, —NR$^{21}$SO$_2$N(R$^{21}$)$_2$, —OR$^{21}$, —SR$^{21}$, C$_{1-10}$ haloalkoxy, —C(O)R$^{21}$, —C(O)OR$^{21}$ and —OC(O)R$^{21}$; or
(C$_{0-10}$ alkylene)-Ar$^1$, wherein Ar$^1$ is a C$_{6-14}$ aryl group or a 5-14 membered heteroaryl group, each optionally and independently substituted with one or more substituents selected from the group consisting of halogen, nitro, cyano, C$_{1-10}$ alkyl, C$_{1-10}$-haloalkyl, (C$_{1-10}$ haloalkoxy)C$_{1-10}$ alkyl, (C$_{1-10}$ alkoxy)C$_{1-10}$ alkyl, C$_{1-10}$ hydroxyalkyl, C$_{1-10}$ aminoalkyl, (C$_{1-10}$ alkylamino)C$_{1-10}$ alkyl, (C$_{1-10}$ dialkylamino)C$_{1-10}$ alkyl, —N(R$^{21}$)$_2$, —C(O)N(R$^{21}$)$_2$, —C(O)N(R$^{21}$)$_2$, —SO$_2$R$^{22}$, —SO$_2$N(R$^{21}$)$_2$, —NR$^{21}$SO$_2$R$^{22}$, —NR$^{21}$C(O)N(R$^{21}$)$_2$, —NR$^{21}$C(O)ON(R$^{21}$)$_2$, —NR$^{21}$SO$_2$N(R$^{21}$)$_2$, —OR$^{21}$, —SR$^{21}$, C$_{1-10}$ haloalkoxy, —C(O)R$^{21}$, —C(O)OR$^{21}$, —OC(O)R$^{21}$, phenyl and 5-6 membered heteroaryl, wherein said phenyl and said 5-6 membered heteroaryl are each independently and optionally substituted with one or more substituents selected from the group consisting of halogen, hydroxy, nitro, cyano, amino, C$_{1-3}$ alkyl, C$_{1-3}$ haloalkyl, C$_{1-3}$ alkoxy and C$_{1-3}$ haloalkoxy;

each R$^1$ independently is:
i) hydrogen;
ii) a C$_{6-14}$ aryl group or a 5-14 membered heteroaryl group, each optionally and independently substituted with one or more substituents selected from the group consisting of halogen, —NO$_2$, —CN, —NCS, C$_1$-C$_{10}$ aliphatic, (C$_{1-10}$ alkylene)-Ar$^{10}$, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —OC(O)N(R$^{11}$)$_2$, —S(O)R$^{12}$, —S(O)$_2$R$^{12}$, —SO$_3$R$^{12}$, —SO$_2$N(R$^{11}$)$_2$, —OR$^{10}$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$ and —NR$^{11}$SO$_2$R$^2$; or
iii) a C$_{1-10}$ aliphatic group optionally substituted with one or more substituents selected from the group consisting of halogen, —NO$_2$, —CN, —NCS, Ar$^{10}$, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —OC(O)N(R$^{11}$)$_2$, —S(O)R$^{12}$, —S(O)$_2$ R$^{12}$, —SO$_3$R$^{12}$, —SO$_2$N(R$^{11}$)$_2$, —OR$^{10}$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$ and —NR$^{11}$SO$_2$R$^{12}$,
provided that R$^1$ is other than hydrogen when R$^a$ or R$^b$ is —S(O)R$^1$, —S(O)$_2$R$^1$, —SO$_3$R$^1$, —NR$^2$S(O)R$^1$ or —NR$^2$SO$_2$R$^1$; and each R$^2$ independently is —H or C$_1$-C$_6$ alkyl, or, taken together with NR$^1$, forms a non-aromatic heterocyclic group optionally substituted with one or more substituents selected from the group consisting of =O, =S, halogen, nitro, cyano, hydroxy, C$_{1-6}$ alkyl, C$_{1-6}$ haloalkyl, C$_{1-6}$ hydroxyalkyl, amino, C$_{1-6}$ alkylamino, C$_{1-6}$ dialkylamino, C$_{1-6}$ aminoalkyl, (C$_{1-6}$ alkylamino) C$_{1-6}$ alkyl, (C$_{1-6}$ dialkylamino)C$_{1-6}$ alkyl, (phenyl)C$_{1-6}$ alkyl, (5-6 membered heteroaryl)C$_{1-6}$ alkyl, C$_{1-6}$ alkoxy, C$_{1-6}$ haloalkoxy, C$_{1-6}$ alkylcarbonyloxy, C$_{1-6}$ alkoxycarbonyl, C$_{1-6}$ alkylcarbonyl, phenyl and 5-6 membered heteroaryl;

R$^3$ is —H, C$_{1-6}$ alkyl or C$_{1-6}$haloalkyl;
each R$^{10}$ independently is:
i) hydrogen;
ii) a C$_{6-14}$ aryl group or a 5-14 membered heteroaryl group, each optionally and independently substituted with one or more substituents selected from the group consisting of halogen, nitro, cyano, hydroxy, C$_{1-10}$ alkyl, C$_{1-10}$ haloalkyl, (C$_{1-10}$ haloalkoxy)C$_{1-10}$ alkyl, (C$_{1-10}$ alkoxy)C$_{1-10}$ alkyl, C$_{1-10}$ hydroxyalkyl, C$_{1-10}$ aminoalkyl, (C$_{1-10}$ alkylamino)C$_{1-10}$ alkyl, (C$_{1-10}$ dialkylamino)C$_{1-10}$-alkyl, (phenyl)C$_{1-10}$ alkyl, (5-6 membered heteroaryl)C$_{1-10}$ alkyl, amino, C$_{1-10}$ alkylamino, C$_{1-10}$ dialkylamino, C$_{1-10}$ alkoxy, C$_{1-10}$ haloalkoxy, C$_{1-10}$ alkylcarbonyloxy, C$_{1-10}$ alkoxycarbonyl and C$_{1-10}$ alkylcarbonyl; or
iii) a C$_{1-10}$ alkyl group optionally substituted with one or more substituents selected from the group consisting of halogen, nitro, cyano, hydroxy, C$_{1-10}$ haloalkyl, C$_{1-10}$ alkoxy, C$_{1-10}$ haloalkoxy, amino, C$_{1-10}$ alkylamino, C$_{1-10}$ dialkylamino, C$_{1-10}$ alkylcarbonyloxy, C$_{1-10}$ alkoxycarbonyl, C$_{1-10}$alkylcarbonyl and phenyl, said phenyl being optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each $R^{11}$ independently is $R^{10}$, —$CO_2R^{10}$, —$SO_2R^{10}$ or —$C(O)R^{10}$, or —$N(R^{11})_2$ taken together is a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl; and each $R^{12}$ is independently is $R^{10}$ provided that $R^{12}$ is not hydrogen;

each $R^{21}$ independently is hydrogen, $C_{1-6}$ alkyl, phenyl or 5-6 membered heteroaryl, wherein each of the phenyl and heteroaryl groups represented by $R^{21}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{21}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy; or $N(R^{21})_2$ forms a non-aromatic heterocyclic group optionally substituted with one or more substituents selected from the group consisting of halogen, hydroxy, nitro, cyano, =O, $C_{1-3}$ alky, $C_{1-3}$ haloalkyl, $C_{1-3}$ alkoxy, $C_{1-3}$ haloalkoxy and amino; and each $R^{22}$ independently $C_{1-6}$ alkyl, phenyl or 5-6 membered heteroaryl, wherein each of the phenyl and heteroaryl groups represented by $R^{22}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{22}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each $Ar^{10}$ independently is a $C_{6-14}$ aryl group or a 5-14 membered heteroaryl group, each optionally and independently substituted with one or more substituents selected from the group consisting of halogen, nitro, cyano, —OH, —SH, —O($C_{1-10}$ alkyl), —S($C_{1-10}$ alkyl), $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, ($C_{1-10}$ aminoalkyl, ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ haloalkoxy, $C_{1-10}$ alkylcarbonyloxy, $C_{1-10}$ alkoxycarbonyl and $C_{1-10}$ alkylcarbonyl;

$P^1$ is —H or a nitrogen protecting group;

each p is 1, 2 or 3;

each q is 2, 3, 4 or 5; and m is 0, 1 or 2.

13. The compound of claim 12, wherein the compound is represented by the following Structural Formula:

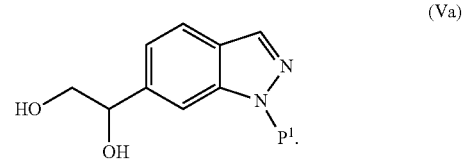

(Va)

14. The compound of claim 13, wherein the compound is represented by the following Structural Formula:

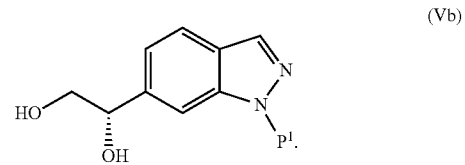

(Vb)

15. The compound of claim 14, wherein:

$P^1$ is —C(=O)O—$R^p$, —$SO_2$—$R^p$, tetrahydro-2H-pyran-2-yl or benzyl optionally substituted one or more substituents independently selected from the group consisting of halogen, nitro, $C_{1-6}$ alkly, $C_{1-6}$ alkoxy, and ($C_{1-6}$ alkoxy)$C_{1-6}$ alkyl; and $R^P$ is $C_{1-6}$ alkyl, $C_{1-6}$ haloalkyl, —$C_{1-6}$ alkylene—Si($C_{1-6}$ alkyl)$_3$, phenyl optionally substituted with one or more substituents indepently selected from the group consisting of halogen, nitro, $C_{1-6}$ alkyl, $C_{1-6}$ alkoxy, and ($C_{1-6}$ alkoxy)$C_{1-6}$ alkyl.

16. The compound of claim 15, wherein $P^1$ is benzyl or p-methoxybenzyl.

* * * * *